US012352750B2

(12) United States Patent
Varley et al.

(10) Patent No.: US 12,352,750 B2
(45) Date of Patent: Jul. 8, 2025

(54) MULTIGENE ASSAY TO ASSESS RISK OF RECURRENCE OF CANCER

(71) Applicant: UNIVERSITY OF UTAH RESEARCH FOUNDATION, Salt Lake City, UT (US)

(72) Inventors: Katherine (K-T) E. Varley, Salt Lake City, UT (US); Rachel L. Stewart, Lexington, KY (US); Philip S. Bernard, Salt Lake City, UT (US); Katherine Updike, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 940 days.

(21) Appl. No.: 17/598,185

(22) PCT Filed: Apr. 3, 2020

(86) PCT No.: PCT/US2020/026727
§ 371 (c)(1),
(2) Date: Sep. 24, 2021

(87) PCT Pub. No.: WO2020/206359
PCT Pub. Date: Oct. 8, 2020

(65) Prior Publication Data
US 2022/0178925 A1 Jun. 9, 2022

Related U.S. Application Data

(60) Provisional application No. 62/829,440, filed on Apr. 4, 2019.

(51) Int. Cl.
*G01N 31/00* (2006.01)
*G01N 33/53* (2006.01)
*G01N 33/574* (2006.01)

(52) U.S. Cl.
CPC . *G01N 33/57415* (2013.01); *G01N 33/57484* (2013.01)

(58) Field of Classification Search
None
See application file for complete search history.

(56) References Cited

U.S. PATENT DOCUMENTS

| 4,554,101 A | 11/1985 | Hopp |
| 9,002,653 B2 | 4/2015 | Semizarov et al. |
| 2008/0032293 A1 | 2/2008 | Szabo et al. |
| 2014/0134626 A1* | 5/2014 | Ray ........ C12Q 1/6881 435/7.1 |
| 2015/0072021 A1 | 3/2015 | Cheang et al. |
| 2017/0363629 A1 | 12/2017 | Radvanyi et al. |

FOREIGN PATENT DOCUMENTS

| WO | WO-2006010150 A2 * | 1/2006 | ..... C12Q 1/6886 |
| WO | WO2016037009 A1 | 3/2016 | |

OTHER PUBLICATIONS

European Patent Office Extended European Search Report for application 20783128.0, dated Apr. 4, 2023 (12 pages).
Adams et al., "Prognostic value of tumor-infiltrating lymphocytes in triple-negative breast cancers from two phase III randomized adjuvant breast cancer trials: ECOG 2197 and ECOG 1199", J Clin Oncol., 2014, vol. 32, No. 27, pp. 2959-2966.
Addington et al., "Chemotherapy-induced peripheral neuropathy: an update on the current understanding", F1000Res, 2016, vol. 5, pp. 1-7.
Ahles et al., "Cancer- and cancer treatment-associated cognitive change: an update on the state of the science", J Clin Oncol., 2012, vol. 30, No. 30, pp. 3675-3686.
Armstrong et al., "MHC class II-transfected tumor cells directly present antigen to tumor-specific CD4+ T lymphocytes", J Immunol, 1998, vol. 160, No. 2, pp. 661-666.
Ashburner et al., "Gene ontology: tool for the unification of biology", The Gene Ontology Consortium, Nat Genet, 2000, vol. 25, No. 1, pp. 25-29.
Axelrod et al., "Biological Consequences of MHC-II Expression by Tumor Cells in Cancer", Clin Cancer Res, 2018, vol. 25, No. 8, pp. 2392-2402.
Bastien et al., "PAM50 breast cancer subtyping by RT-qPCR and concordance with standard clinical molecular markers", BMC Med Genomics, 2012, vol. 5, No. 44, pp. 1-12.
Bengtsson et al., "Gene expression profiling in single cells from the pancreatic islets of Langerhans reveals lognormal distribution of mRNA levels", Genome Res, 2005, vol. 15, No. 10, pp. 1388-1392.

(Continued)

*Primary Examiner* — Lisa V Cook
(74) *Attorney, Agent, or Firm* — Michael Best & Friedrich LLP

(57) ABSTRACT

Disclosed herein are biomarkers and methods of using the same for determining the risk of recurrence of cancer in a subject. The methods may include determining the level of expression of at least one MHCII gene, determining the level of expression of at least one TIL gene, and determining an Immune Activation Score for the subject. Further provided are methods of diagnosing a subject with triple-negative breast cancer (TNBC) as having TNBC Basal-like subtype, and methods of treating cancer in a subject.

29 Claims, 49 Drawing Sheets
Specification includes a Sequence Listing.

(56) References Cited

OTHER PUBLICATIONS

Bowles et al., "Risk of heart failure in breast cancer patients after anthracycline and trastuzumab treatment: a retrospective cohort study", J Natl Cancer Inst, 2012, vol. 104, No. 17, pp. 1293-1305.

Cronin et al., "Measurement of gene expression in archival paraffin-embedded tissues: development and performance of a 92-gene reverse transcriptase-polymerase chain reaction assay", Am J Pathol, 2004, vol. 164, No. 1, pp. 35-42.

Denkert et al., "Standardized evaluation of tumor-infiltrating lymphocytes in breast cancer: results of the ring studies of the international immuno-oncology biomarker working group", Mod Pathol, 2016, vol. 29, No. 10, pp. 1155-1164.

Denkert et al., "Tumour-infiltrating lymphocytes and prognosis in different subtypes of breast cancer: a pooled analysis of 3771 patients treated with neoadjuvant therapy", Lancet Oncol., 2018, vol. 19, No. 1, pp. 40-50.

Dent et al., Triple-negative breast cancer: clinical features and patterns of recurrence, Clin Cancer Res, 2007, vol. 13, No. 15 Pt 1, pp. 4429-4434.

Dowsett et al., "Comparison of PAM50 risk of recurrence score with oncotype DX and IHC4 for predicting risk of distant recurrence after endocrine therapy", J Clin Oncol 2013, vol. 31, No. 22, pp. 2783-2790.

Duffy et al., "Clinical use of biomarkers in breast cancer: Updated guidelines from the European Group on Tumor Markers (EGTM)", Eur J Cancer, 2017, vol. 75, pp. 284-298.

Forero et al., "Expression of the MHC Class II Pathway in Triple-Negative Breast Cancer Tumor Cells Is Associated with a Good Prognosis and Infiltrating Lymphocytes", Cancer Immunol Res, 2016, vol. 4, No. 5, pp. 390-399.

Frangione et al., "CIITA-driven MHC-II positive tumor cells: preventive vaccines and superior generators of antitumor CD4+ T lymphocytes for immunotherapy", Int J Cancer, 2010, vol. 127, No. 7, pp. 1614-1624.

Garcia-Teijido et al., "Tumor-Infiltrating Lymphocytes in Triple Negative Breast Cancer: The Future of Immune Targeting", Clin Med Insights Oncol ,2016, vol. 10, pp. 31-39.

Geiss et al., "Direct multiplexed measurement of gene expression with color-coded probe pairs", Nat Biotechnol, 2008, vol. 26, No. 3, pp. 317-325.

Gnant et al., "Predicting distant recurrence in receptor-positive breast cancer patients with limited clinicopathological risk: using the PAM50 Risk of Recurrence score in 1478 postmenopausal patients of the ABCSG-8 trial treated with adjuvant endocrine therapy alone", Ann Oncol, 2014, vol. 25, No. 2, pp. 339-345.

Gyorffy et al., "An online survival analysis tool to rapidly assess the effect of 22,277 genes on breast cancer prognosis using microarray data of 1,809 patients", Breast Cancer Res Treat, 2010, vol. 123, No. 3, pp. 725-731.

Gyorffy et al., "Implementing an online tool for genome-wide validation of survival-associated biomarkers in ovarian-cancer using microarray data from 1287 patients", Endocrine-Related Cancer, 2012, vol. 19, pp. 197-208.

Gyorffy et al., "Online Survival Analysis Software to Assess the Prognostic Value of Biomarkers Using Transcriptomic Data in Non-Small-Cell Lung Cancer", PLoS One, 2013, vol. 8, e82241, 8 pages.

Heagerty et al., "Time-Dependent ROC Curves for Censored Survival Data and a Diagnostic Marker", Biometrics, 2000, vol. 56, pp. 337-344.

Hubalek et al., "Biological Subtypes of Triple-Negative Breast Cancer", Breast Care (Basel), 2017, vol. 12, No. 1, pp. 8-14.

Ilkovitch et al., "MHC class II and CD80 tumor cell-based vaccines are potent activators of type 1 CD4+ T lymphocytes provided they do not coexpress invariant chain", Cancer Immunol Immunother., 2004, vol. 53, No. 6, pp. 525-532.

International Preliminary Report on Patentability for Application No. PCT/US20/26727 dated Sep. 28, 2021 (11 pages).

International Search Report and Written Opinion for Application No. PCT/US20/26727 dated Jul. 28, 2020 (19 pages).

Johnson et al., "Melanoma-specific MHC-II expression represents a tumour-autonomous phenotype and predicts response to anti-PD-1/PD-L1 therapy", Nat Commun., 2016, vol. 7, No. 10582, pp. 1-11.

Johnson et al., "Tumor-specific MHC-II expression drives a unique pattern of resistance to immunotherapy via LAG-3/FCRL6 engagement", JCI Insight, 2018, vol. 3, No. 24., pp. 1-18.

Kirova et al., "Second malignancies after breast cancer: the impact of different treatment modalities", Br J Cancer, 2008, vol. 98, No. 5, pp. 870-874.

Kyte et al., "A Simple Method for Displaying the Hydropathic Character of a Protein", J. Miol. Biol., 1982, vol. 157, pp. 105-132.

Lee et al., "Prognostic and predictive value of NanoString-based immune-related gene signatures in a neoadjuvant setting of triple-negative breast cancer: relationship to tumor- infiltrating lymphocytes", Breast Cancer Res Treat., 2015, vol. 151, No. 3, pp. 619-627.

LeibundGut-Landmann et al.,. "Mini-review: Specificity and expression of CIITA, the master regulator of MHC class II genes", Eur J Immunol, 2004, vol. 34, No. 6, pp. 1513-1525.

Li et al., "Jetset: selecting the optimal microarray probe set to represent a gene", BMC Bioinformatics, 2011, vol. 12, No. 474, pp. 1-7.

Loi et al., "Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98", J Clin Oncol., 2013, vol. 31, No. 7, pp. 860-867.

Loi et al., "Tumor-Infiltrating Lymphocytes and Prognosis: A Pooled Individual Patient Analysis of Early-Stage Triple-Negative Breast Cancers", J Clin Oncol., 2019, vol. 37, No. 7, pp. 559-570.

Mao et al., "The Prognostic Value of Tumor-Infiltrating Lymphocytes in Breast Cancer: A Systematic Review and Meta-Analysis", PLoS One, 2016, vol. 11, No. 4, p. e0152500.

Meazza et al., "Tumor rejection by gene transfer of the MHC class II transactivator in murine mammary adenocarcinoma cells", Eur J Immunol., 2003, vol. 33, No. 5, pp. 1183-1192.

Mi et al., "PANTHER version 11: expanded annotation data from Gene Ontology and Reactome pathways, and data analysis tool enhancements", Nucleic Acids Res, 2017, vol. 45, No. D1, pp. D183-D189.

Mihaly et al., "Improving Pathological Assessment of Breast Cancer by Employing Array-Based Transcriptome Analysis", Microarrays (Basel), 2013, vol. 2, No. 3, pp. 228-242.

Mortara et al., "CIITA-induced MHC class II expression in mammary adenocarcinoma leads to a Th1 polarization of the tumor microenvironment, tumor rejection, and specific antitumor memory", Clin Cancer Res, 2006, vol. 12, No. 11 Pt 1, pp. 3435-3443.

Nanda et al., "Pembrolizumab plus standard neoadjuvant therapy for high-risk breast cancer (BC): Results from I-SPY 2". Journal of Clinical Oncology, 2017, vol. 35.

Newman et al., "The 2014 Society of Surgical Oncology Susan G. Komen for the Cure Symposium: triple-negative breast cancer", Ann Surg Oncol., 2015, vol. 22, No. 3, pp. 874-882.

Nielsen et al., "A comparison of PAM50 intrinsic subtyping with immunohistochemistry and clinical prognostic factors in tamoxifen-treated estrogen receptor-positive breast cancer.", Clin Cancer Res 2010, vol. 16, No. 21, pp. 5222-5232.

Nielsen et al., "Analytical validation of the PAM50-based Prosigna Breast Cancer Prognostic Gene Signature Assay and nCounter Analysis System using formalin-fixed paraffin-embedded breast tumor specimens", BMC Cancer, 2014, vol. 14, No. 177, pp. 1-14.

Nirmal et al., "Immune Cell Gene Signatures for Profiling the Microenvironment of Solid Tumors", Cancer Immunol Res, 2018, vol. 6, No. 11, pp. 1388-1400.

O'Loughlin et al., "Reproducibility and predictive value of scoring stromal tumour infiltrating lymphocytes in triple-negative breast cancer: a multi-institutional study", Breast Cancer Res Treat, 2018, vol. 171, No. 1, pp. 1-9.

Paik et al., "Gene expression and benefit of chemotherapy in women with node-negative, estrogen receptor-positive breast cancer", J Clin Oncol, 2006, vol. 24, No. 23, pp. 3726-3734.

(56) References Cited

OTHER PUBLICATIONS

Park et al., "Expression of the MHC class II in triple-negative breast cancer is associated with tumor-infiltrating lymphocytes and interferon signaling", PLoS One 2017, vol. 12, No. 8, e0182786.

Parker et al., Supervised risk predictor of breast cancer based on intrinsic subtypes. J Clin Oncol 2009;27(8):1160-7 doi 10.1200/JCO.2008.18.1370.

Pulaski et al., "Reduction of established spontaneous mammary carcinoma metastases following immunotherapy with major histocompatibility complex class II and B7.1 cell-based tumor vaccines", Cancer Res., 1998, vol. 58, No. 7, pp. 1486-1493.

Reis et al., "mRNA transcript quantification in archival samples using multiplexed, color-coded probes", BMC Biotechnol., 2011, vol. 11, No. 46., pp. 1-10.

Salgado et al., "The evaluation of tumor-infiltrating lymphocytes (TILs) in breast cancer: recommendations by an International TILs Working Group 2014", Ann Oncol., 2015, vol. 26, No. 2, pp. 259-271.

Savas et al., "Single-cell profiling of breast cancer T cells reveals a tissue-resident memory subset associated with improved prognosis", Nat Med, 2018, vol. 24, No. 7, pp. 986-993.

Seretny et al., "Incidence, prevalence, and predictors of chemotherapy-induced peripheral neuropathy: A systematic review and meta-analysis", Pain, 2014, vol. 155, No. 12, pp. 2461-2470.

Sestak et al., "Comparison of the Performance of 6 Prognostic Signatures for Estrogen Receptor—Positive Breast Cancer: A Secondary Analysis of a Randomized Clinical Trial", JAMA Oncol, 2018, vol. 4, No. 4, pp. 545-553.

Sharma et al., "Efficacy of Neoadjuvant Carboplatin plus Docetaxel in Triple-Negative Breast Cancer: Combined Analysis of Two Cohorts", Clin. Cancer Res., 2017, vol. 23, pp. 649-657.

Sparano et al., "Adjuvant Chemotherapy Guided by a 21-Gene Expression Assay in Breast Cancer", N Engl J Med, 2018, vol. 379, No. 2, pp. 111-121.

Sparano et al., "Development of the 21-gene assay and its application in clinical practice and clinical trials", J Clin Oncol., 2008, vol. 26, No. 5, pp. 721-728.

Steimle et al., "Regulation of MHC class II expression by interferon-gamma mediated by the transactivator gene CIITA", Science, 1994, vol. 265, No. 5168, pp. 106-109.

Stovgaard et al., "Triple negative breast cancer—prognostic role of immune-related factors: a systematic review", Acta Oncol., 2018, vol. 57, No. 1, pp. 74-82.

Szabo et al., "Statistical modeling for selecting housekeeper genes", Genome Biol., 2004, vol. 5, No. 8, pp. R59.

The Gene Ontology Consortium, "The Gene Ontology Resource: 20 years and still Going strong", Nucleic Acids Res, 2019, vol. 47, Database Issue, pp. D330-D338.

Thompson et al., "Tumor cells transduced with the MHC class II Transactivator and CD80 activate tumor-specific CD4+ T cells whether or not they are silenced for invariant chain", Cancer Res., 2006, vol. 66, No. 2, pp. 1147-1154.

Van de Vijver et al., "A gene-expression signature as a predictor of survival in breast cancer", N Engl J Med., 2002, vol. 347, No. 25, pp. 1999-2009.

Vandesompele et al., "Accurate normalization of real-time quantitative RT-PCR data by geometric averaging of multiple internal control genes", Genome Biol., 2002, vol. 3, No. 7, 12 pages.

Varley et al., "Recurrent read-through fusion transcripts in breast cancer", Breast Cancer Res Treat, 2014, vol. 146, No. 2, pp. 287-297.

Von Ahlfen et al., "Determinants of RNA quality from FFPE samples", PLoS One, 2007, vol. 2, No. 12, e1261.

Wallden et al., "Development and verification of the PAM50-based Prosigna breast cancer gene signature assay", BMC Med Genomics, 2015, vol. 8, No. 54, pp. 1-14.

Wang et al., "The CD4/CD8 ratio of tumor-infiltrating lymphocytes at the tumor-host interface has prognostic value in triple-negative breast cancer", Hum Pathol., 2017;, vol. 69, pp. 110-117.

Winters-Stone et al., "Falls, Functioning, and Disability Among Women With Persistent Symptoms of Chemotherapy-Induced Peripheral Neuropathy", J Clin Oncol., 2017, vol. 35, No. 23, pp. 2604-2612.

Yan et al., "CD4+ T cell-mediated cytotoxicity eliminates primary tumor cells in metastatic melanoma through high MHC class II expression and can be enhanced by inhibitory receptor blockade", Tumour Biol., 2016, 10 pages.

European Patent Office Partial Supplementary European Search Report for application 20783128.0, dated Jan. 2, 2023 (15 pages).

\* cited by examiner

| Training Set | | True Class | | |
|---|---|---|---|---|
| | | No Relapse | Relapse | |
| Predicted Class | No Relapse | 7 | 1 | Positive Predictive Value 87.5% |
| | Relapse | 12 | 19 | Negative Predictive Value 61.3% |
| | | Sensitivity 36.8% | Specificity 95% | Accuracy 66.6% |

FIG. 11A

| Validation Cohort | | True Class | | |
|---|---|---|---|---|
| | | No Relapse | Relapse | |
| Predicted Class | No Relapse | 7 | 0 | Positive Predictive Value 100% |
| | Relapse | 22 | 16 | Negative Predictive Value 42.1% |
| | | Sensitivity 24.1% | Specificity 100% | Accuracy 51.1% |

FIG. 11B

SEQUENCE LISTING

<160> NUMBER OF SEQ ID NOS: 108

<210> SEQ ID NO 1
<211> LENGTH: 100
<212> TYPE: DNA
<213> ORGANISM: Homo sapiens

<400> SEQUENCE: 1
tgcagaagga gatcactgcc ctggcaccca gcacaatgaa gatcaagatc attgctcctc    60
ctgagcgcaa gtactccgtg tggatcggcg gctccatcct                          100

<210> SEQ ID NO 2
<211> LENGTH: 85
<212> TYPE: DNA
<213> ORGANISM: Artificial sequence
<220> FEATURE:
<223> OTHER INFORMATION: synthetic construct

<400> SEQUENCE: 2
gatcttgatc ttcattgtgc tgggtgccag ggcagtgatc tccttctgca cctcaagacc    60
taagcgacag cgtgaccttg tttca                                          85

<210> SEQ ID NO 3
<211> LENGTH: 75
<212> TYPE: DNA
<213> ORGANISM: Artificial sequence
<220> FEATURE:
<223> OTHER INFORMATION: synthetic construct

<400> SEQUENCE: 3
cgaaagccat gacctccgat cactcaggat ggagccgccg atccacacgg agtacttgcg    60
ctcaggagga gcaat                                                     75

```
<210> SEQ ID NO 4
<211> LENGTH: 100
<212> TYPE: DNA
<213> ORGANISM: Homo sapiens

<400> SEQUENCE: 4
tgactgtctc tatcttcatg agtgtgactt gaggtgttgg gatgggtgag ggagcttctc    60
taaagaggaa agtgagtgga ttaacccctg cttctcttct                         100

<210> SEQ ID NO 5
<211> LENGTH: 85
<212> TYPE: DNA
<213> ORGANISM: Artificial sequence
<220> FEATURE:
<223> OTHER INFORMATION: synthetic construct

<400> SEQUENCE: 5
ctcacccatc ccaacacctc aagtcacact catgaagata gagacagtca catcctcttc    60
ttttcttggt gttgagaaga tgctc                                          85

<210> SEQ ID NO 6
<211> LENGTH: 75
<212> TYPE: DNA
<213> ORGANISM: Artificial sequence
<220> FEATURE:
<223> OTHER INFORMATION: synthetic construct

<400> SEQUENCE: 6
cgaaagccat gacctccgat cactcagaag agaagcaggg gttaatccac tcactttcct    60
ctttagagaa gctcc                                                     75

<210> SEQ ID NO 7
<211> LENGTH: 100
<212> TYPE: DNA
<213> ORGANISM: Homo sapiens

<400> SEQUENCE: 7
cctccagaca ccagtgcgtg ctcccgatgc tgctatggaa ggtgctactt gacctaaggg    60
actcccacaa caacaaaagc ttgaagctgt ggagggccac                         100

<210> SEQ ID NO 8
<211> LENGTH: 72
<212> TYPE: DNA
<213> ORGANISM: Artificial sequence
<220> FEATURE:
<223> OTHER INFORMATION: synthetic construct

<400> SEQUENCE: 8
aagtagcacc ttccatagca gcatcgggag cacgcaccac aattctgcgg gttagcagga    60
aggttaggga ac                                                        72

<210> SEQ ID NO 9
<211> LENGTH: 71
<212> TYPE: DNA
<213> ORGANISM: Artificial sequence
<220> FEATURE:
<223> OTHER INFORMATION: synthetic construct

<400> SEQUENCE: 9
cgaaagccat gacctccgat cactcccctc cacagcttca agcttttgtt gttgtgggag    60
tcccttaggt c                                                         71
```

```
<210> SEQ ID NO 10
<211> LENGTH: 100
<212> TYPE: DNA
<213> ORGANISM: Homo sapiens

<400> SEQUENCE: 10
agcttcccga ggctccgcac cagccgcgct tctgtccgcc tgcagggcat tccagaaaga      60
tgaggatatt tgctgtcttt atattcatga cctactggca                           100

<210> SEQ ID NO 11
<211> LENGTH: 83
<212> TYPE: DNA
<213> ORGANISM: Artificial sequence
<220> FEATURE:
<223> OTHER INFORMATION: synthetic construct

<400> SEQUENCE: 11
atgccctgca ggcggacaga agcgcggctg gtgcggagcc tcgggaagct gttgagatta      60
ttgagcttca tcatgaccag aag                                              83

<210> SEQ ID NO 12
<211> LENGTH: 75
<212> TYPE: DNA
<213> ORGANISM: Artificial sequence
<220> FEATURE:
<223> OTHER INFORMATION: synthetic construct

<400> SEQUENCE: 12
cgaaagccat gacctccgat cactctgcca gtaggtcatg aatataaaga cagcaaatat      60
cctcatcttt ctgga                                                       75

<210> SEQ ID NO 13
<211> LENGTH: 100
<212> TYPE: DNA
<213> ORGANISM: Homo sapiens

<400> SEQUENCE: 13
tatctactgg atgagttccg ctgggagatg aacatagca cgtttctctc tggcctggta       60
ctggctaccc ttctctcgca agtgagcccc ttcaagatac                           100

<210> SEQ ID NO 14
<211> LENGTH: 85
<212> TYPE: DNA
<213> ORGANISM: Artificial sequence
<220> FEATURE:
<223> OTHER INFORMATION: synthetic construct

<400> SEQUENCE: 14
gagagaaacg tgctatgttc catctcccag cggaactcat ccagtagata caaagacgcc      60
tatcttccag tttgatcggg aaact                                            85

<210> SEQ ID NO 15
<211> LENGTH: 60
<212> TYPE: DNA
<213> ORGANISM: Artificial sequence
<220> FEATURE:
<223> OTHER INFORMATION: synthetic construct

<400> SEQUENCE: 15
cgaaagccat gacctccgat cactctcact tgcgagagaa gggtagccag taccaggcca      60
```

```
<210> SEQ ID NO 16
<211> LENGTH: 100
<212> TYPE: DNA
<213> ORGANISM: Homo sapiens

<400> SEQUENCE: 16
tggcaggcgg agagggcttc ctcctccaag tcttggatca cctttgacct gaagaacaag      60
gaagtgtctg taaaacgggt tacccaggac cctaagctcc                          100

<210> SEQ ID NO 17
<211> LENGTH: 80
<212> TYPE: DNA
<213> ORGANISM: Artificial sequence
<220> FEATURE:
<223> OTHER INFORMATION: synthetic construct

<400> SEQUENCE: 17
aggtcaaagg tgatccaaga cttggaggag gaagccctct ccgcccgaac ctaactcctc      60
gctacattcc tattgttttc                                                80

<210> SEQ ID NO 18
<211> LENGTH: 70
<212> TYPE: DNA
<213> ORGANISM: Artificial sequence
<220> FEATURE:
<223> OTHER INFORMATION: synthetic construct

<400> SEQUENCE: 18
cgaaagccat gacctccgat cactcttagg gtcctgggta accgttttta cagacacttc      60
cttgttcttc                                                           70

<210> SEQ ID NO 19
<211> LENGTH: 100
<212> TYPE: DNA
<213> ORGANISM: Homo sapiens

<400> SEQUENCE: 19
aggacatgaa ctttctaaaa cgatacgcag gtagagagga acactgggtt ggactgaaaa      60
aggaacctgg tcacccatgg aagtggtcaa atggcaaaga                          100

<210> SEQ ID NO 20
<211> LENGTH: 85
<212> TYPE: DNA
<213> ORGANISM: Artificial sequence
<220> FEATURE:
<223> OTHER INFORMATION: synthetic construct

<400> SEQUENCE: 20
aacccagtgt tcctctctac ctgcgtatcg ttttagaaag ttcatgtcct ccaatttggt      60
tttactcccc tcgattatgc ggagt                                          85

<210> SEQ ID NO 21
<211> LENGTH: 75
<212> TYPE: DNA
<213> ORGANISM: Artificial sequence
<220> FEATURE:
<223> OTHER INFORMATION: synthetic construct

<400> SEQUENCE: 21
cgaaagccat gacctccgat cactctcttt gccatttgac cacttccatg ggtgaccagg      60
ttcctttttc agtcc                                                     75
```

<210> SEQ ID NO 22
<211> LENGTH: 100
<212> TYPE: DNA
<213> ORGANISM: Homo sapiens

<400> SEQUENCE: 22
ttcagccccc agccctccc ccatctccca ccctgtacct catcccatga gaccctggtg      60
cctggctctt tcgtcaccct tggacaagac aaaccaagtc                          100

<210> SEQ ID NO 23
<211> LENGTH: 70
<212> TYPE: DNA
<213> ORGANISM: Artificial sequence
<220> FEATURE:
<223> OTHER INFORMATION: synthetic construct

<400> SEQUENCE: 23
tcatgggatg aggtacaggg tgggagatgg gggagctttc gggttatatc tatcatttac      60
ttgacaccct                                                             70

<210> SEQ ID NO 24
<211> LENGTH: 72
<212> TYPE: DNA
<213> ORGANISM: Artificial sequence
<220> FEATURE:
<223> OTHER INFORMATION: synthetic construct

<400> SEQUENCE: 24
cgaaagccat gacctccgat cactcttggt ttgtcttgtc caagggtgac gaaagagcca      60
ggcaccaggg tc                                                          72

<210> SEQ ID NO 25
<211> LENGTH: 100
<212> TYPE: DNA
<213> ORGANISM: Homo sapiens

<400> SEQUENCE: 25
gctcagggct ctttcctcca caccattcag gtctttcttt ccgaggcccc tgtctcaggg      60
tgaggtgctt gagtctccaa cggcaaggga acaagtactt                          100

<210> SEQ ID NO 26
<211> LENGTH: 85
<212> TYPE: DNA
<213> ORGANISM: Artificial sequence
<220> FEATURE:
<223> OTHER INFORMATION: synthetic construct

<400> SEQUENCE: 26
ggggcctcgg aaagaaagac ctgaatggtg tggaggaaag agccctgagc caacagccac      60 ttttttttcca aattttgcaa gagcc                                            85

<210> SEQ ID NO 27
<211> LENGTH: 75
<212> TYPE: DNA
<213> ORGANISM: Artificial sequence
<220> FEATURE:
<223> OTHER INFORMATION: synthetic construct

<400> SEQUENCE: 27
cgaaagccat gacctccgat cactcaagta cttgttccct tgccgttgga gactcaagca      60
cctcaccctg agaca                                                       75

<210> SEQ ID NO 28
<211> LENGTH: 100
<212> TYPE: DNA
<213> ORGANISM: Homo sapiens

<400> SEQUENCE: 28
ggaacatcag aaagcctggg ctttgaacct gaacggtttt gatgtagagg aagccaagat    60
ccttcggctc agtggaaaac cacaaaatgc gccagagggt                         100

<210> SEQ ID NO 29
<211> LENGTH: 85
<212> TYPE: DNA
<213> ORGANISM: Artificial sequence
<220> FEATURE:
<223> OTHER INFORMATION: synthetic construct

<400> SEQUENCE: 29
cctctacatc aaaaccgttc aggttcaaag cccaggcttt ctgatgttcc caccgtgtgg    60
acggcaactc agagataacg catat                                         85

<210> SEQ ID NO 30
<211> LENGTH: 75
<212> TYPE: DNA
<213> ORGANISM: Artificial sequence
<220> FEATURE:
<223> OTHER INFORMATION: synthetic construct

<400> SEQUENCE: 30
cgaaagccat gacctccgat cactcaccct ctggcgcatt ttgtggtttt ccactgagcc    60
gaaggatctt ggctt                                                    75

<210> SEQ ID NO 31
<211> LENGTH: 100
<212> TYPE: DNA
<213> ORGANISM: Homo sapiens

<400> SEQUENCE: 31
ctttccccaa actggtgcgg atcctcacgg ccttttcctc cctgcagcat ctggacctgg    60
atgcgctgag tgagaacaag atcggggacg agggtgtctc                         100

<210> SEQ ID NO 32
<211> LENGTH: 85
<212> TYPE: DNA
<213> ORGANISM: Artificial sequence
<220> FEATURE:
<223> OTHER INFORMATION: synthetic construct

<400> SEQUENCE: 32
atgctgcagg gaggaaaagg ccgtgaggat ccgcaccagt ttggggaaag cctggagttt    60
atgtattgcc aacgagtttg tcttt                                         85

<210> SEQ ID NO 33
<211> LENGTH: 67
<212> TYPE: DNA
<213> ORGANISM: Artificial sequence
<220> FEATURE:
<223> OTHER INFORMATION: synthetic construct

<400> SEQUENCE: 33
cgaaagccat gacctccgat cactcctcgt ccccgatctt gttctcactc agcgcatcca    60

```
ggtccag                                                              67

<210> SEQ ID NO 34
<211> LENGTH: 100
<212> TYPE: DNA
<213> ORGANISM: Homo sapiens

<400> SEQUENCE: 34
cagacatgag ctttgctgaa ataaaacaca agtatctctg gtcagagcct cagaattgct   60
cagccaccaa aagtaactac cttcgaggta ctggtcccta                         100

<210> SEQ ID NO 35
<211> LENGTH: 85
<212> TYPE: DNA
<213> ORGANISM: Artificial sequence
<220> FEATURE:
<223> OTHER INFORMATION: synthetic construct

<400> SEQUENCE: 35
aggctctgac cagagatact tgtgttttat ttcagcaaag ctcatgtctg cagataaggt   60
tgttattgtg gaggatgtta ctaca                                         85

<210> SEQ ID NO 36
<211> LENGTH: 71
<212> TYPE: DNA
<213> ORGANISM: Artificial sequence
<220> FEATURE:
<223> OTHER INFORMATION: synthetic construct

<400> SEQUENCE: 36
cgaaagccat gacctccgat cactcgacca gtacctcgaa ggtagttact tttggtggct   60
gagcaattct g                                                        71

<210> SEQ ID NO 37
<211> LENGTH: 100
<212> TYPE: DNA
<213> ORGANISM: Homo sapiens

<400> SEQUENCE: 37
acagacacgt ttgagtccat gcccaatccc gagggccggt atacattcgg cgccagctgt   60
gtgactgcct gtccctacaa ctacctttct acggacgtgg                         100

<210> SEQ ID NO 38
<211> LENGTH: 82
<212> TYPE: DNA
<213> ORGANISM: Artificial sequence
<220> FEATURE:
<223> OTHER INFORMATION: synthetic construct

<400> SEQUENCE: 38
ccgaatgtat accggccctc gggattgggc atggactcaa acgtgtcctt ccttcctgtg   60
ttccagctac aaacttagaa ac                                            82

<210> SEQ ID NO 39
<211> LENGTH: 68
<212> TYPE: DNA
<213> ORGANISM: Artificial sequence
<220> FEATURE:
<223> OTHER INFORMATION: synthetic construct

<400> SEQUENCE: 39
cgaaagccat gacctccgat cactccgtag aaaggtagtt gtagggacag gcagtcacac   60
```

-continued agctggcg                                                              68

<210> SEQ ID NO 40
<211> LENGTH: 100
<212> TYPE: DNA
<213> ORGANISM: Homo sapiens

<400> SEQUENCE: 40
aggaaccagg gaaaatgtgt agagggcatg gtggagatct tcgacatgct gctggctaca    60
tcatctcggt tccgcatgat gaatctgcag ggagaggagt                         100

<210> SEQ ID NO 41
<211> LENGTH: 82
<212> TYPE: DNA
<213> ORGANISM: Artificial sequence
<220> FEATURE:
<223> OTHER INFORMATION: synthetic construct

<400> SEQUENCE: 41
agcatgtcga agatctccac catgccctct acacattttc cctggttcat aaaattggtt    60
ttgcctttca gcaattcaac tt                                             82

<210> SEQ ID NO 42
<211> LENGTH: 68
<212> TYPE: DNA
<213> ORGANISM: Artificial sequence
<220> FEATURE:
<223> OTHER INFORMATION: synthetic construct

<400> SEQUENCE: 42
cgaaagccat gacctccgat cactctccct gcagattcat catgcggaac cgagatgatg    60
tagccagc                                                             68

<210> SEQ ID NO 43
<211> LENGTH: 100
<212> TYPE: DNA
<213> ORGANISM: Homo sapiens

<400> SEQUENCE: 43
tgatacattc tcaagagttg cttgaccgaa agttacaagg accccaaccc ctttgtcctc    60
tctacccaca gatggccctg ggaatcaatt cctcaggaat                         100

<210> SEQ ID NO 44
<211> LENGTH: 85
<212> TYPE: DNA
<213> ORGANISM: Artificial sequence
<220> FEATURE:
<223> OTHER INFORMATION: synthetic construct

<400> SEQUENCE: 44
gggttggggt ccttgtaact ttcggtcaag caactcttga gaatgtatca ctggtcaaga    60
cttgcatgag gacccgcaaa ttcct                                          85

<210> SEQ ID NO 45
<211> LENGTH: 75
<212> TYPE: DNA
<213> ORGANISM: Artificial sequence
<220> FEATURE:
<223> OTHER INFORMATION: synthetic construct

<400> SEQUENCE: 45

```
cgaaagccat gacctccgat cactcattcc tgaggaattg attcccaggg ccatctgtgg    60
gtagagagga caaag                                                     75

<210> SEQ ID NO 46
<211> LENGTH: 100
<212> TYPE: DNA
<213> ORGANISM: Homo sapiens

<400> SEQUENCE: 46
tcggtgcggg agatgttcga gtcacagagg atcggcttga caactctcc agtgaacggg    60 aatagtagct gtcaaatggc cttcccttcc agccagtctc                         100

<210> SEQ ID NO 47
<211> LENGTH: 79
<212> TYPE: DNA
<213> ORGANISM: Artificial sequence
<220> FEATURE:
<223> OTHER INFORMATION: synthetic construct

<400> SEQUENCE: 47
ggagagttgt tcaagccgat cctctgtgac tcgaacatct cccgctttcg ttgggacgct    60
tgaagcgcaa gtagaaaac                                                 79

<210> SEQ ID NO 48
<211> LENGTH: 75
<212> TYPE: DNA
<213> ORGANISM: Artificial sequence
<220> FEATURE:
<223> OTHER INFORMATION: synthetic construct

<400> SEQUENCE: 48
cgaaagccat gacctccgat cactcgagac tggctggaag ggaaggccat ttgacagcta    60
ctattcccgt tcact                                                     75

<210> SEQ ID NO 49
<211> LENGTH: 100
<212> TYPE: DNA
<213> ORGANISM: Homo sapiens

<400> SEQUENCE: 49
ttatttgaca aagagttctg cgagtggatg atccagcaaa tagggccaaa acttgatggg    60
aaaatcccgg tgtccagagg gtttcctatc gctgaagtgt                         100

<210> SEQ ID NO 50
<211> LENGTH: 85
<212> TYPE: DNA
<213> ORGANISM: Artificial sequence
<220> FEATURE:
<223> OTHER INFORMATION: synthetic construct

<400> SEQUENCE: 50
tttggcccta tttgctggat catccactcg cagaactctt tgtcaaataa ccagcagacc    60
tgcaatatca agttataag cgcgt                                           85

<210> SEQ ID NO 51
<211> LENGTH: 75
<212> TYPE: DNA
<213> ORGANISM: Artificial sequence
<220> FEATURE:
<223> OTHER INFORMATION: synthetic construct

<400> SEQUENCE: 51
```

```
cgaaagccat gacctccgat cactcacact tcagcgatag gaaaccctct ggacaccggg    60
attttcccat caagt                                                    75

<210> SEQ ID NO 52
<211> LENGTH: 100
<212> TYPE: DNA
<213> ORGANISM: Homo sapiens

<400> SEQUENCE: 52
cccgtgagct ggaaggaaca gatttaatat ctaggggctg gtatcccca catcactcat    60 ttgggggtc aagggacccg ggcaatatag tattctgctc                         100

<210> SEQ ID NO 53
<211> LENGTH: 83
<212> TYPE: DNA
<213> ORGANISM: Artificial sequence
<220> FEATURE:
<223> OTHER INFORMATION: synthetic construct

<400> SEQUENCE: 53
tggggatacc cagcccctag atattaaatc tgttccttcc agctcacgcc tgccaatgca    60
ctcgatcttg tcattttttt gcg                                           83

<210> SEQ ID NO 54
<211> LENGTH: 75
<212> TYPE: DNA
<213> ORGANISM: Artificial sequence
<220> FEATURE:
<223> OTHER INFORMATION: synthetic construct

<400> SEQUENCE: 54
cgaaagccat gacctccgat cactcgagca gaatactata ttgcccgggt cccttgaccc    60
cccaaatgag tgatg                                                    75

<210> SEQ ID NO 55
<211> LENGTH: 100
<212> TYPE: DNA
<213> ORGANISM: Homo sapiens

<400> SEQUENCE: 55
ggagagatct gaactccagc tgccctacaa actccatctc agcttttctt ctcacttcat    60
gtgaaaacta ctccagtggc tgactgaatt gctgacccctt                       100

<210> SEQ ID NO 56
<211> LENGTH: 85
<212> TYPE: DNA
<213> ORGANISM: Artificial sequence
<220> FEATURE:
<223> OTHER INFORMATION: synthetic construct

<400> SEQUENCE: 56
aagaaaagct gagatggagt ttgtagggca gctggagttc agatctctcc caaactggag    60
agagaagtga agacgattta accca                                         85

<210> SEQ ID NO 57
<211> LENGTH: 75
<212> TYPE: DNA
<213> ORGANISM: Artificial sequence
<220> FEATURE:
<223> OTHER INFORMATION: synthetic construct
```

<400> SEQUENCE: 57
cgaaagccat gacctccgat cactcaaggg tcagcaattc agtcagccac tggagtagtt    60
ttcacatgaa gtgag                                                    75

<210> SEQ ID NO 58
<211> LENGTH: 100
<212> TYPE: DNA
<213> ORGANISM: Homo sapiens

<400> SEQUENCE: 58
tccaaattgg atactgctgc caagaagttg ctctgaagtc agtttctatc attctgctct    60
ttgattcaaa gcactgtttc tctcactggg cctccaacca                         100

<210> SEQ ID NO 59
<211> LENGTH: 85
<212> TYPE: DNA
<213> ORGANISM: Artificial sequence
<220> FEATURE:
<223> OTHER INFORMATION: synthetic construct

<400> SEQUENCE: 59
gatagaaact gacttcagag caacttcttg gcagcagtat ccaatttgga cgattgctgc    60
attccgctca acgcttgagg aagta                                         85

<210> SEQ ID NO 60
<211> LENGTH: 75
<212> TYPE: DNA
<213> ORGANISM: Artificial sequence
<220> FEATURE:
<223> OTHER INFORMATION: synthetic construct

<400> SEQUENCE: 60
cgaaagccat gacctccgat cactctggtt ggaggcccag tgagagaaac agtgctttga    60
atcaaagagc agaat                                                    75

<210> SEQ ID NO 61
<211> LENGTH: 100
<212> TYPE: DNA
<213> ORGANISM: Homo sapiens

<400> SEQUENCE: 61
ggtggcctga gttcagcaaa tttggaggtt ttgacccgca gggtgcactg agaaacatgg    60
ctgtggcaaa acacaacttg aacatcatga ttaaacgcta                         100

<210> SEQ ID NO 62
<211> LENGTH: 85
<212> TYPE: DNA
<213> ORGANISM: Artificial sequence
<220> FEATURE:
<223> OTHER INFORMATION: synthetic construct

<400> SEQUENCE: 62
cagtgcaccc tgcgggtcaa aacctccaaa tttgctgaac tcaggccacc ctgaggctgt    60
taaagctgta gcaactcttc cacga                                         85

<210> SEQ ID NO 63
<211> LENGTH: 75
<212> TYPE: DNA
<213> ORGANISM: Artificial sequence
<220> FEATURE:
<223> OTHER INFORMATION: synthetic construct

<400> SEQUENCE: 63
cgaaagccat gacctccgat cactctagcg tttaatcatg atgttcaagt tgtgttttgc       60
cacagccatg tttct                                                        75

<210> SEQ ID NO 64
<211> LENGTH: 100
<212> TYPE: DNA
<213> ORGANISM: Homo sapiens

<400> SEQUENCE: 64
tgcagacaca actacggggt tgtggagagc ttcacagtgc agcggcgagt ccaacctaag       60
gtgactgtat atccttcaaa gacccagccc ctgcagcacc                            100

<210> SEQ ID NO 65
<211> LENGTH: 75
<212> TYPE: DNA
<213> ORGANISM: Artificial sequence
<220> FEATURE:
<223> OTHER INFORMATION: synthetic construct

<400> SEQUENCE: 65
gcactgtgaa gctctccaca accccgtagt tgtgtctgca ctaggacgca aatcacttga       60
agaagtgaaa gcgag                                                        75

<210> SEQ ID NO 66
<211> LENGTH: 65
<212> TYPE: DNA
<213> ORGANISM: Artificial sequence
<220> FEATURE:
<223> OTHER INFORMATION: synthetic construct

<400> SEQUENCE: 66
cgaaagccat gacctccgat cactctttga aggatataca gtcaccttag gttggactcg       60
ccgct                                                                   65

<210> SEQ ID NO 67
<211> LENGTH: 100
<212> TYPE: DNA
<213> ORGANISM: Homo sapiens

<400> SEQUENCE: 67
ttcctacatg gcaaagctga cagtgacact gatggtgctg agctccccac tggctttggc       60
tggggacacc cgaccacgtt tcttgcagca ggataagtat                            100

<210> SEQ ID NO 68
<211> LENGTH: 85
<212> TYPE: DNA
<213> ORGANISM: Artificial sequence
<220> FEATURE:
<223> OTHER INFORMATION: synthetic construct

<400> SEQUENCE: 68
gtggggagct cagcaccatc agtgtcactg tcagctttgc catgtaggaa ccacgcgatg       60
acgttcgtca agagtcgcat aatct                                             85

<210> SEQ ID NO 69
<211> LENGTH: 75
<212> TYPE: DNA
<213> ORGANISM: Artificial sequence
<220> FEATURE:

<223> OTHER INFORMATION: synthetic construct

<400> SEQUENCE: 69
cgaaagccat gacctccgat cactcatact tatcctgctg caagaaacgt ggtcgggtgt    60
ccccagccaa agcca    75

<210> SEQ ID NO 70
<211> LENGTH: 100
<212> TYPE: DNA
<213> ORGANISM: Homo sapiens

<400> SEQUENCE: 70
atactatcca gttactgccg gtttgaaaat atgcctgcaa tctgagccag tgctttaatg    60
gcatgtcaga cagaacttga atgtgtcagg tgaccctgat    100

<210> SEQ ID NO 71
<211> LENGTH: 85
<212> TYPE: DNA
<213> ORGANISM: Artificial sequence
<220> FEATURE:
<223> OTHER INFORMATION: synthetic construct

<400> SEQUENCE: 71
ctggctcaga ttgcaggcat attttcaaac cggcagtaac tggatagtat catttggaat    60
gatgtgtact gggaataaga cgacg    85

<210> SEQ ID NO 72
<211> LENGTH: 75
<212> TYPE: DNA
<213> ORGANISM: Artificial sequence
<220> FEATURE:
<223> OTHER INFORMATION: synthetic construct

<400> SEQUENCE: 72
cgaaagccat gacctccgat cactcatcag ggtcacctga cacattcaag ttctgtctga    60
catgccatta aagca    75

<210> SEQ ID NO 73
<211> LENGTH: 100
<212> TYPE: DNA
<213> ORGANISM: Homo sapiens

<400> SEQUENCE: 73
ttgctttgac cactcttcct gagttcagtg gcactcaaca tgagtcaaga gcatcctgct    60
tctaccatgt ggatttggtc acaaggttta aggtgaccca    100

<210> SEQ ID NO 74
<211> LENGTH: 85
<212> TYPE: DNA
<213> ORGANISM: Artificial sequence
<220> FEATURE:
<223> OTHER INFORMATION: synthetic construct

<400> SEQUENCE: 74
tcttgactca tgttgagtgc cactgaactc aggaagagtg gtcaaagcaa cacaagaatc    60
cctgctagct gaaggagggt caaac    85

<210> SEQ ID NO 75
<211> LENGTH: 75
<212> TYPE: DNA
<213> ORGANISM: Artificial sequence

```
<220> FEATURE:
<223> OTHER INFORMATION: synthetic construct

<400> SEQUENCE: 75
cgaaagccat gacctccgat cactctgggt caccttaaac cttgtgacca aatccacatg    60
gtagaagcag gatgc                                                     75

<210> SEQ ID NO 76
<211> LENGTH: 100
<212> TYPE: DNA
<213> ORGANISM: Homo sapiens

<400> SEQUENCE: 76
agcagatgta gagggagaac tcttagcgtg caggaatcta atgccatcag caggcaaagc    60
catgcacacg cctaaaccat cagtaggtga agagaaagac                          100

<210> SEQ ID NO 77
<211> LENGTH: 83
<212> TYPE: DNA
<213> ORGANISM: Artificial sequence
<220> FEATURE:
<223> OTHER INFORMATION: synthetic construct

<400> SEQUENCE: 77
ctgatggcat tagattcctg cacgctaaga gttctccctc tacatctgct tgacgtagat    60
tgctatcagg ttacgatgac tgc                                            83

<210> SEQ ID NO 78
<211> LENGTH: 75
<212> TYPE: DNA
<213> ORGANISM: Artificial sequence
<220> FEATURE:
<223> OTHER INFORMATION: synthetic construct

<400> SEQUENCE: 78
cgaaagccat gacctccgat cactcgtctt tctcttcacc tactgatggt ttaggcgtgt    60
gcatggcttt gcctg                                                     75

<210> SEQ ID NO 79
<211> LENGTH: 100
<212> TYPE: DNA
<213> ORGANISM: Homo sapiens

<400> SEQUENCE: 79
ggaagtattc ttcgtgttac tacagctgac ccatatgcca gtggaaaaat cagccagttt    60
ctggggattt gcattcagag atcaggaaga ggacttggag                          100

<210> SEQ ID NO 80
<211> LENGTH: 85
<212> TYPE: DNA
<213> ORGANISM: Artificial sequence
<220> FEATURE:
<223> OTHER INFORMATION: synthetic construct

<400> SEQUENCE: 80 attttccac tggcatatgg gtcagctgta gtaacacgaa gaatacttcc cttacagatc     60
gtgtgctcat gacttccaca gacgt                                          85

<210> SEQ ID NO 81
<211> LENGTH: 73
<212> TYPE: DNA
```

<213> ORGANISM: Artificial sequence
<220> FEATURE:
<223> OTHER INFORMATION: synthetic construct

<400> SEQUENCE: 81
cgaaagccat gacctccgat cactcccaag tcctcttcct gatctctgaa tgcaaatccc   60
cagaaactgg ctg                                                      73

<210> SEQ ID NO 82
<211> LENGTH: 100
<212> TYPE: DNA
<213> ORGANISM: Homo sapiens

<400> SEQUENCE: 82
cctccagccc ctcctataga ttcatattga atgatgggac aatgcttagc gcccacacca   60
agtgtaaact ttgctaccct caaagtccag acatgcaacc                        100

<210> SEQ ID NO 83
<211> LENGTH: 85
<212> TYPE: DNA
<213> ORGANISM: Artificial sequence
<220> FEATURE:
<223> OTHER INFORMATION: synthetic construct

<400> SEQUENCE: 83
gctaagcatt gtcccatcat tcaatatgaa tctataggag gggctggagg cttggaggag   60
ttgatagtgg taaaacaaca ttagc                                         85

<210> SEQ ID NO 84
<211> LENGTH: 75
<212> TYPE: DNA
<213> ORGANISM: Artificial sequence
<220> FEATURE:
<223> OTHER INFORMATION: synthetic construct

<400> SEQUENCE: 84
cgaaagccat gacctccgat cactcggttg catgtctgga ctttgagggt agcaaagttt   60
acacttggtg tgggc                                                    75

<210> SEQ ID NO 85
<211> LENGTH: 100
<212> TYPE: DNA
<213> ORGANISM: Homo sapiens

<400> SEQUENCE: 85
tagaagcagt gaacatggct tcaaagatac taaaaagcta tgagtccagt cttccccaga   60
cacagcaagt ggatcttgac ttatccaggc cacttttcac                        100

<210> SEQ ID NO 86
<211> LENGTH: 85
<212> TYPE: DNA
<213> ORGANISM: Artificial sequence
<220> FEATURE:
<223> OTHER INFORMATION: synthetic construct

<400> SEQUENCE: 86
actggactca tagctttta gtatctttga agccatgttc actgcttcta cctacgtata    60
tatccaagtg gttatgtccg acggc                                         85

<210> SEQ ID NO 87
<211> LENGTH: 75

<212> TYPE: DNA
<213> ORGANISM: Artificial sequence
<220> FEATURE:
<223> OTHER INFORMATION: synthetic construct

<400> SEQUENCE: 87
cgaaagccat gacctccgat cactcgtgaa aagtggcctg gataagtcaa gatccacttg    60
ctgtgtctgg ggaag                                                    75

<210> SEQ ID NO 88
<211> LENGTH: 100
<212> TYPE: DNA
<213> ORGANISM: Homo sapiens

<400> SEQUENCE: 88
cttccccgag gaccgcagcc agcccggcca ggactgccgc ttccgtgtca cacaactgcc    60
caacgggcgt gacttccaca tgagcgtggt cagggcccgg                         100

<210> SEQ ID NO 89
<211> LENGTH: 70
<212> TYPE: DNA
<213> ORGANISM: Artificial sequence
<220> FEATURE:
<223> OTHER INFORMATION: synthetic construct

<400> SEQUENCE: 89
tgacacggaa gcggcagtcc tggccgggct ggctgcagca agaaggagta tggaacttat    60
agcaagagag                                                          70

<210> SEQ ID NO 90
<211> LENGTH: 68
<212> TYPE: DNA
<213> ORGANISM: Artificial sequence
<220> FEATURE:
<223> OTHER INFORMATION: synthetic construct

<400> SEQUENCE: 90
cgaaagccat gacctccgat cactcctgac cacgctcatg tggaagtcac gcccgttggg    60
cagttgtg                                                            68

<210> SEQ ID NO 91
<211> LENGTH: 100
<212> TYPE: DNA
<213> ORGANISM: Homo sapiens

<400> SEQUENCE: 91
agccagccag agcccacaat acagcttcga gtcattacct cagaagattt gtttaatctg    60
tggggatgaa gcatcaggct gtcattatgg tgtccttacc                         100

<210> SEQ ID NO 92
<211> LENGTH: 85
<212> TYPE: DNA
<213> ORGANISM: Artificial sequence
<220> FEATURE:
<223> OTHER INFORMATION: synthetic construct

<400> SEQUENCE: 92
aaatcttctg aggtaatgac tcgaagctgt attgtgggct ctggctggct caccccctcca   60 aacgcattct tattggcaaa tggaa                                         85

<210> SEQ ID NO 93

<211> LENGTH: 75
<212> TYPE: DNA
<213> ORGANISM: Artificial sequence
<220> FEATURE:
<223> OTHER INFORMATION: synthetic construct

<400> SEQUENCE: 93
cgaaagccat gacctccgat cactcggtaa ggacaccata atgacagcct gatgcttcat    60
ccccacagat taaac    75

<210> SEQ ID NO 94
<211> LENGTH: 100
<212> TYPE: DNA
<213> ORGANISM: Homo sapiens

<400> SEQUENCE: 94
catcggacaa tttctggagg ctgtggatca gaatacagcc atcgtgggct ctaccacagg    60
ctccaactat tatgtgcgca tcctgagcac catcgatcgg    100

<210> SEQ ID NO 95
<211> LENGTH: 85
<212> TYPE: DNA
<213> ORGANISM: Artificial sequence
<220> FEATURE:
<223> OTHER INFORMATION: synthetic construct

<400> SEQUENCE: 95
agcccacgat ggctgtattc tgatccacag cctccagaaa ttgtccgatg cccgaagcaa    60
tactgtcgtc actctgtatg tccgt    85

<210> SEQ ID NO 96
<211> LENGTH: 75
<212> TYPE: DNA
<213> ORGANISM: Artificial sequence
<220> FEATURE:
<223> OTHER INFORMATION: synthetic construct

<400> SEQUENCE: 96
cgaaagccat gacctccgat cactcccgat cgatggtgct caggatgcgc acataatagt    60
tggagcctgt ggtag    75

<210> SEQ ID NO 97
<211> LENGTH: 100
<212> TYPE: DNA
<213> ORGANISM: Homo sapiens

<400> SEQUENCE: 97
cgaaatgttt cattgtggga gcagacaatg tgggctccaa gcagatgcag cagatccgca    60
tgtcccttcg cgggaaggct gtggtgctga tgggcaagaa    100

<210> SEQ ID NO 98
<211> LENGTH: 85
<212> TYPE: DNA
<213> ORGANISM: Artificial sequence
<220> FEATURE:
<223> OTHER INFORMATION: synthetic construct

<400> SEQUENCE: 98
ctgcatctgc ttggagccca cattgtctgc tcccacaatg aaacatttcg ccgggaatcg    60
gcatttcgca ttcttaggat ctaaa    85

```
<210> SEQ ID NO 99
<211> LENGTH: 61
<212> TYPE: DNA
<213> ORGANISM: Artificial sequence
<220> FEATURE:
<223> OTHER INFORMATION: synthetic construct

<400> SEQUENCE: 99
cgaaagccat gacctccgat cactccacca cagccttccc gcgaagggac atgcggatct    60
g                                                                   61

<210> SEQ ID NO 100
<211> LENGTH: 100
<212> TYPE: DNA
<213> ORGANISM: Homo sapiens

<400> SEQUENCE: 100
cttctaagcc agttgtgggg attatttacc ctcctccaga ggtcagaaat attgttgaca    60
agactgccag ctttgtggcc agaaacgggc tgaatttga                          100

<210> SEQ ID NO 101
<211> LENGTH: 85
<212> TYPE: DNA
<213> ORGANISM: Artificial sequence
<220> FEATURE:
<223> OTHER INFORMATION: synthetic construct

<400> SEQUENCE: 101
atttctgacc tctggaggag ggtaaataat ccccacaact ggcttagaag ccgatcttca    60
taacggacaa actgaacggg ccatt                                         85

<210> SEQ ID NO 102
<211> LENGTH: 75
<212> TYPE: DNA
<213> ORGANISM: Artificial sequence
<220> FEATURE:
<223> OTHER INFORMATION: synthetic construct

<400> SEQUENCE: 102
cgaaagccat gacctccgat cactctcaaa ttcaggcccg tttctggcca caaagctggc    60
agtcttgtca acaat                                                    75

<210> SEQ ID NO 103
<211> LENGTH: 100
<212> TYPE: DNA
<213> ORGANISM: Homo sapiens

<400> SEQUENCE: 103
caagtggagc accccagcct ggacagtcct gtcaccgtgg agtggaaggc acagtctgat    60
tctgtgcaga gcaagatgct gacaggagct aggggcttca                        100

<210> SEQ ID NO 104
<211> LENGTH: 71
<212> TYPE: DNA
<213> ORGANISM: Artificial sequence
<220> FEATURE:
<223> OTHER INFORMATION: synthetic construct

<400> SEQUENCE: 104
gccttccact ccacggtgac aggactgtcc aggctgcgct atgcagacga gctggcagag    60
gagagaaatc a                                                        71
```

```
<210> SEQ ID NO 105
<211> LENGTH: 75
<212> TYPE: DNA
<213> ORGANISM: Artificial sequence
<220> FEATURE:
<223> OTHER INFORMATION: synthetic construct

<400> SEQUENCE: 105
cgaaagccat gacctccgat cactctgaag cccctagctc ctgtcagcat cttgctctgc    60
acagaatcag actgt                                                    75

<210> SEQ ID NO 106
<211> LENGTH: 100
<212> TYPE: DNA
<213> ORGANISM: Homo sapiens

<400> SEQUENCE: 106
tgcagtacct gaacagatac atccataaac gggaggagaa cctgcgcttc gacagcaacg    60
tggaggagtt ccaggcagtt acggaactgg ggcggcctgt                        100

<210> SEQ ID NO 107
<211> LENGTH: 77
<212> TYPE: DNA
<213> ORGANISM: Artificial sequence
<220> FEATURE:
<223> OTHER INFORMATION: synthetic construct

<400> SEQUENCE: 107
gaagcgcagg ttctcctccc gtttatggat gtatctgttc agcattcgca accatgtgaa    60
gtaatgtgag cgtactt                                                  77

<210> SEQ ID NO 108
<211> LENGTH: 63
<212> TYPE: DNA
<213> ORGANISM: Artificial sequence
<220> FEATURE:
<223> OTHER INFORMATION: synthetic construct

<400> SEQUENCE: 108
cgaaagccat gacctccgat cactcagttc cgtaactgcc tggaactcct ccacgttgct    60
gtc                                                                 63
```

MULTIGENE ASSAY TO ASSESS RISK OF RECURRENCE OF CANCER

CROSS-REFERENCE TO RELATED APPLICATION(S)

This application is a U.S. national stage entry of International Patent Application No. PCT/US2020/026727, filed on Apr. 3, 2020, which claims priority to U.S. Provisional Patent Application No. 62/829,440, filed on Apr. 4, 2019, the entire contents of each of which are fully incorporated herein by reference.

STATEMENT REGARDING FEDERALLY SPONSORED RESEARCH

This invention was made with government support under grant P30CA042014, grant KL2TR001996, and grant P30CA177558 awarded by the National Institutes of Health. The government has certain rights in the invention.

REFERENCE TO SEQUENCE LISTING

This application was filed with a Sequence Listing XML in ST.26 XML format accordance with 37 C.F.R. § 1.831. The Sequence Listing XML file submitted in the USPTO Patent Center, "026389-9247-US02_sequence_listing_xml_11-APR-2025.xml, " was created on Apr. 11, 2025, contains 108 sequences, has a file of 104.0 kilobytes (106,496 bytes), and is incorporated by reference in its entirety into the specification.

FIELD

This disclosure relates to specific biomarkers and methods of using the same for determining the risk of recurrence of cancer.

INTRODUCTION

Triple negative breast cancer (TNBC) is a clinical subtype of invasive breast cancer that is defined by the absence of standard markers used for prognosis and treatment decisions in breast cancer (Estrogen receptor (ER), Progesterone receptor (PR), and HER2). TNBC is notable for aggressive behavior and high rates of local and distant recurrence. TNBC patients are conventionally treated with local therapy and cytotoxic chemotherapy. Patient outcomes are disparate. Approximately 42% of patients experience rapid relapses with a peak at three years from diagnosis, while the remaining 58% of patients have long-term disease free survival (DFS). Physicians cannot currently predict which patients will relapse despite intensive chemotherapy, and which patients will have long-term disease-free survival and may do equally well with de-escalation of their chemotherapy regimen. Currently, most TNBC patients are treated with aggressive chemotherapy, which can result in serious long-term toxicity including permanent peripheral neuropathy, cardiac toxicity, and secondary malignancies. There is a critical need for prognostic and predictive biomarker tests that can enable precision medicine for patients with TNBC and other cancers, as well as tools to identify patients who do not require aggressive treatment and can be spared the associated toxicities.

SUMMARY

In an aspect, the disclosure relates to a method of determining the risk of recurrence of cancer in a subject. The method may include determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1; calculating a normalized expression level of each MHCII gene by multiplying the determined level of expression of each MHCII gene by the Normalization Factor for the subject; calculating a MHCII Score for the subject, wherein the MHCII Score is the geometric mean of the normalized expression levels of the MHCII genes; determining the level of expression in the subject of at least one TIL gene selected from CD3D, CD4, CD8A, CD69, IFNG, IL7R, PDCD1, CD274, and ARHGAP9; calculating a normalized expression level of each TIL gene by multiplying the determined level of expression of each TIL gene by the Normalization Factor for the subject; calculating a TIL Score for the subject, wherein the TIL Score is the geometric mean of the normalized expression levels of the TIL genes; determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

In some embodiments, the Housekeeping Control is the arithmetic mean of the Housekeeping Scores for a set of control samples, and wherein the control samples are from other subjects with cancer. In some embodiments, the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity. In some embodiments, the level of expression in the subject of each Housekeeping gene selected from ACTB, MRPL19, RPLP0, PSMC4, and SF3A1 is determined. In some embodiments, the level of expression of each MHCII gene is determined and the level of expression of each TIL gene is determined. In some embodiments, the level of expression of the genes is determined using a NanoString nCounter platform, and wherein the subject is determined to have an increased risk of cancer recurrence when the Immune Activation Score is less than a threshold value, and that the subject has a decreased risk of cancer recurrence when the Immune Activation Score is greater than or equal to the threshold value, wherein the threshold value is at least about 1750, at least about 2000, or at least about 2400. In some embodiments, the subject is determined to have a high risk of cancer recurrence when the Immune Activation Score is less than a first threshold value, and that the subject has a decreased risk of cancer recurrence when the Immune Activation Score is greater than or equal to the first threshold value and less than a second threshold value, and that the subject is determined to have a low risk of cancer recurrence when the Immune Activation Score is greater than or equal to the second threshold value. In some embodiments, the method further includes administering chemotherapy to the subject determined to have an increased risk or a high risk of cancer recurrence. In some embodiments, the method further includes abstaining from administering chemotherapy to the subject determined to have a decreased risk or a low risk of cancer recurrence. In some embodiments, the method further includes administering immunotherapy to the subject determined to have a decreased risk or a low risk of cancer recurrence.

In a further aspect, the disclosure relates to a method of diagnosing a subject with triple-negative breast cancer (TNBC) as having TNBC Basal-like subtype. The method may include determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one Basal-like gene selected from FOXC1, MKI67, CDC20, CCNE1, and ORC6; calculating a normalized expression level of each Basal-like gene by multiplying the determined level of expression of each Basal-like gene by the Normalization Factor for the subject; calculating a Basal-like Subtype Score for the subject, which is the geometric mean of the normalized expression levels of the Basal-like genes; determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score. In some embodiments, the control Basal-like Subtype Score is the arithmetic mean of Basal-like Subtype Scores for a set of samples from other subjects with breast cancer. In some embodiments, the level of expression of the genes is determined using a NanoString nCounter platform, and wherein the subject is determined to have TNBC Basal-like subtype when the Basal-like Subtype Score for the subject is greater than or equal to 350, and that the subject does not have TNBC Basal-like subtype when the Basal-like Subtype Score for the subject is less than 350. In some embodiments, the method further includes determining the risk of recurrence of cancer in the subject as detailed herein when the subject is determined to have TNBC Basal-like subtype.

Another aspect of the disclosure provides a method of treating cancer in a subject. The method may include determining an Immune Activation Score for the subject that is less than a control Immune Activation Score as detailed herein; and administering chemotherapy to the subject determined to have an increased risk of cancer recurrence. The method may include determining an Immune Activation Score for the subject that is greater than or equal to a control Immune Activation Score as detailed herein; and administering immunotherapy to the subject determined to have a decreased risk of cancer recurrence.

Another aspect of the disclosure provides a method of diagnosing a subject with triple-negative breast cancer (TNBC) as having TNBC Basal-like subtype and determining the risk of recurrence of cancer in the subject. The method may include determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one Basal-like gene selected from FOXC1, MKI67, CDC20, CCNE1, and ORC6; calculating a normalized expression level of each Basal-like gene by multiplying the determined level of expression of each Basal-like gene by the Normalization Factor for the subject; calculating a Basal-like Subtype Score for the subject, which is the geometric mean of the normalized expression levels of the Basal-like genes; determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score; determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1; calculating a normalized expression level of each MHCII gene by multiplying the determined level of expression of each MHCII gene by the Normalization Factor for the subject; calculating a MHCII Score for the subject, wherein the MHCII Score is the geometric mean of the normalized expression levels of the MHCII genes; determining the level of expression in the subject of at least one TIL gene selected from CD3D, CD4, CD8A, CD69, IFNG, IL7R, PDCD1, CD274, and ARHGAP9; calculating a normalized expression level of each TIL gene by multiplying the determined level of expression of each TIL gene by the Normalization Factor for the subject; calculating a TIL Score for the subject, wherein the TIL Score is the geometric mean of the normalized expression levels of the TIL genes; determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score. In some embodiments, the control Basal-like Subtype Score is the arithmetic mean of Basal-like Subtype Scores for a set samples from other subjects with breast cancer. In some embodiments, the Housekeeping Control is the arithmetic mean of the Housekeeping Scores for a set of control samples, and wherein the control samples are from other subjects with cancer. In some embodiments, the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity.

In some embodiments, the level of expression for the gene is determined by measuring the level of RNA. In some embodiments, the level of RNA is measured using a NanoString nCounter platform. In some embodiments, the level of expression in a sample from the subject is determined. In some embodiments, the sample comprises tissue or blood. In some embodiments, the sample comprises tumor tissue. In some embodiments, the cancer comprises breast cancer, ovarian cancer, bladder cancer, or lung cancer. In some embodiments, the breast cancer is triple-negative breast cancer (TNBC). In some embodiments, the breast cancer is HER2-enriched breast cancer. In some embodiments, the lung cancer is squamous cell lung cancer.

The disclosure provides for other aspects and embodiments that will be apparent in light of the following detailed description and accompanying figures.

BRIEF DESCRIPTION OF THE DRAWINGS

(FIG. 1A) Gene sets measured by the assay. (FIG. 1B) The assay provided similar measurements of gene expression in Frozen and FFPE sections from the same tumor (n=3). Each point in the scatter-plot represents the expression values for one of 36 genes. (FIG. 1C) The assay provided highly similar gene expression measurements between two replicates of each of 11 different FFPE breast tumor RNA samples. Each point in the scatter-plot represents the expression values for one of 36 genes in one of 11 samples. Each of the 11 samples is depicted in a different color. (FIG. 1D) The TIL genes in the assay were differentially expressed between histologically confirmed TIL high and TIL low TNBC tumors. (FIG. 1E) The Subtype Verification genes in the MHCII Immune Activation assay were differentially expressed between FFPE tumor specimens previously classified by the PAM50 assay as Basal-like (n=8), Luminal A (n=8), Luminal B (n=8), and HER2-enriched (n=9). (FIG. 1F) A threshold chosen for the Basal-like score distinguishes Basal-like tumors from other subtypes.

(FIG. 2A) MHCII gene expression measurements from the MHCII Immune Activation assay and RNA-seq on the same TNBC tumor samples were highly correlated. Each of the 10 genes is a different color. (FIG. 2B) MHCII Scores were significantly higher in patients who did not relapse. Mean and 95% confidence interval shown. Threshold is a dashed line, red circle classified as high, blue circle classified as low. (FIG. 2C) A Kaplan Meier curve and log rank p-value show significantly longer DFS in patients with high MHCII Scores. (FIG. 2D) Expression of MHCII and TIL genes are highly correlated within TNBC patient tumors in the training set. (FIG. 2E) Immune Activation Scores calculated using MHCII and TIL genes were significantly higher in patients who did not relapse. Mean and 95% confidence interval shown. Threshold is dashed line, red circles classified as high, blue circles classified as low. (FIG. 2F) A Kaplan Meier curve and log rank p-value show significantly longer DFS in patients with high Immune Activation Scores using the threshold depicted in E.

(FIG. 3A) Expression of MHCII and TIL genes are highly correlated within TNBC patient tumors in the independent validation cohort. (FIG. 3B) Immune Activation Scores calculated using MHCII and TIL genes in the MHCII Immune Activation assay were significantly higher in patients who did not relapse. Mean and 95% confidence interval shown. Threshold is a dashed line, red circle classified as high, blue circle classified as low. (FIG. 3C) A Kaplan Meier curve and log rank p-value show significantly longer DFS in patients with high Immune Activation Scores using the threshold depicted in FIG. 3B.

(FIG. 4A) ROC curve analysis of the training set was used to select an Immune Activation Score threshold that results in 95% specificity for identifying patients who do not relapse. Training set ROC curve in green. Validation cohort ROC curve in orange. 95% confidence intervals for the threshold that provides 95% specificity in Training set shown as black error bars. (FIG. 4B) When this Immune Activation Score threshold was applied to the independent validation cohort, the specificity for identifying patients who did not relapse was 100%. (FIG. 4C) Kaplan Meier curve that stratifies patients in the training set based on the Immune Activation Score threshold that provides 95% specificity. (FIG. 4D) Kaplan Meier curve of the same threshold applied to the independent validation cohort demonstrates longer DFS in patients with Immune Activation Scores above the threshold. (FIG. 4E) Risk of recurrence can be modeled as a linear function of the logo Immune Activation score in both the training set and validation cohort.

(FIG. 5A) Immunohistochemical analysis of MHCII expression in patients with high, intermediate, and low Immune Activation Scores. (FIG. 5B) The TIL Score calculated from TIL gene expression using the MHCII Immune Activation assay is correlated with histologic assessment of stromal TIL percentage.

(FIG. 9A) In the training set, the MHCII gene expression measurements from the MHCII Immune Activation assay on the NanoString platform and RNA-seq data from the same TNBC tumors were correlated, except for three gene probes (HLA-DRB6, HLA-DRB5, HLA-DQA1) that were excluded from further analysis due to their lack of concordance. (FIG. 9B) The same three gene probes were also poorly with CIITA, the master regulator of these genes, in the validation cohort. The observation that they exhibited similar patterns of technical variation in both the training set and the validation cohort indicates the anomalous gene expression measurements for these probes is not specific to samples in the cohort nor the instrument runs.

FIG. 11A, FIG. 11B. ROC curve statistics using the Immune Activation score threshold that provides 95% specificity in the training set are depicted for the training set (FIG. 11A) and validation cohort (FIG. 11B).

(FIG. 12A) Kaplan Meier plot stratifying patients in the training and validation cohorts based on Immune Activation (IA) score and whether they received chemotherapy. Patients with High Immune Activation scores who did not receive chemotherapy did not relapse (red line, top). (FIG. 12B) Kaplan Meier plot of public microarray data from patients who did not receive systemic chemotherapy. Patients with high expression of MHCII and TIL genes have significantly longer disease-free survival compared to patients with low expression of genes in the signature.

DETAILED DESCRIPTION

Figure 1A:
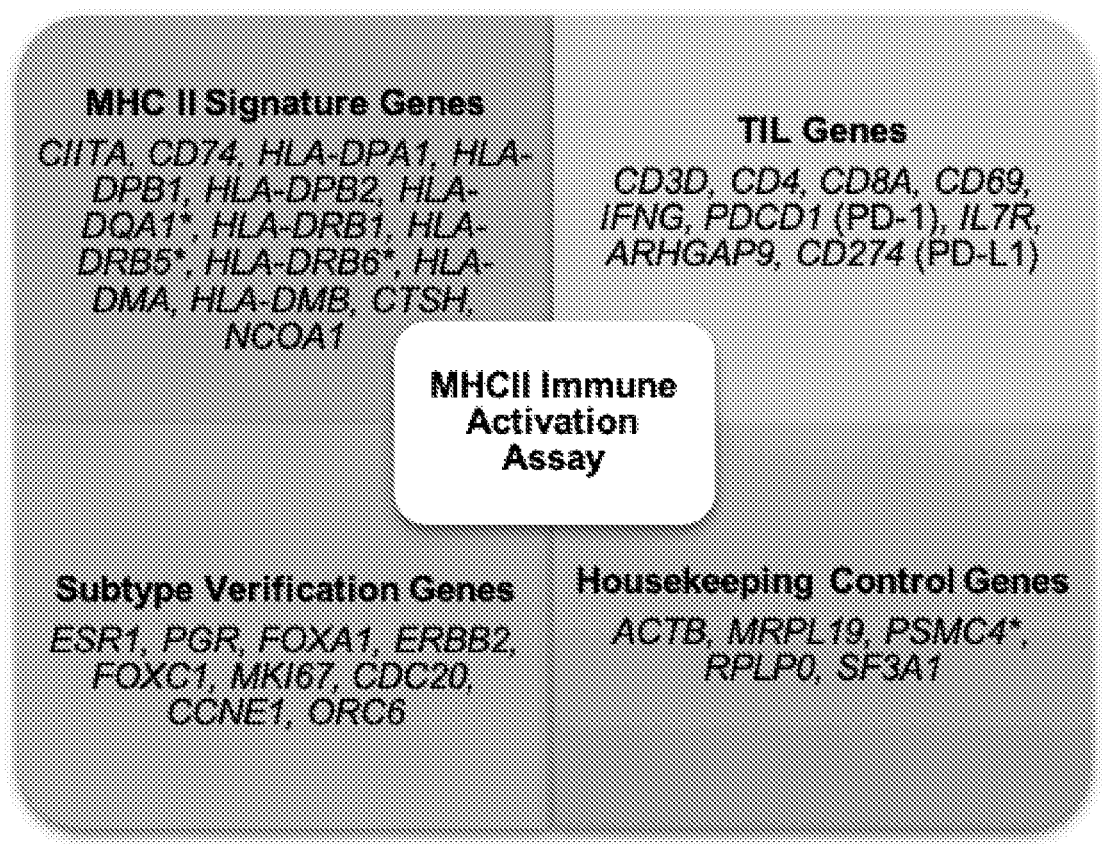
FIG. 1A, FIG. 1B, FIG. 1C, FIG. 1D, FIG. 1E, FIG. 1F. Pre-analytical testing of the MHCII Immune Activation assay.

Described herein are assays and methods for identifying cancer patients with a low risk of recurrence, independent of clinical variables. The assays and methods address a critical need for prognostic biomarker tests that enable precision medicine for cancer patients. Further detailed herein are methods of diagnosing a subject with triple-negative breast cancer (TNBC) as having TNBC Basal-like subtype.

Expression of the major histocompatibility complex Class II antigen presentation pathway (MHCII) in TNBC tumor cells is associated with long-term disease-free survival (DFS). High MHCII expression in tumor cells is associated with the presence of tumor-infiltrating lymphocytes (TILs), which are associated with good prognosis in patients with triple negative breast cancer (TNBC). High expression of MHCII in tumor cells is associated with large amounts of tumor infiltrating CD4 and CD8 positive T cells, and longer DFS. Mouse studies have shown that MHCII expression on tumor cells triggers T cell recruitment and inhibits tumor progression.

Described herein is an assay that measures expression of at least 3 genes from a set of 19 MHCII and TIL genes, determines a MHCII Score and TIL Score, and determines an Immune Activation Score for a subject with cancer. The subject may have an increased risk of cancer recurrence when the Immune Activation Score for the subject is less than a control Immune Activation Score. The subject may have a decreased risk of cancer recurrence when the Immune Activation Score for the subject is greater than a control Immune Activation Score. Preanalytical testing confirmed that the assay is accurate and reproducible in formalin-fixed paraffin-embedded (FFPE) tumor specimens.

As further detailed herein, the assay measurements were concordant with RNA-seq, MHCII protein expression, and tumor infiltrating lymphocyte counts. In a training set of 44 primary TNBC tumors, the Immune Activation Score was significantly associated with longer DFS (HR=0.17, P=0.015), which confirmed the prognostic significance of this assay. In an independent validation cohort of 56 primary FFPE TNBC tumors, the Immune Activation Score was significantly associated with longer DFS (HR=0.19; P=0.011), independent of clinical stage. An Immune Activation Score threshold for identifying patients with very low risk of relapse in the training set provided 100% specificity in the validation cohort. The assay and methods detailed herein enable adoption of a standardized clinical prognostic test for identifying cancer patients, such as TNBC patients, with a low risk of recurrence. The assay and methods may also identify patients in whom chemotherapy can be safely de-escalated, and identify patients who are likely to respond to immunotherapy.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, "cancer" may include any cell or tissue derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state. Cancer may include solid/soft tumors such as breast, ovarian, bladder, and/or lung cancer. Cancer may include, for example, breast cancer, ovarian cancer, bladder cancer, and lung cancer. Breast cancer may include, for example, triple-negative breast cancer (TNBC), and HER2-enriched breast cancer. In some embodiments, breast cancer is defined by the "intrinsic" subtypes such as Basal-like or HER2-enriched breast cancer. TNBC may include Basal-like subtype. Lung cancer may include, for example, squamous cell lung cancer. Ovarian cancer may include high-grade serous carcinoma of the ovary. Bladder cancer may include, for example, bladder urothelial carcinoma.

"Chemotherapy" is defined herein as the treatment of cancer with one or more "chemotherapeutic agents." Chemotherapeutic agents are chemical molecules which act by killing cells that divide rapidly, one of the main properties of most cancer cells. Several categories of chemotherapeutic agents exist, such as, for example, alkylating agents, spindle poisons, mitotic inhibitors, cytotoxic/antitumor antibiotics, anti-metabolites, topoisomerase inhibitors, DNA methyltransferase inhibitors, and vascular disrupting agents. Spindle poisons may include, for example, mebendazole, and colchicine. Mitotic inhibitors may include, for example, taxanes (paclitaxel (Taxol®), docetaxel (Taxotere®), and vinca alkaloids (such as vincristine, vinblastine, vinorelbine, vindesine). Cytotoxic/antitumor antibiotics may include, for example, anthracyclines (such as doxorubicin, daunorubicin, adriamycine, idarubicin, epirubicin and mitoxantrone, valrubicin), and *Streptomyces* (such as actinomycin, bleomycin, mitomycin, plicamycin). Anti-metabolites may include, for example, pyrimidine analogues such as fluoropyrimidines analogs, 5-fluorouracil (5-FU), floxuridine (FUDR), Cytosine arabinoside (Cytarabine), Gemcitabine (Gemzar®), and capecitabine; purine analogues such as azathioprine, mercaptopurine, thioguanine, fludarabine, pentostatin, cladribine, capecitabine, and clofarabine; and folic acid analogues such as methotrexate, folic acid, pemetrexed, aminopterin, raltitrexed, trimethoprim, and pyrimethamine. Topoisomerase inhibitors may include, for example, camptothecins, irinotecan, topotecan, amsacrine, etoposide, etoposide phosphate, and teniposide. DNA methyltransferase inhibitors may include, for example, 2'-deoxy-5-azacytidine (DAC), 5-azacytidine, 5-aza-2'-deoxycytidine, 1-[beta]-D-arabinofuranosyl-5-azacytosine, and dihydro-5-azacytidine. Vascular disrupting agents may include, for example, flavone acetic acid derivatives, 5,6-dimethylxanthenone-4-acetic acid (DMXAA), and flavone acetic acid (FAA). Other chemotherapeutic drugs may include, for example, aprepitant, bortezomib (Velcade®, Millenium Pharmaceuticals), imatinib mesylate (Gleevec®), carmustine (BCNU), lomustine (CCNU), tamoxifen, gefitinib, erlotinib, carboxyamidotriazole, efaproxiral, tirapazamine, xcytrin, thymalfasin, and vinflunine. "Alkylating agents" are so named because of their ability to alkylate many molecules, including proteins, RNA, and DNA. This ability to bind covalently to DNA via their alkyl group is the primary cause for their anti-cancer effects, since it provokes cell apoptosis. Alkylating agents are cell cycle-independent drugs, and their effects are usually dose dependent. Subtypes of alkylating agents may include, for example, nitrogen mustards, nitrosoureas, tetrazines, aziridines, and non-classical alkylating agents. Nitrogen mustards may include, for example, mechlorethamine, cyclophosphamide, melphalan, chlorambucil, ifosfamide, and busulfan. Nitrosoureas may include, for example, N-Nitroso-N-methylurea (MNU), carmustine (BCNU), lomustine (CCNU) and semustine (MeCCNU), fotemustine, and streptozotocin. Tetrazines may include, for example, dacarbazine, mitozolomide, and temozolomide. Aziridines may include, for example, thiotepa, mytomycin, and diaziquone (AZQ). Non-classical alkylating agents may include, for example, procarbazine and hexamethylmelamine. Alkylating-like agents may include platinum-based chemotherapeutic drugs (also termed "platinum analogues") that act in a similar manner as alkylating agents, they may permanently coordinate to DNA to interfere with DNA repair, and they may include, for example, platinum, cisplatin, carboplatin, nedaplatin, oxaliplatin, satraplatin, and triplatin tetranitrate. Chemotherapies may be combined or co-administered. In some embodiments, chemotherapy includes a combination or co-administration of docetaxel and carboplatin. In some embodiments, chemotherapy includes a combination or co-administration of fluorouracil, epirubicin, and cyclophosphamide, followed by paclitaxel. Chemotherapy may be neoadjuvant. Neoadjuvant therapy is the administration of a therapy or therapeutic agents before a main treatment. For example, neoadjuvant chemotherapy may include chemotherapy that is administered prior to surgery therapy or surgical resection of the cancer or tumor. In some embodiments, neoadjuvant chemotherapy may include chemotherapy that is administered prior to immunotherapy. In some embodiments, chemotherapy is combined or co-administered with immunotherapy.

The term "co-administration" generally refers to the administration of at least two different substances sufficiently close in time. Co-administration refers to simultaneous administration, as well as temporally spaced order of up to several hours or days apart, of at least two different substances in any order, either in a single dose or separate doses. In some embodiments, at least two different therapies may be administered in a combined formulation, referring to a mixture of two or more isolated pharmaceutical compositions into a single dosage form.

"Immunotherapy" is defined herein as the treatment of cancer by activating or suppressing the immune system. Cancer immunotherapy may stimulate the immune system to destroy tumors. Cell-based immunotherapies may be effective for some cancers. Immune effector cells such as lymphocytes, macrophages, dendritic cells, natural killer cells (NK Cell), cytotoxic T lymphocytes (CTL), etc., may work together to defend the body against cancer by targeting abnormal antigens expressed on the surface of tumor cells. Immunotherapy may include immune checkpoint inhibitors such as those that interrupt CTLA4 and/or PD-1/PD-L1 pathways, including, for example, pembrolizumab, nivolumab, cemiplimab, atezolizumab, avelumab, durvalumab, and ipilimumab.

"Gene expression" describes the conversion of the DNA gene sequence information into transcribed RNA (the initial unspliced RNA transcript or the mature mRNA) or the encoded protein product. The expression level of a gene may refer to an amount or a concentration of a transcription product, such as mRNA, or of a translation product, such as a protein or polypeptide. Gene expression can be monitored by, for example, measuring the levels of either the entire RNA or protein products of the gene or their subsequences.

"Probe" refers to a nucleic acid sequence designed to hybridize specifically to a target sequence of interest.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC). The healthy or normal levels or ranges for a target or for a protein activity or for a gene expression level may be defined in accordance with standard practice. A control may be a subject, or a sample therefrom, whose disease state is known. A control may be a subject or sample with or without cancer. The subject, or sample therefrom, may be at any stage of cancer. The subject, or sample therefrom, may be healthy, diseased, diseased prior to treatment, diseased during treatment, or diseased after treatment, or a combination thereof.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribonucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. A domain may be comprised of a series of the same type of motif.

"Sample" or "test sample" as used herein can mean any sample in which the presence and/or level of a target or gene is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" as used herein can mean a mammal that wants or is in need of the herein described assays or methods. The subject may be a patient. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. The subject may be male or female. In some embodiments, the subject has a specific genetic marker.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

A "therapeutically effective amount" or "effective amount" as used interchangeably herein is an amount sufficient to elicit a therapeutic effect. Amounts effective for this use will depend on, e.g., the particular composition of the regimen administered, the manner of administration, the stage and severity of the disease, the general state of health of the subject, and the judgment of the prescribing physician. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

"Treatment" or "treating," when referring to protection of a subject from a disease, means suppressing, repressing, ameliorating, or completely eliminating the disease. Preventing the disease involves administering a composition of the present invention to a subject prior to onset of the disease. Suppressing the disease involves administering a composition of the present invention to a subject after induction of the disease but before its clinical appearance. Repressing or ameliorating the disease involves administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequence substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. GENE EXPRESSION LEVELS

The level of expression of a gene in a subject or sample therefrom may be determined by any suitable method known in the art. The level of expression of a gene may be assessed by measuring the RNA expression level. The expression level of a gene may be determined in relation to various features of the expression products of the gene including, for example, exons, introns, protein epitopes, and protein activity. The level of expression of a gene may be determined using a method based on hybridization analysis of polynucleotides. The level of expression of a gene may be determined using a method based on sequencing of polynucleotides. The level of expression of a gene may be determined by measuring the level of RNA. The level of RNA may be measured by any suitable method known in the art. Gene expression levels can be monitored by assaying a subject's mRNA using a method or process that detects a signal coming from the mRNA molecules. Examples of methods or processes used to determine gene expression levels may include, for example, nucleic acid hybridization, Northern blotting, in situ hybridization, RNAse protection assays, microarrays, RNA sequencing (RNAseq), quantitative polymerase chain reaction (or other nucleic acid replication reactions), a NanoString nCounter platform, reverse transcription polymerase chain reaction (RT-PCR), sequencing such as nucleic acid sequencing, ligase chain reaction (LCR), multiplex ligation-dependent probe amplification, transcription-mediated amplification (TMA), strand displacement amplification (SDA), nucleic acid sequence based amplification (NASBA), protein product detection, and visible light or ultra-violet light spectrophotometry or diffraction, or a combination thereof. Such methods can utilize fluorescent dyes, chemiluminescent dyes, radioactive tracers, enzymatic reporters, dye molecules, chemical reaction products, or other means of reporting the amounts or concentrations of nucleic acid molecules or peptides. Oligonucleotide probes may be used to detect the presence of complementary target sequences by hybridization with the target sequences. Gene expression levels can be monitored by first reverse transcribing the mRNA from a subject's sample to produce cDNA, then amplifying the cDNA using the polymerase chain reaction (PCR). Antibodies may be employed that can recognize specific duplexes, including DNA duplexes, RNA duplexes, and DNA-RNA hybrid duplexes or DNA-protein duplexes. Methods for sequencing-based gene expression analysis may include Serial Analysis of Gene Expression (SAGE), and gene expression analysis by massively parallel signature sequencing (MPSS). The level of expression of a gene may be determined by measuring gene product or protein activity levels or proteomics techniques. Measuring the gene expression or quantity of protein in a biological sample may include electrophoretic and immunodiagnostic techniques, including immunoassays such as competition, direct reaction, sandwich type assays, Western blots, agglutination tests, enzyme-labeled and mediated immunoassays, such as ELISAs, biotin/avidin type assays, radioimmunoassays, immunoelectrophoresis, immunoprecipitation, and fluorescence-activated cell sorter (FACS). In some embodiments, the level of RNA is measured using PCR, RT-PCR, quantitative RT-PCR, microarray, RNA-seq, NanoString nCounter platform, RNA fluorescent in situ hybridization, or a combination thereof.

In some embodiments, the level of expression of the gene is determined using a NanoString nCounter platform (NanoString Technologies, Seattle, WA). In routine clinical practice, patients' tumors may be collected and processed as formalin-fixed, paraffin-embedded (FFPE) tissues, which can result in significant degradation of mRNA. PCR was the first technology used to demonstrate that small fragmented RNA transcripts could be recovered from FFPE tissue and used to accurately quantify gene expression in breast tumors. The NanoString nCounter platform is an alternative method for measuring gene expression in clinical FFPE specimens. NanoString nCounter technology is unique in that it measures RNA directly without amplification or cloning, which eliminates the biases that can be introduced by other PCR or sequencing-based methodologies.

a. Normalization Factor

The level of expression of a gene may be determined for a subject or a sample therefrom. The level of expression of the gene may be normalized. Normalization may correct for differences in signal intensity across trials or runs of a sample, correct for differences or variations in RNA template quality and quantity between samples, or a combination thereof.

Normalization may first include background subtraction. For example, in each Nanostring nCounter run a "no template" control sample may be analyzed, with the count values for each probe in the control subtracted from the count values for each of the samples in the run (this may be called "Blank lane background subtraction" in the NanoString nSolver analysis software).

Housekeeping genes may also be used to calculate normalized gene expression measurements for any genes measured. Housekeeping genes may include ACTB, MRPL19, RPLP0, PSMC4, and SF3A1. The level of expression of at least one Housekeeping gene selected from ACTB, MRPL19, RPLP0, PSMC4, and SF3A1, in the subject is determined. The level of 1, 2, 3, 4, or 5 Housekeeping genes may be determined. A Housekeeping Score for the subject is the geometric mean of the expression levels of the Housekeeping genes. The Housekeeping Score for the subject may be based on the level of 1, 2, 3, 4, or 5 Housekeeping genes. In some embodiments, the level of expression in the subject of each Housekeeping gene selected from ACTB, MRPL19, RPLP0, PSMC4, and SF3A1 is determined.

A Housekeeping Control is the arithmetic mean of the Housekeeping Scores for a set of control samples. The control samples may be, for example, from other subjects with cancer.

A Normalization Factor for the subject is the Housekeeping Control divided by the Housekeeping Score for the subject. A normalized expression level of a gene for the subject is calculated by multiplying the determined level of expression of the gene by the Normalization Factor for the subject.

3. RISK OF RECURRENCE

A risk of recurrence of cancer in a subject may be determined by calculating the Immune Activation Score for the subject. The Immune Activation Score is based on the MHCII Score and the TIL Score for the subject.

a. MHCII Score

The MHCII Score for a subject is based on the expression levels of MHCII genes. MHCII genes may include, for example, CIITA, CD74, HLA-DPA1, HLA-DPB1, HLA-DPB2, HLA-DRB1, HLA-DMA, HLA-DMB, CTSH, and NCOA1. The level of 1, 2, 3, 4, 5, 6, 7, 8, 9, or 10 MHCII genes may be determined. In some embodiments, the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1 is determined. In some embodiments, the level of expression of each MHCII gene selected from CIITA, CD74, HLA-DPA1, HLA-DPB1, HLA-DPB2, HLA-DRB1, HLA-DMA, HLA-DMB, CTSH, and NCOA1 is determined. A normalized expression level of each MHCII gene is calculated by multiplying the determined level of expression of each MHCII gene by the Normalization Factor for the subject. The MHCII Score is the geometric mean of the normalized expression levels of the MHCII genes.

b. TIL Score

The TIL Score for a subject is based on the expression levels of TIL genes. TIL genes may include, for example, CD3D, CD4, CD8A, CD69, IFNG, IL7R, PDCD1, CD274, and ARHGAP9. The level of 1, 2, 3, 4, 5, 6, 7, 8, or 9 TIL genes may be determined. In some embodiments, the level of expression in the subject of at least one TIL gene selected from CD3D, CD4, CD8A, CD69, IFNG, IL7R, PDCD1, CD274, and ARHGAP9 is determined. In some embodiments, the level of expression of each TIL gene selected from CD3D, CD4, CD8A, CD69, IFNG, IL7R, PDCD1, CD274, and ARHGAP9 is determined. A normalized expression level of each TIL gene is calculated by multiplying the determined level of expression of each TIL gene by the Normalization Factor for the subject. The TIL Score is the geometric mean of the normalized expression levels of the TIL genes.

c. Immune Activation Score

The Immune Activation Score for a subject is the geometric mean of the MHCII Score and the TIL Score for the subject. The Immune Activation Score is calculated using the normalized expression levels of at least three genes from the set of TIL genes and MHCII genes. For example, the Immune Activation Score may be calculated using a MHCII Score calculated from the normalized expression levels of at least one MHCII gene, and a TIL Score calculated from the normalized expression levels of at least two TIL genes. In some embodiments, the Immune Activation Score is calculated using a MHCII Score calculated from the normalized expression levels of at least two MHCII genes, and a TIL Score calculated from the normalized expression levels of at least one TIL gene.

A subject may be determined to have an increased risk of cancer recurrence when the Immune Activation Score is less than a threshold value, and the subject may be determined to have a decreased risk of cancer recurrence when the Immune Activation Score is greater than or equal to the threshold value. In some embodiments when the level of expression of the genes is determined using a NanoString nCounter platform, the threshold value is at least about 1750, at least about 2000, or at least about 2400. In some embodiments when the level of expression of the genes is determined using a NanoString nCounter platform, the threshold value is about 1750 with 90% specificity. In some embodiments when the level of expression of the genes is determined using a NanoString nCounter platform, the threshold value is about 2400 with 100% specificity.

When the Immune Activation Score for the subject is less than a control Immune Activation Score, the subject may have an increased risk of cancer recurrence. When the Immune Activation Score for the subject is greater than or equal to the control Immune Activation Score, the subject may have a decreased risk of cancer recurrence.

The control Immune Activation Score is determined from analysis of other subjects with cancer whose clinical outcomes and recurrence status is known. In some embodiments, the control Immune Activation Score is determined from analysis of at least 10 other subjects with cancer whose clinical outcomes and recurrence status is known. The Immune Activation Score for these subjects is calculated. An ROC curve analysis is performed to calculate the specificity and sensitivity of all possible Immune Activation Score thresholds for distinguishing between subjects who recur and those who do not. The Immune Activation Score threshold that provides the optimal sensitivity and specificity for distinguishing between subjects who recur and those who do not is selected as the control Immune Activation Score. In some embodiments, an Immune Activation Score threshold that provides at least 80% specificity and at least 5% sensitivity for identifying patients who do not recur is selected as the control Immune Activation Score. In some embodiments, an Immune Activation Score threshold that provides at least 90% specificity and at least 10% sensitivity for identifying patients who do not recur is selected as the control Immune Activation Score.

d. Methods of Determining the Risk of Recurrence of Cancer in a Subject

Provided herein are methods of determining the risk of recurrence of cancer in a subject. The method may include determining the Immune Activation Score for the subject, as detailed herein. The method may include determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1; calculating a normalized expression level of each MHCII gene by multiplying the determined level of expression of each MHCII gene by the Normalization Factor for the subject; calculating a MHCII Score for the subject, wherein the MHCII Score is the geometric mean of the normalized expression levels of the MHCII genes; determining the level of expression in the subject of at least one TIL gene selected from CD3D, CD4, CD8A, CD69, IFNG, IL7R, PDCD1, CD274, and ARHGAP9; calculating a normalized expression level of each TIL gene by multiplying the determined level of expression of each TIL gene by the Normalization Factor for the subject; calculating a TIL Score for the subject, wherein the TIL Score is the geometric mean of the normalized expression levels of the TIL genes; determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

In some embodiments, the method further includes administering chemotherapy to the subject determined to have an increased risk of cancer recurrence. In some embodiments, the method further includes abstaining from administering chemotherapy to the subject determined to have a decreased risk of cancer recurrence. In some embodiments, the method further includes administering immunotherapy to the subject determined to have a decreased risk of cancer recurrence.

4. TRIPLE-NEGATIVE BREAST CANCER (TNBC) BASAL-LIKE SUBTYPE

Triple-negative breast cancer (TNBC) is defined by lack of expression of estrogen receptor (ER) and of progesterone receptor (PR) and lack of amplification or overexpression of HER2. TNBC is an aggressive cancer associated with a high recurrence rate and short survival duration. TNBC is a clinical classification that encompasses several different molecular and gene expression subtypes. Basal-like subtype is a type of TNBC. Basal-like subtype is associated with increased invasiveness. The association between high Immune Activation Score and longer disease-free survival has been validated in TNBC patients with the Basal-like subtype. The Immune Activation assay includes subtype verification genes that are highly expressed in Basal-like TNBC tumors. These genes can be used to assess whether a TNBC patient's tumor is the Basal-like subtype.

Basal-like subtype may be diagnosed or distinguished in a subject by determining a Basal-like Subtype Score for the subject. The Basal-like Subtype Score for a subject is based on the expression levels of Basal-like genes. Basal-like genes include, for example, FOXC1, MKI67, CDC20, CCNE1, and ORC6. The level of 1, 2, 3, 4, or 5 Basal-like genes may be determined. In some embodiments, the level of expression in the subject of at least one Basal-like gene selected from FOXC1, MKI67, CDC20, CCNE1, and ORC6 is determined. In some embodiments, the level of expression in the subject of each Basal-like gene selected from FOXC1, MKI67, CDC20, CCNE1, and ORC6 is determined. A normalized expression level of the Basal-like gene is calculated by multiplying the determined level of expression of the Basal-like gene by the Normalization Factor for the subject. The Basal-like Subtype Score for the subject is the geometric mean of the normalized expression levels of the Basal-like genes.

A control Basal-like Subtype Score is determined from analysis of other subjects with breast cancer whose subtype is determined by other assays. In some embodiments, the control Basal-like Subtype Score is determined from analysis of at least 10 other subjects with breast cancer whose subtype is known and determined by other assays. The Basal-like Score for these subjects is calculated. An ROC curve analysis is performed to calculate the specificity and sensitivity of all possible Basal-like Score thresholds for distinguishing subjects with Basal-like breast cancer from subjects with other subtypes of breast cancer. The Basal-like score threshold that provides the optimal sensitivity and specificity for distinguishing subjects with Basal-like breast cancer from subjects with other subtypes of breast cancer is selected as the control Basal-like Subtype Score.

When the Basal-like Subtype Score for the subject is greater than or equal to a control Basal-like Subtype Score, then the subject may have TNBC Basal-like subtype. When the Basal-like Subtype Score for the subject is less than the control Basal-like Subtype Score, then the subject may not have TNBC Basal-like subtype.

In some embodiments, when a subject is determined to have TNBC Basal-like subtype, the risk of recurrence of cancer in the subject may be determined by calculating an Immune Activation Score for the subject according to the methods detailed herein.

A subject may be determined to have TNBC Basal-like subtype when the Basal-like Subtype Score for the subject is greater than or equal to a control Basal-like Subtype Score. A subject may be determined to not have TNBC Basal-like subtype when the Basal-like Subtype Score for the subject is less than the control Basal-like Subtype Score. In some embodiments when the level of expression of the genes is determined using a NanoString nCounter platform, the subject is determined to have TNBC Basal-like subtype when the Basal-like Subtype Score for the subject is greater than or equal to 350, and the subject is determined to not have TNBC Basal-like subtype when the Basal-like Subtype Score for the subject is less than 350.

a. Methods of Diagnosing a Subject with Triple-Negative Breast Cancer (TNBC) as Having TNBC Basal-Like Subtype Provided herein are methods of diagnosing a subject with triple-negative breast cancer (TNBC) as having TNBC Basal-like subtype. The method may include determining the Basal-like Subtype Score for the subject as detailed herein. The method may include determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one Basal-like gene selected from FOXC1, MKI67, CDC20, CCNE1, and ORC6; calculating a normalized expression level of each Basal-like gene by multiplying the determined level of expression of each Basal-like gene by the Normalization Factor for the subject; calculating a Basal-like Subtype Score for the subject, which is the geometric mean of the normalized expression levels of the Basal-like genes; determining that the subject has TNBC Basal-like subtype when the Basal-like Subtype Score for the subject is greater than a control Basal-like Subtype Score, and that the subject does not have TNBC Basal-like subtype when the Basal-like Subtype Score for the subject is less than the control Basal-like Subtype Score.

In some embodiments, the method further includes determining the risk of recurrence of cancer in the subject according to the methods detailed herein when the subject is determined to have TNBC Basal-like subtype.

5. TREATING CANCER IN A SUBJECT

Provided herein are methods of treating cancer in a subject. The method may include determining an Immune Activation Score for the subject that is less than a control Immune Activation Score according to the methods detailed herein, and administering chemotherapy to the subject when determined to have an increased risk of cancer recurrence. The method may include determining an Immune Activation Score for the subject that is greater than or equal to a control Immune Activation Score according to the methods detailed herein, and administering immunotherapy to the subject when determined to have a decreased risk of cancer recurrence.

In some embodiments, a biopsy of cancer cells or tumor may be taken prior to therapy. A biopsy of cancer cells or tumor may be taken prior to neoadjuvant therapy. The biopsy may be a small core tissue biopsy. The Immune Activation Score may be determined or measured from the biopsy, such as, for example, from fresh or formalin-fixed, paraffin-embedded (FFPE) procured tissues. The Immune Activation Score and methods as detailed herein may be used for biopsies taken for neoadjuvant studies and/or for retrospective analyses on samples such as FFPE tumor blocks. After a tumor is removed, a pathologic response may be assessed as a surrogate for survival information.

Chemotherapy, immunotherapy, or a combination thereof, can be delivered via a variety of routes. Typical delivery routes may include parenteral administration, e.g., intradermal, intramuscular or subcutaneous delivery. Other routes may include oral administration, intranasal, intravaginal, transdermal, intravenous, intraarterial, intratumoral, intraperitoneal, and epidermal routes. Chemotherapy, immunotherapy, or a combination thereof, may be administered to a patient in a single dose or in multiple doses. Therapies may be co-administered.

6. EXAMPLES

Example 1

Materials and Methods

NanoString Probe Design. A custom panel of probes for measuring expression of 36 genes on the NanoString nCounter platform was designed. Probe sequences were compared to RNA-seq data from TNBC tumors (Forero A, et al. *Cancer Immunol. Res.* 2016, 4, 390-399) to confirm that mRNA isoforms in TNBC would be detected by the probe sequences, and redesigned as necessary. The probe sequences were then synthesized by Integrated DNA Technologies, Inc. (Coralville, IA). The probe A oligos were HPLC purified, and the Probe B oligos were PAGE purified. The full sequence of the probes is provided in TABLE 2.

TABLE 2

MHCII Immune Activation Assay Probe Sequences.

| Gene Symbol | Transcript ID | Target SEQ ID NO. | Probe A Name | Probe A SEQ ID NO. | Probe B Name | Probe B SEQ ID NO. |
|---|---|---|---|---|---|---|
| ACTB | NM_001101.2 | 1 | NM_001101.2:1010_T001 | 2 | NM_001101.2:1010_ProbeB | 3 |
| ARHGAP9 | NM_032496.2 | 4 | NM_032496.2:2430_T002 | 5 | NM_032496.2:2430_ProbeB | 6 |
| CCNE1 | NM_001238.1 | 7 | NM_001238.1:1635_T003 | 8 | NM_001238.1:1635_ProbeB | 9 |
| CD274 | NM_014143.3 | 10 | NM_014143.3:49_T004 | 11 | NM_014143.3:49_ProbeB | 12 |
| CD3D | NM_000732.4 | 13 | NM_000732.4:110_T005 | 14 | NM_000732.4:110_ProbeB | 15 |
| CD4 | NM_000616.4 | 16 | NM_000616.4:975_T006 | 17 | NM_000616.4:975_ProbeB | 18 |
| CD69 | NM_001781.1 | 19 | NM_001781.1:460_T007 | 20 | NM_001781.1:460_ProbeB | 21 |
| CD74 | NM_001025159.1 | 22 | NM_001025159.1:964_T008 | 23 | NM_001025159.1:964_ProbeB | 24 |
| CD8A | NM_001768.5 | 25 | NM_001768.5:1320_T009 | 26 | NM_001768.5:1320_ProbeB | 27 |
| CDC20 | NM_001255.2 | 28 | NM_001255.2:430_T010 | 29 | NM_001255.2:430_ProbeB | 30 |
| CIITA | NM_000246.3 | 31 | NM_000246.3:3047_T011 | 32 | NM_000246.3:3047_ProbeB | 33 |
| CTSH | NM_004390.3 | 34 | NM_004390.3:344_T012 | 35 | NM_004390.3:344_ProbeB | 36 |
| ERBB2 | NM_001005862.1 | 37 | NM_001005862.1:1255_T013 | 38 | NM_001005862.1:255_ProbeB | 39 |
| ESR1 | NM_000125.2 | 40 | NM_000125.2:1595_T014 | 41 | NM_000125.2:1595_ProbeB | 42 |
| FOXA1 | NM_004496.2 | 43 | NM_004496.2:2465_T015 | 44 | NM_004496.2:2465_ProbeB | 45 |
| FOXC1 | NM_001453.1 | 46 | NM_001453.1:1515_T016 | 47 | NM_001453.1:1515_ProbeB | 48 |
| HLA-DMA | NM_006120.3 | 49 | NM_006120.3:380_T017 | 50 | NM_006120.3:380_ProbeB | 51 |
| HLA-DMB | NM_002118.3 | 52 | NM_002118.3:20_T018 | 53 | NM_002118.3:20_ProbeB | 54 |
| HLA-DPA1 | NM_033554.2 | 55 | NM_033554.2:857_T019 | 56 | NM_033554.2:857_ProbeB | 57 |
| HLA-DPB1 | NM_002121.4 | 58 | NM_002121.4:931_T020 | 59 | NM_002121.4:931_ProbeB | 60 |
| HLA-DQA1 | NM_002122.3 | 61 | NM_002122.3:261_T021 | 62 | NM_002122.3:261_ProbeB | 63 |
| HLA-DRB1 | NM_002124.3 | 64 | NM_002124.3:415_T022 | 65 | NM_002124.3:415_ProbeB | 66 |
| HLA-DRB5 | NM_002125.3 | 67 | NM_002125.3:31_T023 | 68 | NM_002125.3:31_ProbeB | 69 |
| IFNG | NM_000619.2 | 70 | NM_000619.2:970_T024 | 71 | NM_000619.2:970_ProbeB | 72 |
| IL7R | NM_002185.2 | 73 | NM_002185.2:1610_T025 | 74 | NM_002185.2:1610_ProbeB | 75 |
| MKI67 | NM_002417.2 | 76 | NM_002417.2:4020_T026 | 77 | NM_002417.2:4020_ProbeB | 78 |
| MRPL19 | NM_014763.3 | 79 | NM_014763.3:364_T027 | 80 | NM_014763.3:364_ProbeB | 81 |
| NCOA1 | NM_003743.4 | 82 | NM_003743.4:1225_T028 | 83 | NM_003743.4:1225_ProbeB | 84 |
| ORC6 | NM_014321.3 | 85 | NM_014321.3:382_T029 | 86 | NM_014321.3:382_ProbeB | 87 |
| PDCD1 | NM_005018.2 | 88 | NM_005018.2:310_T030 | 89 | NM_005018.2:310_ProbeB | 90 |
| PGR | NM_000926.4 | 91 | NM_000926.4:2392_T031 | 92 | NM_000926.4:2392_ProbeB | 93 |
| PSMC4 | NM_006503.2 | 94 | NM_006503.2:300_T032 | 95 | NM_006503.2:300_ProbeB | 96 |
| RPLP0 | NM_001002.3 | 97 | NM_001002.3:250_T033 | 98 | NM_001002.3:250_ProbeB | 99 |

TABLE 2-continued

MHCII Immune Activation Assay Probe Sequences.

| Gene Symbol | Transcript ID | Target SEQ ID NO. | Probe A Name | Probe A SEQ ID NO. | Probe B Name | Probe B SEQ ID NO. |
|---|---|---|---|---|---|---|
| SF3A1 | NM_001005409.1 | 100 | NM_001005409.1:25_T034 | 101 | NM_001005409.1:25_ProbeB | 102 |
| HLA-DPB2 | NR_001435.1 | 103 | NR_001435.1:599_T035 | 104 | NR_001435.1:599_ProbeB | 105 |
| HLA-DRB6 | NR_001298.1 | 106 | NR_001298.1:244_T036 | 107 | NR_001298.1:244_ProbeB | 108 |

NanoString nCounter Assay. We used NanoString nCounter Elements™ TagSets and Master Kits (NanoString Technologies, Inc., Seattle, WA) to develop the assay. Custom gene-specific oligonucleotide probes (Probe Sequence in TABLE 2) were produced by IDT (Integrated DNA Technologies, Coralville, IA). Hybridization and counting were performed according to the manufacturer's specifications. Briefly, gene-specific probes were hybridized with NanoString Elements™ TagSets and RNA at 67° C. for 24 hours. After hybridization, samples were transferred to the automated nCounter Prep Station for purification and immobilization onto the sample cartridge. After sample preparation was complete, the sample cartridge was transferred to the nCounter Digital Analyzer for imaging and analysis. All samples were analyzed using the maximum resolution setting (555 images per sample).

RNA from frozen tissues. RNA remaining from frozen tissue collected for previous studies was used (Forero A, et al. *Cancer Immunol. Res.* 2016, 4, 390-399; Varley K E, et al. *Breast Cancer Res. Treat.* 2014, 146, 287-297). The RNA-seq data from these samples are publicly available through GEO Accession GSE58135. For the comparison of frozen and FFPE sections from the same tumor, frozen breast cancer specimens were obtained from the Markey Cancer Center Biospecimen Procurement and Translational Pathology Shared Resource Facility (BPTP SRF). These tissues were collected from breast surgical specimens under IRB protocol #43618. Fresh frozen breast tissues were embedded in Tissue-Tek O.C.T. Compound (Sakura Finetek, Torrance, CA) and sectioned at -20° C. on a cryostat. An initial 4 µm tissue section was cut and stained using H&E (hematoxylin and eosin) so that tumor cellularity could be assessed by a pathologist. Only cases with ≥10% tumor cellularity were included. After assessing the H&E slide, a pathologist cut an additional 10 unstained sections at 10 µm each. Unstained sections were collected in lysis buffer and homogenized in a Bullet Blender (NextAdvance, Troy, NY); RNA was then isolated using an E.Z.N.A RNA Isolation Kit (Omega Bio-tek, Norcross, GA). After frozen sections had been taken for RNA isolation, the remnant block was taken off the cryostat, placed in a tissue cassette, and submitted for routine processing and embedding (creation of an FFPE block) in a pathology laboratory.

FFPE sample identification. This project was performed under an approved University of Utah IRB protocol (#24487). Natural language searches were used to identify surgical pathology cases with a diagnosis of invasive carcinoma of the breast. Only breast tumors from patients with primary stage I-III breast cancer were included in the study. Surgical pathology reports were reviewed by a pathologist to determine ER, PR, and HER2 status. Only TNBC cases with pre-treatment tumor material available in the archives were included. Detailed clinicopathologic, stage, and outcome data were obtained through review of the pathology report and medical record. Disease-free survival (DFS) was defined as the length of time that the patient survived after a primary diagnosis of breast cancer without any evidence of local disease recurrence or distant metastases. Events included ipsilateral breast recurrence and distant metastases.

Slide review, macrodissection, and RNA Isolation from FFPE tissue. A pathologist reviewed all cases and selected the best FFPE block from each case for analysis, taking care to avoid blocks with low tumor cellularity, or with large areas of necrosis, calcification, or fibrosis. For each block, a fresh hematoxylin and eosin (H&E) stained slide and adjacent unstained sections (10 µm) were obtained. A board-certified pathologist reviewed each H&E section and confirmed the presence of invasive breast cancer. Tumors were required to be ≥4 mm in size and to have at least 10% tumor cellularity. Using these requirements, only a single case was initially deemed inadequate due to low tumor cellularity (<10%). In this case, an alternate block was selected from the same surgical pathology specimen; the alternate block had 60% tumor cellularity and was therefore included in the study. After assessing tumor cellularity, the pathologist circled tumor on the H&E slide for macrodissection, taking care to exclude large areas of necrosis, hemorrhage, calcification, and ductal carcinoma in situ. The pathologist also measured the tumor surface area to determine the number of unstained slides required for the assay. Prior to macrodissection, unstained slides (10 µm) were de-paraffinized using Hemo-De (Scientific Safety Solvents, Keller TX), washed in 100% Ethanol, air-dried for 10 minutes, and then briefly rinsed in 3% glycerol. Tumor macrodissection was performed with a scalpel in order to isolate tumor-rich regions from unstained FFPE sections. Macrodissected tissue was subject to RNA isolation using a Roche column-based kit (HighPure FFPET RNA Isolation Kit, Roche Diagnostics, Indianapolis, IN). Briefly, macrodissected tissue from FFPE unstained slides was digested overnight in proteinase-k, RNA was bound to a silica column, treated with DNase, then eluted in 30 µL of buffer according to the manufacturer's instructions. Isolated RNA was quantified using the Qubit 3.0 and the RNA-BR (Broad-Range) assay kit (ThermoFisher Scientific, Waltham, MA). RNA quality was assessed on the 2200 TapeStation (Agilent Technologies, Santa Clara, CA) using the Agilent RNA ScreenTape Assay. RIN (RNA integrity number) values for each specimen were recorded.

Figure 6:
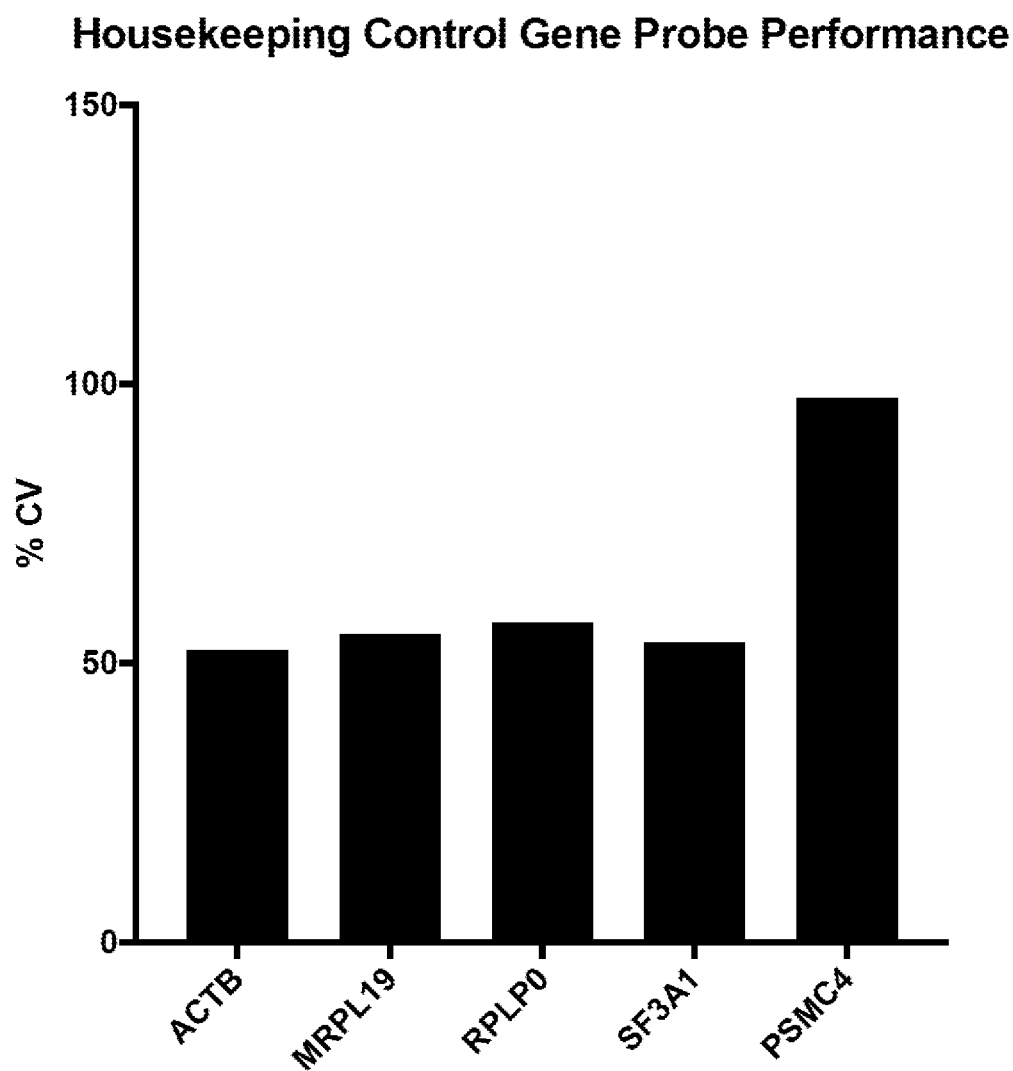
FIG. 6. The percent coefficient of variation (% CV) of the raw counts for the housekeeping controls genes is shown from a set of 33 FFPE RNA samples that had been previously subtyped using PAM50. PSMC4 had a very high % CV compared to the other housekeeping genes and was excluded from the calculation of the geometric mean of the housekeeping genes that is used as a normalization factor in this study.

Normalization of gene expression values. The gene expression count values for each sample were normalized to correct for differences in background signal intensity across runs, and to correct for differences in RNA template quality and quantity between samples. The first step of normalization was background subtraction. In each Nanostring nCounter run a "no template" control sample was analyzed. The count values for each probe in this control were subtracted from the count values for each of the patient samples in the run. This is called "Blank lane background subtraction" in the NanoString nSolver analysis software. Next, the geometric mean of the Housekeeping genes was used as a normalization factor for each sample. Notably, the probe for the Housekeeping gene PSMC4 exhibited a very high percent coefficient of variation (101%) (FIG. 6) and was excluded from the normalization factor calculation. The normalized counts for each sample were then analyzed as described below.

Statistical Analyses. Statistical analyses were performed in R version 3.5.0 and GraphPad Prism Version 7.0C. The geometric mean is often used in the literature, as well as the NanoString nSolver software, to calculate a composite score of multiple internal control housekeeping genes for normalization of gene expression assays (Vandesompele J, et al. *Genome Biol.* 2002, 3, RESEARCH0034; Bengtsson M, et al. *Genome Res.* 2005, 15, 1388-1392). In this study the geometric mean was used to calculate composite scores for Basal-like gene expression, MHCII gene expression, TIL gene expression, and Immune Activation gene expression. This ensures that each gene in the score has similar weight, regardless of their baseline expression levels and dynamic range. This was particularly important when incorporating TIL genes into the same score as the MHCII genes expressed in tumor cells, since TIL genes inherently have lower mRNA counts because they are derived from a smaller fraction of cells in the sample. Thus, higher scores represent higher expression of all of the genes in the signature, and avoids the risk that a single extremely high or low expressed gene in the signature will have uneven influence on the score.

To correct for variation in RNA sample quality and quantity, housekeeping genes were used to calculate normalized gene expression measurements for all genes measured by the assay. The procedure used included the following steps: (1) Calculate a Housekeeping Gene Score for each sample, defined as the geometric mean of gene expression measurements for one or more housekeeping genes (ACTB, MRPL19, PSMC4, RPLP0, and SF3A1); (2) Calculate the arithmetic mean of the Housekeeping Gene Scores across samples; this is the Average Housekeeping Gene Score; (3) Calculate the Normalization Factor for each sample, defined as the Average Housekeeping Gene Score divided by the Housekeeping Gene Score for each sample; and (4) Calculate normalized gene expression values for each sample by multiplying the Normalization Factor for each sample by the expression measurement for each gene in the sample.

Genes that are highly expressed in Basal-like TNBC tumors were used to assess whether a TNBC patient's tumor is the Basal-like subtype. The procedure used included the following steps: (1) Calculate a "Basal-like Subtype Score" for a TNBC tumor sample, defined as the geometric mean of one or more of the normalized Subtype Verification genes that are highly expressed in Basal-like tumors (FOXC1, MKI67, CDC20, CCNE1, and ORC6); (2) Determine if the Basal-like Subtype Score is higher than the pre-determined threshold that distinguishes Basal-like subtype tumors from other subtypes (see FIG. 1F); and (3) If the TNBC tumor is the Basal-like subtype, calculate the Immune Activation Score to assess risk of recurrence.

The Basal-like Subtype score, MHCII Score, TIL Score, and Immune Activation Score were calculated using the geometric mean of normalized counts for each gene as noted in the following formulas:

Basal-like Subtype Score=$\sqrt[5]{(FOXC1 \times MKI67 \times CDC20 \times CCNE1 \times ORC6)}$ MHCII Score=$\sqrt[10]{(CIITA \times CD74 \times HLA\text{-}DPA1 \times HLA\text{-}DPB1 \times HLA\text{-}DPB2 \times HLA\text{-}DRB1 \times HLA\text{-}DMA \times HLA\text{-}DMB \times CTSH \times NCOA1)}$ TIL Score=$\sqrt[9]{(CD3D \times CD4 \times CD8A \times CD69 \times IFNG \times IL7R \times PDCD1 \times CD274 \times ARHGAP9)}$ Immune Activation Score=$\sqrt[2]{(MHCII\ Score \times TIL\ Score)}$ Heatmaps of log normalized gene counts were created using the R package 'pheatmap' version 1.0.10. Survival analysis (Kaplan Meier plots and cox regression) was performed using the R package 'survival' version 2.42-3 and the R package 'survminer' version 0.4.2. Receiver Operator Characteristic curve analysis was performed using the R package 'pROC' version 1.12.1. The linear model of Risk of Recurrence was created using the glm package in R.

Analysis of Public Microarray Data. The Kaplan-Meier Plotter tool (http://kmplot.com) (Gyorffy B, et al. *Breast Cancer Res. Treat.* 2010, 123, 725-731) was used to perform correlative analysis of publicly available gene expression datasets for FIG. 8A and FIG. 8B and FIG. 12B. The intrinsic subtype classification provided by the Kaplan-Meier Plotter tool was used to select cases for analysis (Mihaly Z, et al. *Microarrays (Basel)* 2013, 2, 228-242). The following selections were applied to all analyses: only one JetSet best probe (Li Q, et al. *BMC Bioinformatics* 2011, 12, 474) for each gene was used in the multigene classifier that calculates the mean expression of the selected probes, relapse free survival was selected for the analysis, patients were censored at the follow-up threshold (60 months), biased arrays were excluded, and redundant samples were removed. For the Kaplan-Meier (KM) plots and survival analyses presented in FIG. 8A and FIG. 8B, only jet set best probes for MHCII signature genes were selected. The most significant cutpoint was used to split patients into two groups ("autoselect best cutoff" option). The analysis was restricted to Basal-like breast cancers in FIG. 8A, and ER+ PR+ breast cancers in FIG. 8B. For the KM plot and survival analysis presented in FIG. 12A and FIG. 12B, the jet set best probes that were available on all arrays for Basal-like tumors from patients that were systemically untreated were selected for the MHCII and TIL genes used in our Immune Activation Score calculation. Patients with Basal-like tumors that were systemically untreated were split by upper quartile.

Immunohistochemistry (IHC). IHC staining was performed on 4 µm thick sections of FFPE. The following antibodies were used: HLA-DR (Santa Cruz Biotechnology (sc-53319)) and HLA-DR/DP/DQ/DX (Santa Cruz Biotechnology (sc-53302)). FFPE sections were air-dried and then melted in a 60° C. oven for 30 minutes. Slides were loaded onto the Ventana BenchMark™ ULTRA automated staining instrument (Ventana Medical Systems, Tucson, AZ) and de-paraffinized with the EZ Prep solution. Antigen retrieval was perform using Cell Conditioning 1 (CC1, pH 8.5) for 64 minutes at 95° C. (HLA-DR and HLA-DR/DP/DQ/DX). The primary antibody (Concentration of 1:1000 for HLA-DR/DP/DQ/DX; 1:2000 for HLA-DR) was applied for 1 hour at 37° C. Signal amplification was performed with the Amplification kit (HLA-DR and HLA-DR/DP/DQ/DX). Positive signal was visualized using the UltraView DAB detection kit, which is a Universal HRP Multimer that contains a cocktail of HRP labeled antibodies (goat anti-mouse IgG, goat anti-mouse IgM, and goat anti-rabbit), utilizing DAB (3-3' diaminobenzidine) as the chromogen. Tissue sections were counterstained with hematoxylin for 8 minutes. The slides were removed from the immunostainer and placed in a dH2O/DAWN™ (Procter & Gamble, Cincinnati, OH) mixture. The sections were gently washed in a mixture of de-ionized water and DAWN™ (Procter & Gamble, Cincinnati, OH) solution to remove any coverslip oil applied by the automated instrument. The slides were gently rinsed in deionized water until all of wash mixture was removed. The slides were de-hydrated in graded ethanol, cleared in xylene and then coverslipped. For all staining runs, positive and negative controls were included and stained appropriately in all cases. Benign human tonsil was used as a positive control, while skeletal muscle was used as a negative control. In addition, positive staining in macrophages and infiltrating lymphocytes served as internal positive controls for all cases. Scoring for HLA-DR and HLA-DR/DP/DQ was performed by a board-certified pathologist who was blinded to clinical variables. Expression of HLA-DR and HLA-DRDPDQ was assessed in tumor epithelial cells using a standard semi-quantitative system: negative (0), weak (1), moderate (2), and strong (3).

Example 2

Design of the MHCII Immune Activation Assay

Figure 7:
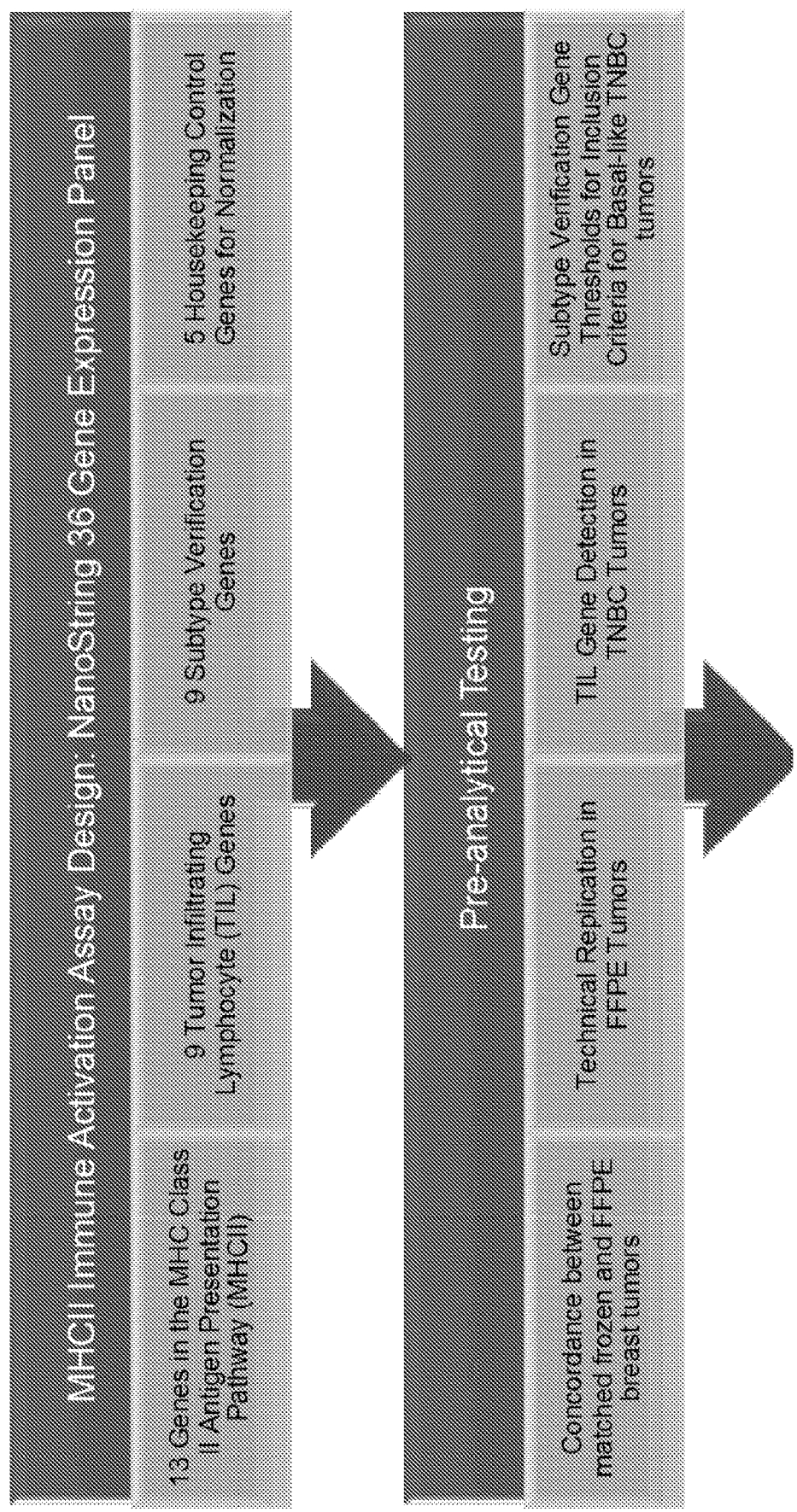
FIG. 7. Study Design and Analysis Outline.
Figure 7:
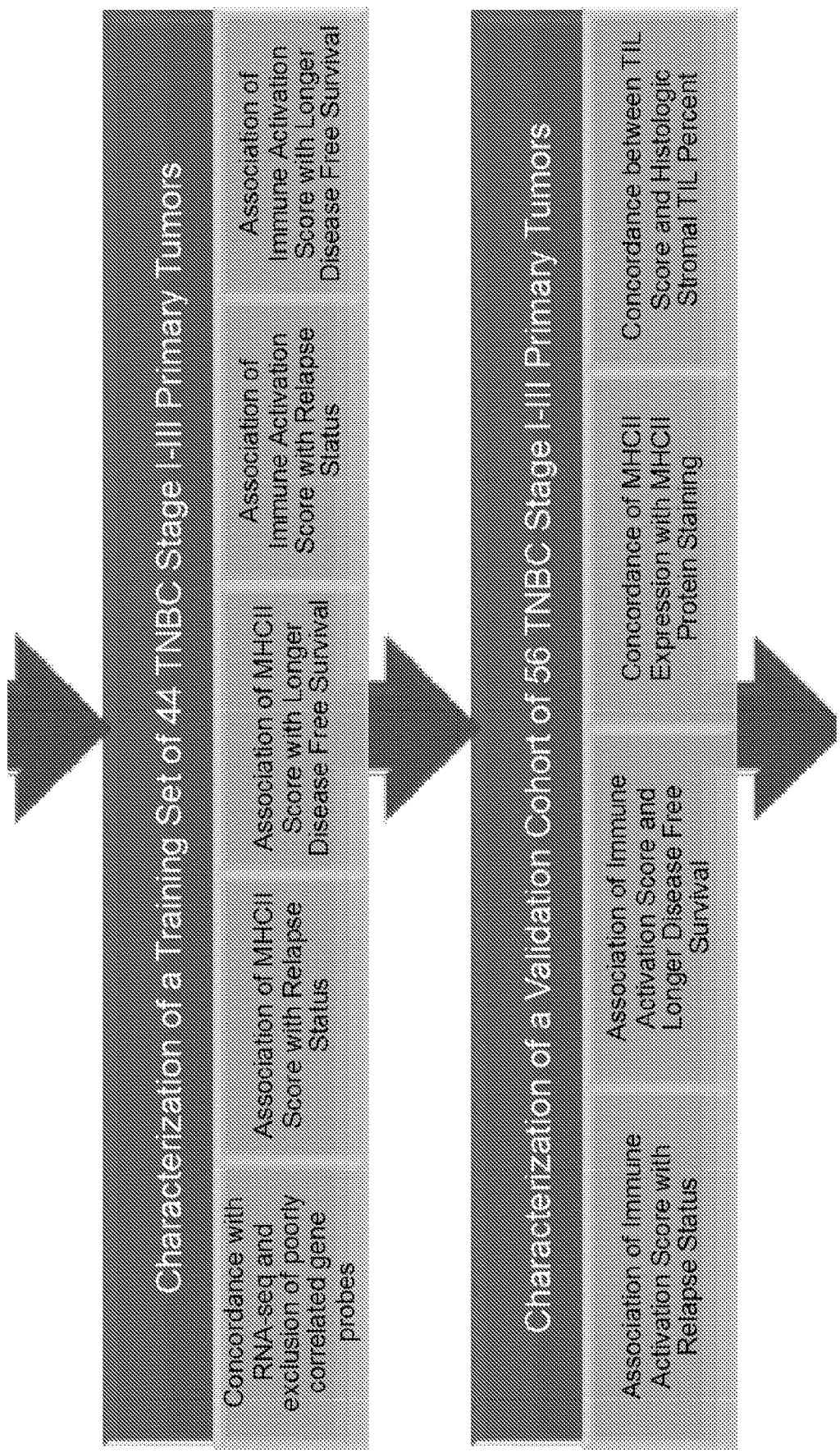
Figure 7:
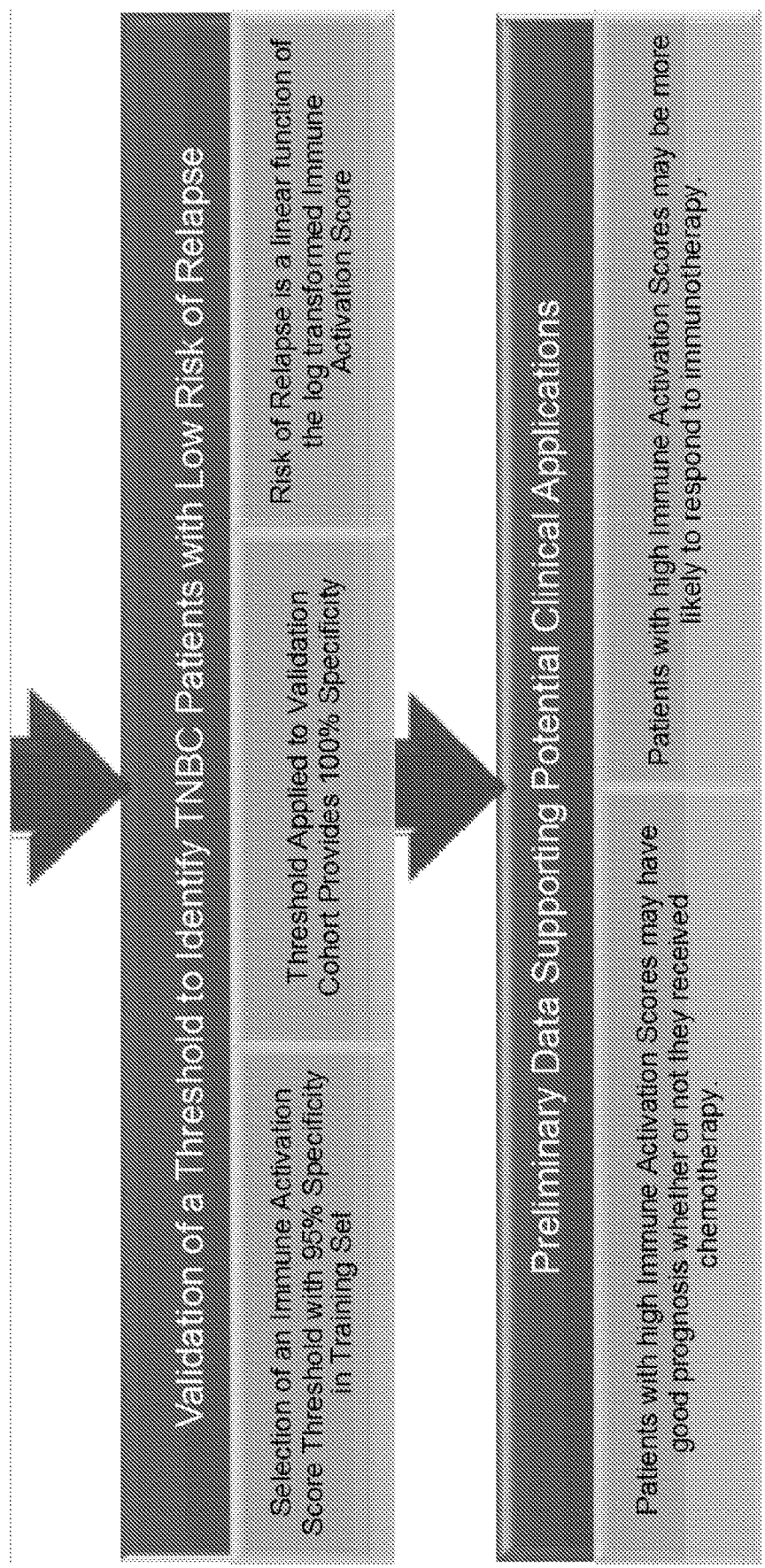

A diagrammatic outline of this study's design and analyses is provided in FIG. 7.

The major goal of this study was to develop a multiplexed gene expression assay on the NanoString nCounter platform that could accurately measure the expression of MHCII and TIL genes in FFPE TNBC tumor specimens. We have named this the "MHCII Immune Activation" assay.

The MHCII Immune Activation assay uses custom gene-specific oligo probes designed to 36 genes including MHCII Signature genes, TIL genes, Subtype Verification genes, and Housekeeping Control genes (FIG. 1A) (Probe Sequences in TABLE 2). The MHCII genes were selected based on significant association with longer DFS in the previous study (Forero A, et al. *Cancer Immunol. Res.* 2016, 4, 390-399). CIITA is the master transcriptional transactivator of the MHCII pathway and is required to induce expression of the other genes in the pathway. Candidate TIL genes were selected based on high spearman correlation (R>0.5) with CIITA expression in the TNBC tumors in the previous study (Forero A, et al. *Cancer Immunol. Res.* 2016, 4, 390-399) and membership in the Gene Otology classification "Positive regulation of T cell activation" (Mi H, et al. *Nucleic Acids Res.* 2017, 45, D183-D189; Ashburner M, et al. *Nat. Genet.* 2000, 25, 25-29; The Gene Ontology C. *Nucleic Acids Res.* 2019, 47, D330-D338). Nine candidate genes that were identified as TIL markers in recent publications were selected for the assay (Savas P, et al. *Nat. Med.* 2018, 24, 986-993; Lee H J, et al. *Breast Cancer Res. Treat.* 2015, 151, 619-627; Nirmal A J, et al. *Cancer Immunol. Res.* 2018, 6, 1388-1400). The selected TIL genes include markers of T cell types, as well as markers of T cell activation, T cell memory, and T cell interactions with tumor cells. The Subtype Verification genes were previously determined to be the best distinguishers of Basal-like TNBC from other subtypes using the PAM50 gene set (Parker J S, et al. *J. Clin. Oncol.* 2009, 27, 1160-7). During the analytical/technical development of the PAM50 signature, statistical algorithms to identify the best housekeeping control gene sets for normalization in breast cancer were developed by our group (Szabo A, et al. *Genome Biol.* 2004, 5, R59). The 5 best housekeeping control genes for normalizing classifier genes across all types of breast cancer and across different ages of FFPE procurement were selected for this assay (Szabo A, et al. *Genome Biol.* 2004, 5, R59).

Example 3

Pre-Analytical Testing of the MHCII Immune Activation Assay

Figure 1B:
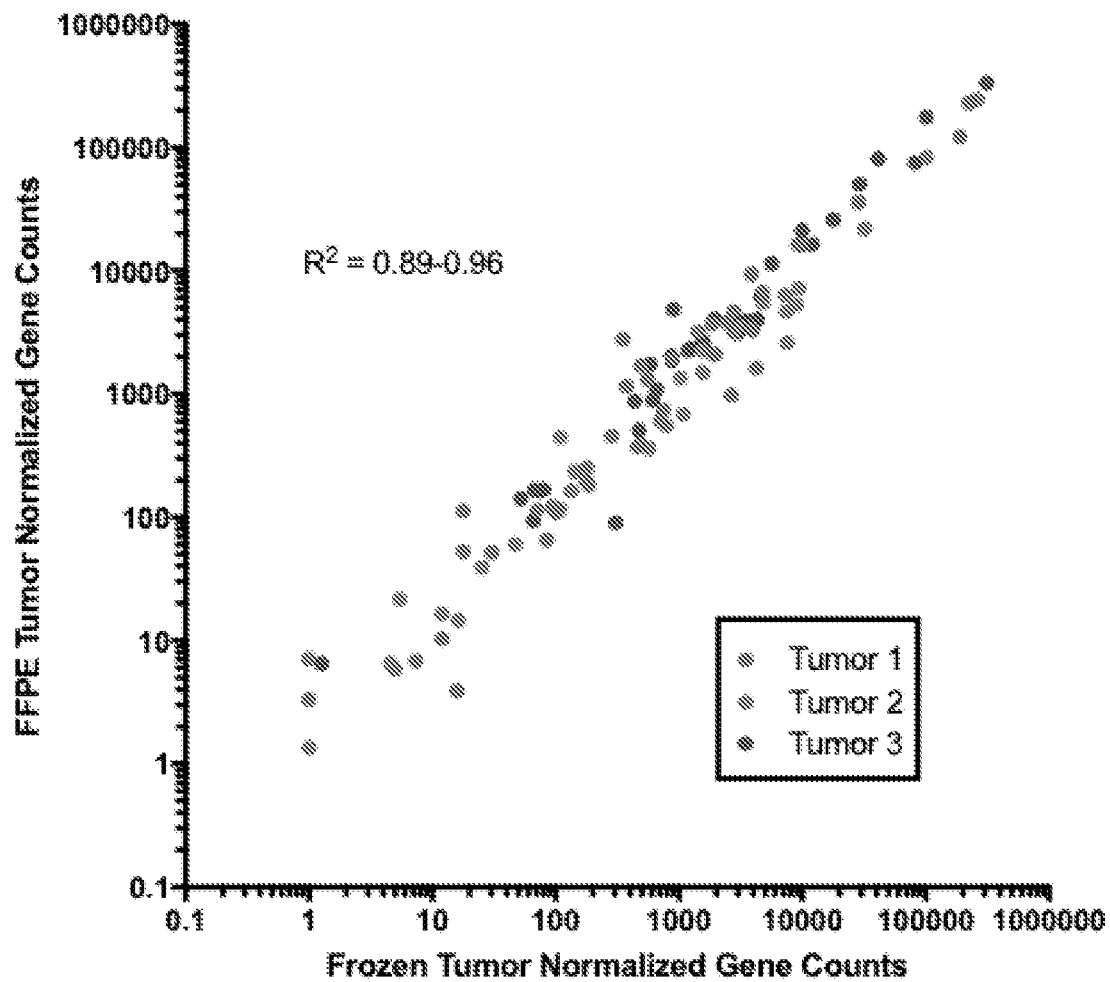

We chose to develop the assay on the NanoString nCounter platform because previous studies reported that the platform provides accurate gene expression measurements even in degraded RNA from FFPE specimens. To ensure that the MHCII Immune Activation assay accurately measures gene expression in FFPE specimens, the MHCII Immune Activation Assay was performed on three pairs of matched frozen and FFPE breast tumor specimens. Measurements were highly correlated (Spearman $R^2$=0.89-0.96; P<0.0001) between the high-quality RNA from frozen tumor sections (RNA Integrity Number (RIN)=9.0-9.7) and the degraded RNA from matched FFPE tumor sections (RIN=1.0-4.5) (FIG. 1B). Thus, the MHCII Immune Activation assay on the NanoString platform can accurately quantify gene expression in FFPE specimens.

Figure 1C:
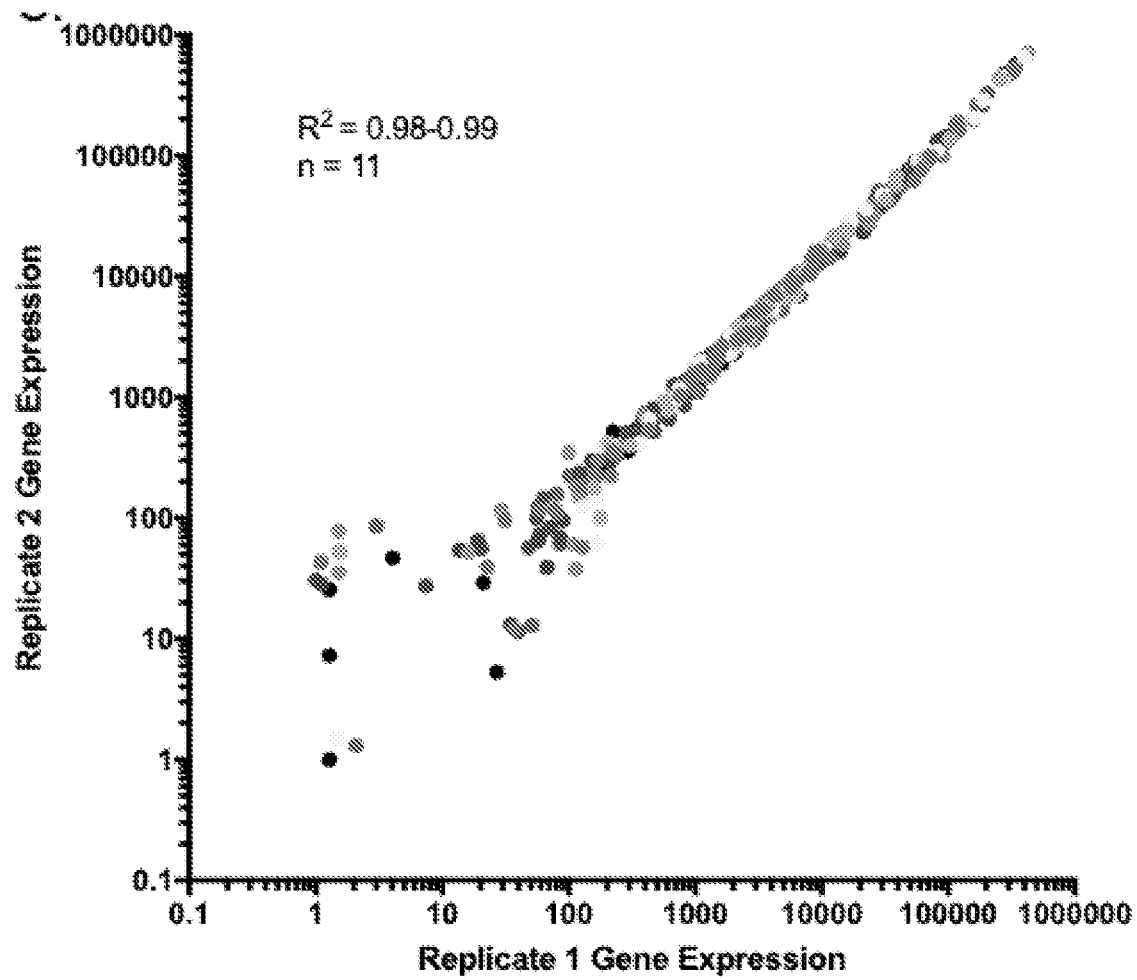

To evaluate the reproducibility of the MHCII Immune Activation assay, 11 pairs of replicate FFPE breast tumor RNA samples were analyzed on the NanoString nCounter instrument. The two sets of replicate samples were processed by two different technical teams at our institution. The normalized counts were highly correlated between the pairs of replicates for each of the 11 samples (FIG. 1C; Spearman $R^2$=0.98-0.99; P<0.0001). Genes whose normalized counts were below 10 in both replicates have higher variation between replicates, reflecting natural variation in counting rare molecules. Therefore, the MHCII Immune Activation assay provides highly reproducible results on RNA isolated from FFPE tissue.

Figure 1D:
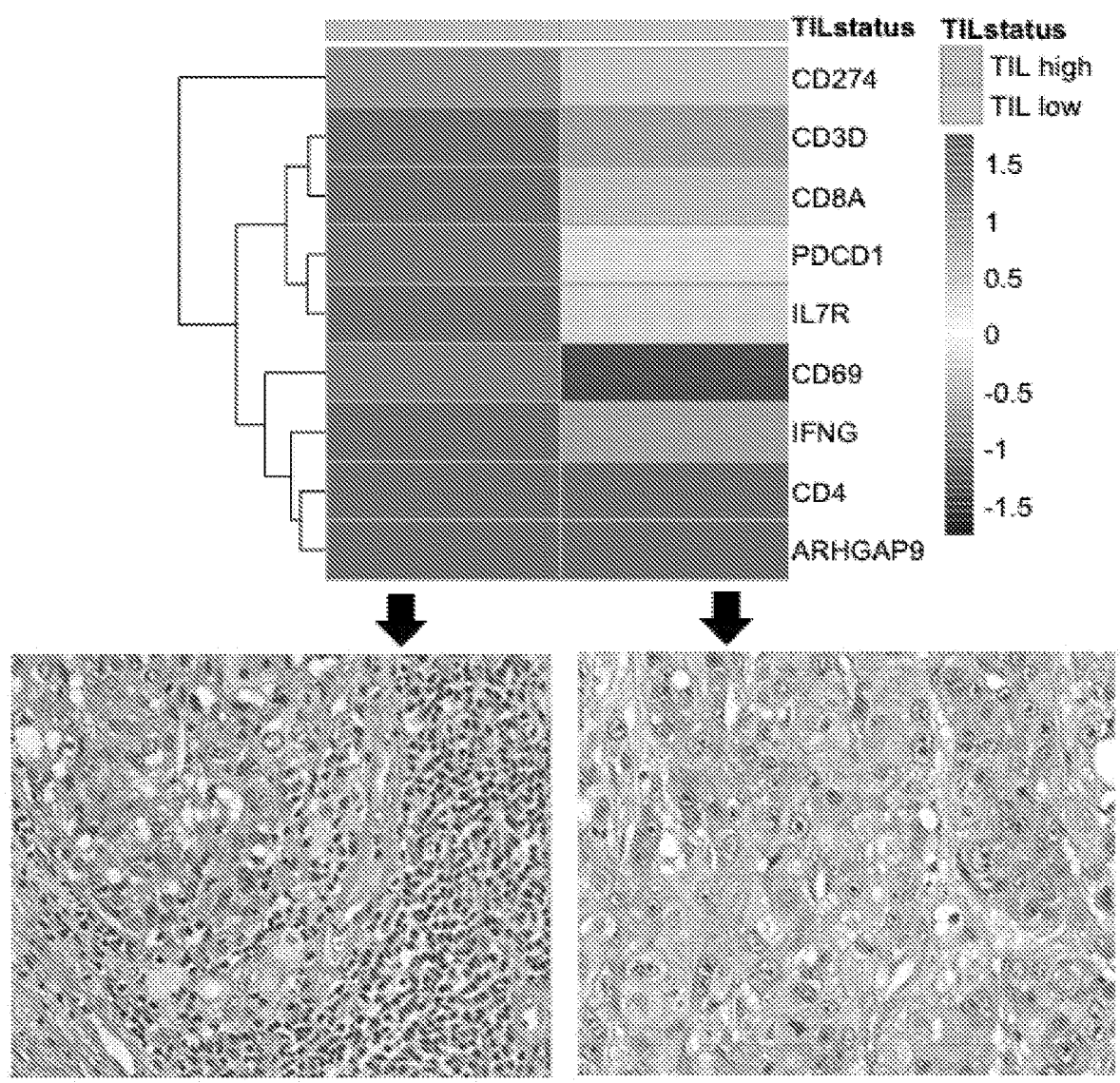

To confirm that the MHCII Immune Activation assay accurately measures TIL genes, the assay was performed on FFPE specimens from histologically confirmed TIL-high and TIL-low TNBC tumors. The TIL genes were differentially expressed between TIL high and TIL low TNBC tumors, as expected (FIG. 1D).

Figure 1E:
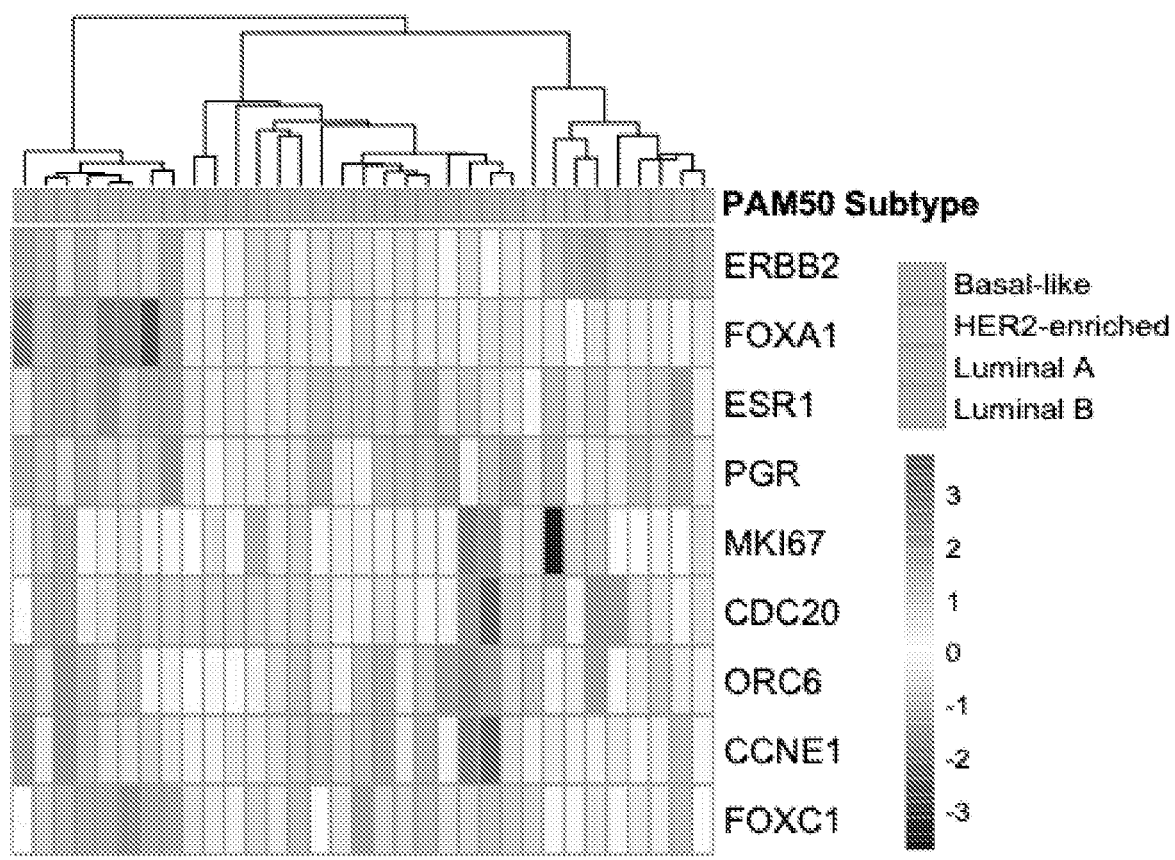
Figure 1F:
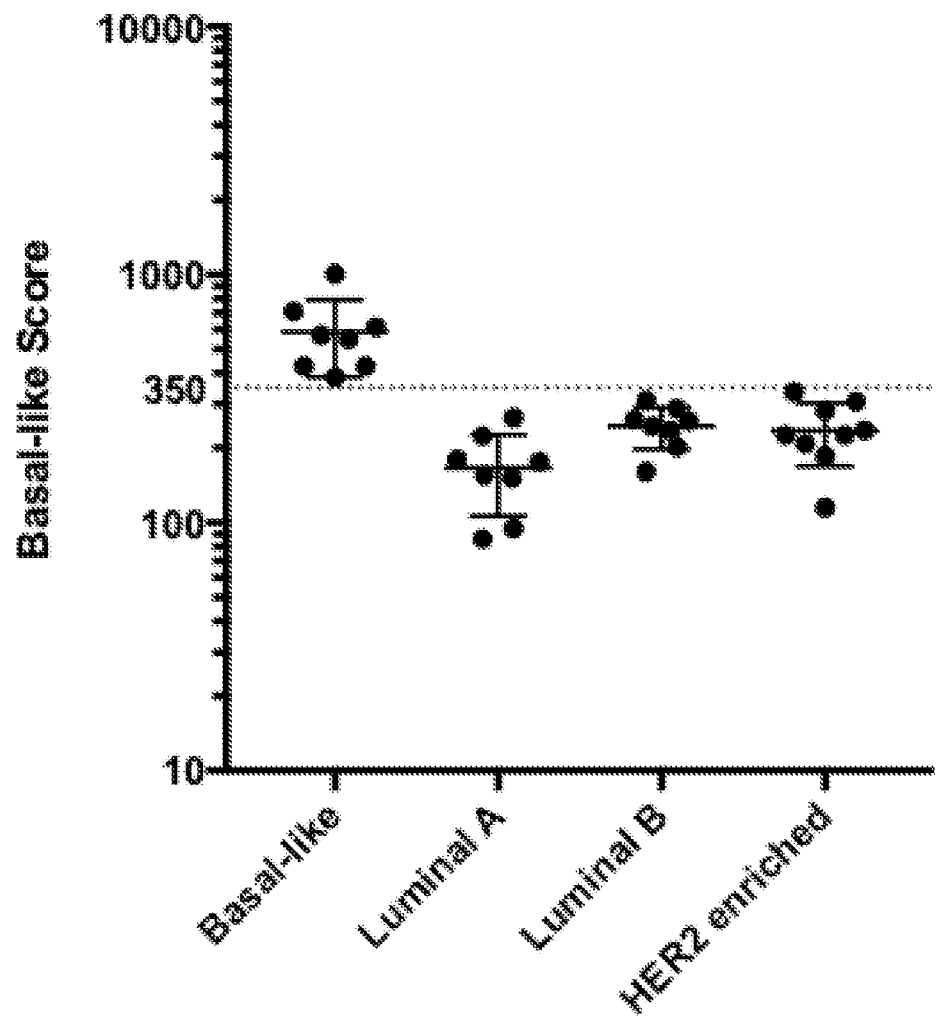
Figure 8A:
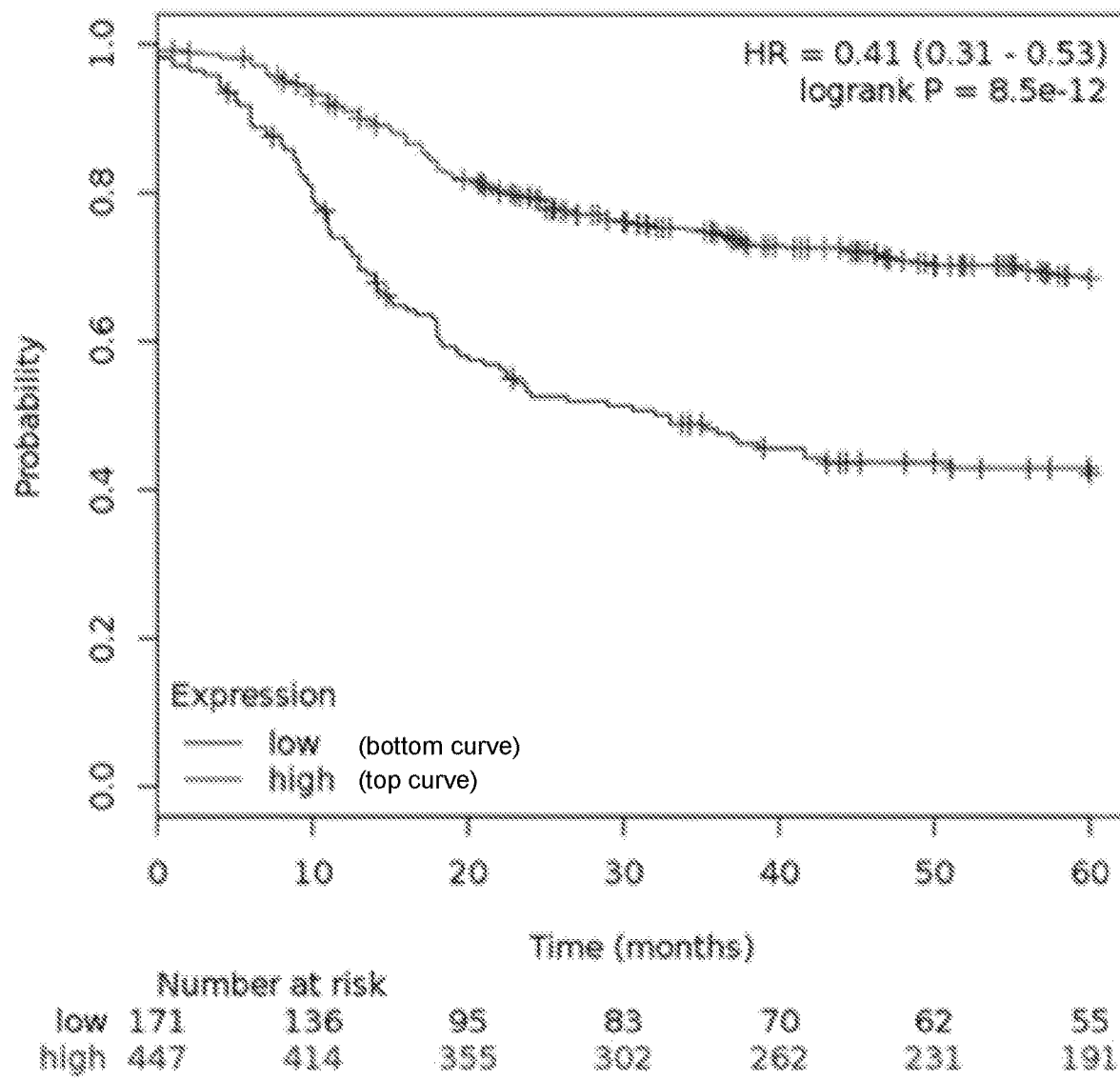
FIG. 8A, FIG. 8B. Kaplan Meier plots of public microarray data that show that expression of the MHCII gene signature is associated with significantly longer disease-free survival in basal-like tumors (FIG. 8A), but not in HR+ breast tumors (FIG. 8B).
Figure 8B:
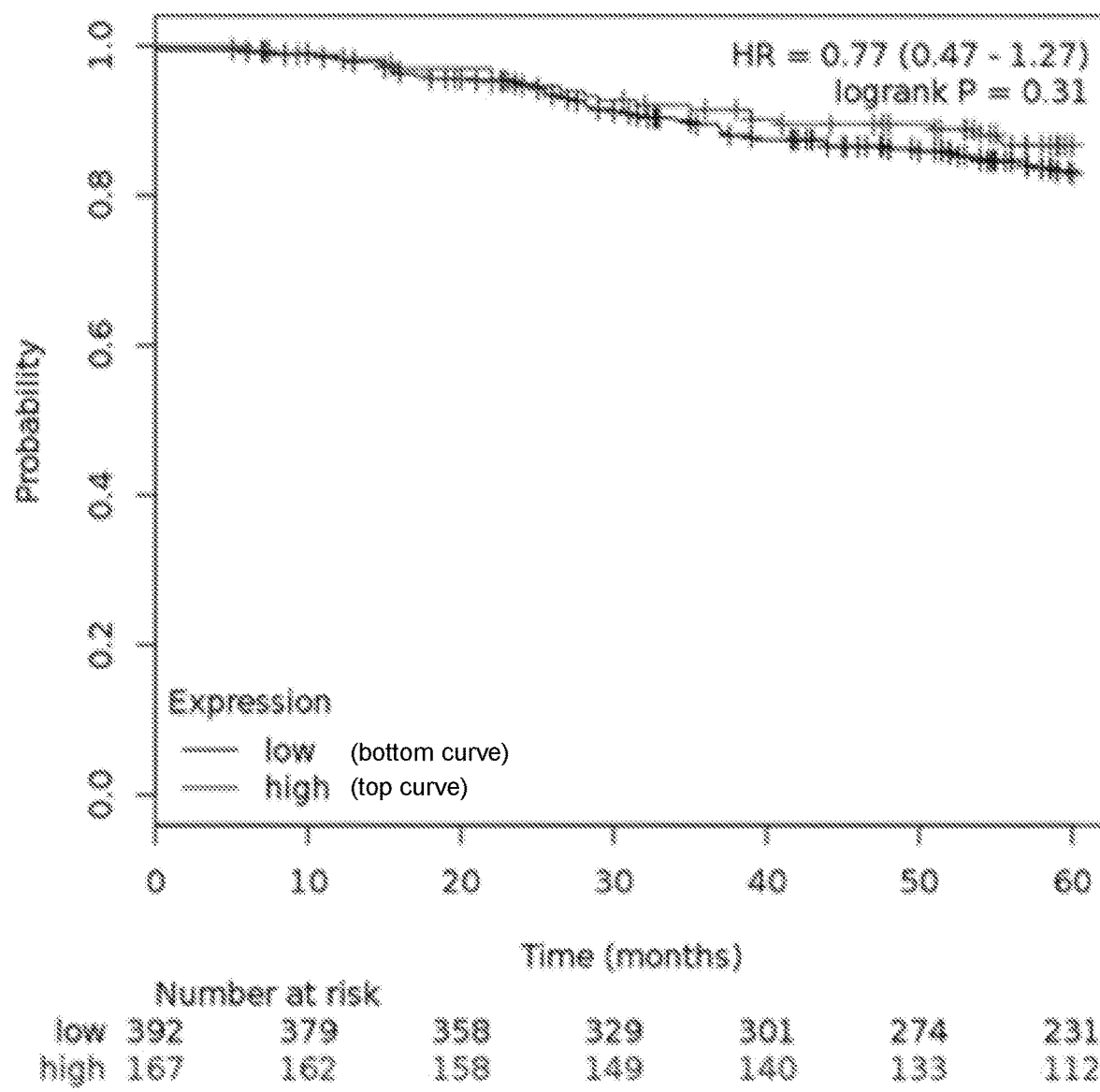

The MHCII signature was associated with improved DFS in patients with Basal-like TNBC, but not in patients with HR+ breast cancer (FIG. 8A and FIG. 8B). This observation is consistent with previous studies that have investigated immune and TIL signatures across breast cancer subtypes. In one of the largest studies, the presence of tumor infiltrating lymphocytes (TILs) was identified as an adverse prognostic factor in patients with luminal breast cancer, potentially reflecting the unique immunobiology of this HR+ subtype. Subtype Verification genes were included in the MHCII Immune Activation assay to exclude tumors that are not Basal-like TNBCs from analysis. To confirm that the Subtype Verification genes in the assay are able to discern TNBC from other subtypes of breast cancer, the MHCII Immune Activation Assay was performed on 33 FFPE breast tumor RNA samples that had been previously classified into intrinsic subtypes (Basal-like (n=8), Luminal A (n=8), Luminal B (n=8), and HER2-enriched (n=9) using the PAM50 assay (Bastien R R, et al. *BMC Med. Genomics* 2012, 5, 44). The Subtype Verification genes were differentially expressed between these subtypes of breast cancer, as expected (FIG. 1E). To develop an inclusion criterion threshold for Basal-like TNBC tumors a "Basal-like score" was calculated for each sample, defined as the geometric mean of the Subtype Verification genes that are highly expressed in Basal-like tumors (FOXC1, MKI67, CDC20, CCNE1, ORC6). A threshold for the Basal-like score that perfectly distinguished Basal-like tumors from other subtypes was selected (FIG. 1F).

Example 4

Performance of the MHCII Immune Activation Assay in a Training Set of TNBC Tumors To evaluate the accuracy of the MHCII Immune Activation assay in TNBC tumor specimens, we analyzed RNA from fresh frozen tissue samples (n=44) that had been previously analyzed using RNA-seq (Forero A, et al. *Cancer Immunol. Res.* 2016, 4, 390-399). From each sample, 50-250 ng of RNA was hybridized with the custom gene-specific probes and Elements TagSets and analyzed on the NanoString nCounter Analysis System. The gene expression counts in each sample were background subtracted and normalized to Housekeeping genes, as described in the Materials and Methods section. Five samples were excluded from analysis because they did not meet Basal-like score threshold defined in the pre-analytical testing. The remaining 39 samples were analyzed for MHCII and TIL gene expression.

Figure 2A:
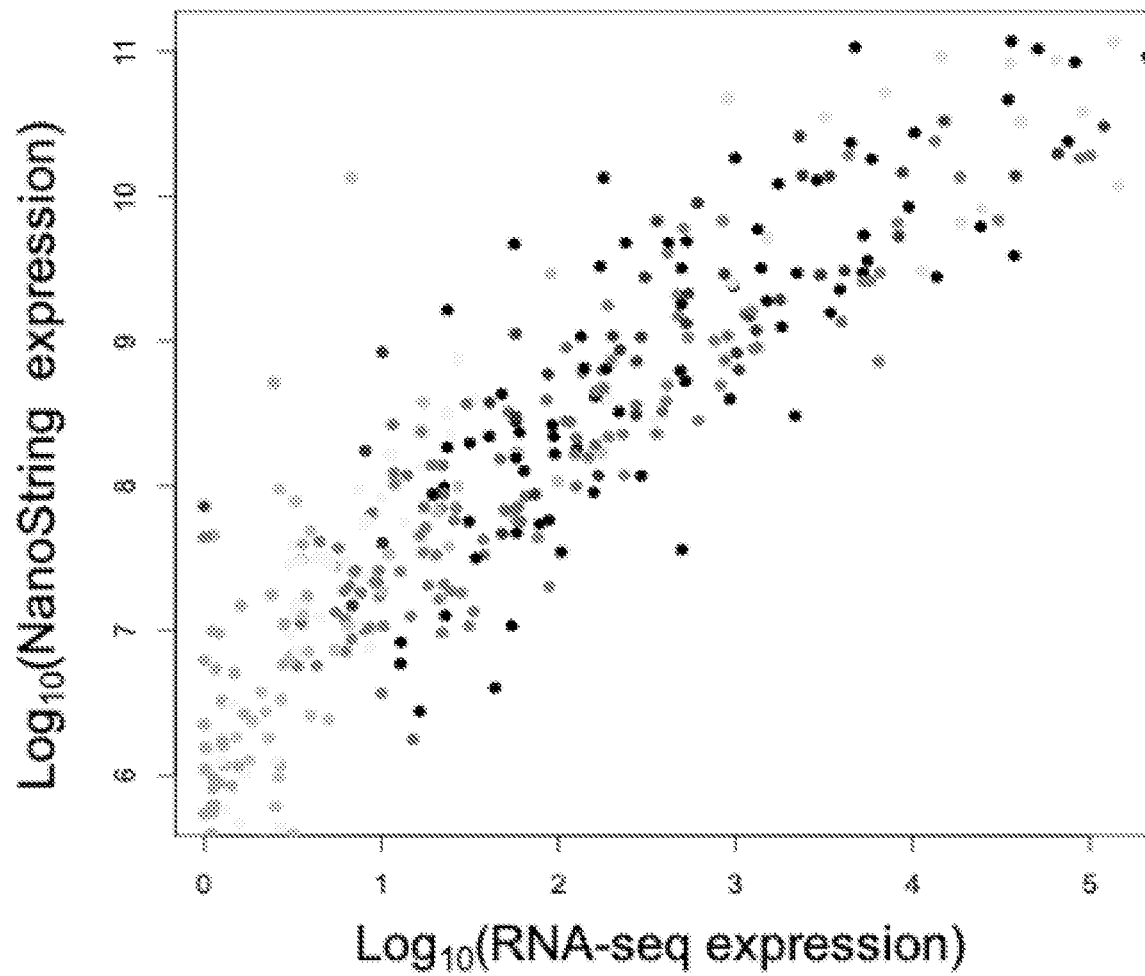
FIG. 2A, FIG. 2B, FIG. 2C, FIG. 2D, FIG. 2E, FIG. 2F. MHCII Immune Activation assay in a training set of TNBC tumors.
Figure 9B:
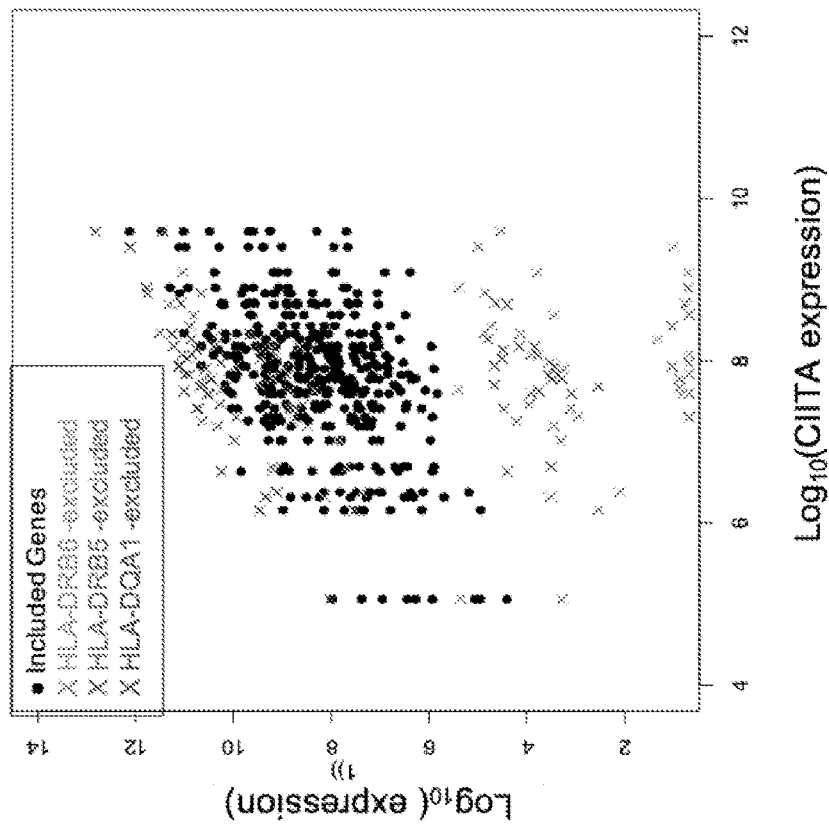
FIG. 9A, FIG. 9B.
Figure 9A:
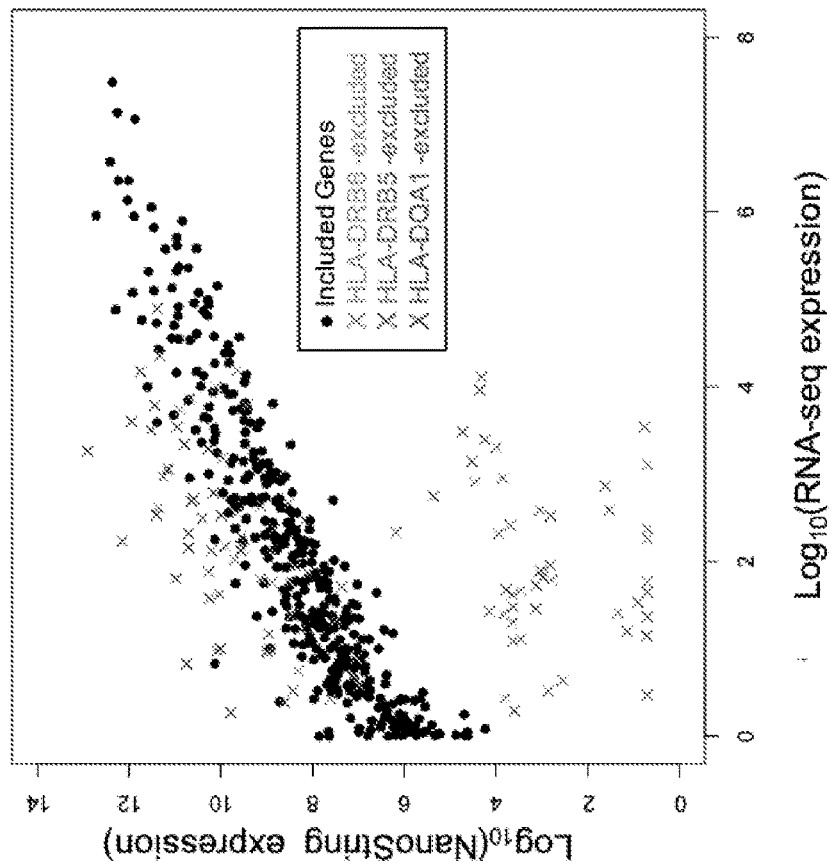

Three gene probes (HLA-DQA1, HLA-DRB5, and HLA-DRB6) were excluded from further analysis due to poor concordance between the RNA-seq and NanoString data (FIG. 9A and FIG. 9B). The remaining MHCII gene expression measurements obtained from the MHCII Immune Activation assay and from RNA-seq on the same samples were highly correlated (mean Spearman $R^2=0.88$, mean P=0.008, FIG. 2A). This result confirmed the accuracy of this new MHCII Immune Activation assay on the NanoString nCounter instrument.

Figure 2B:
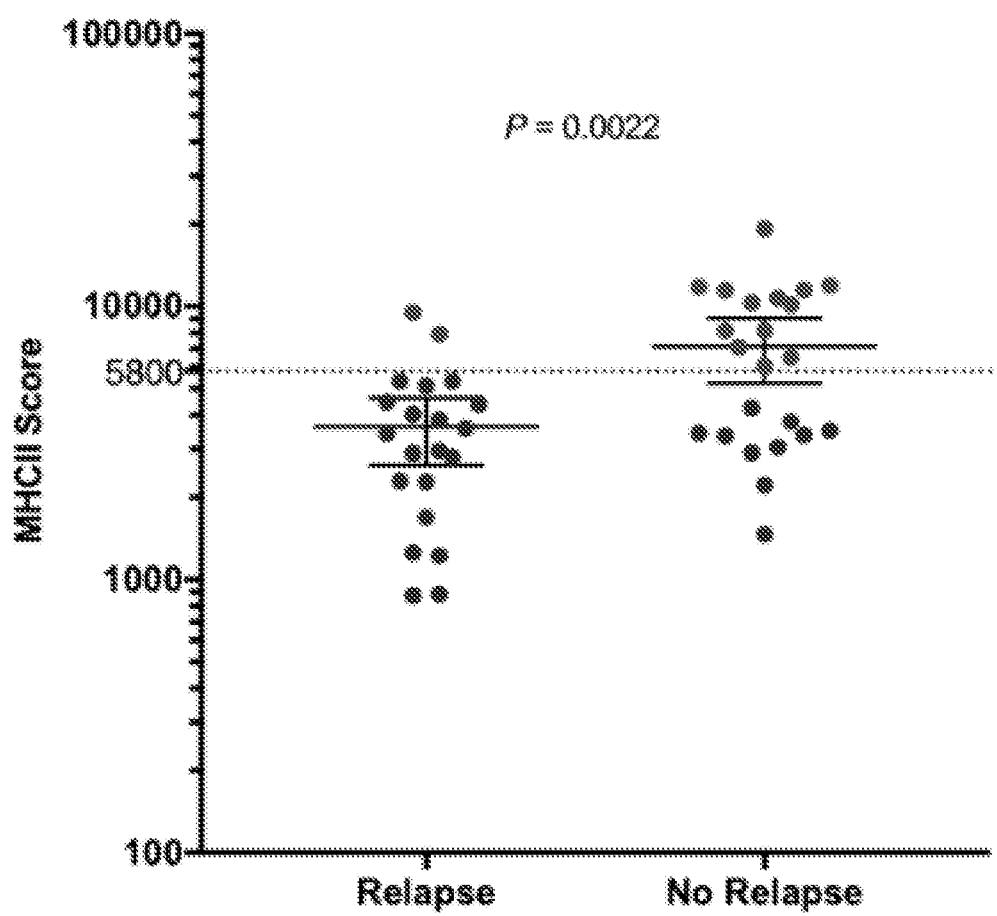
Figure 2C:
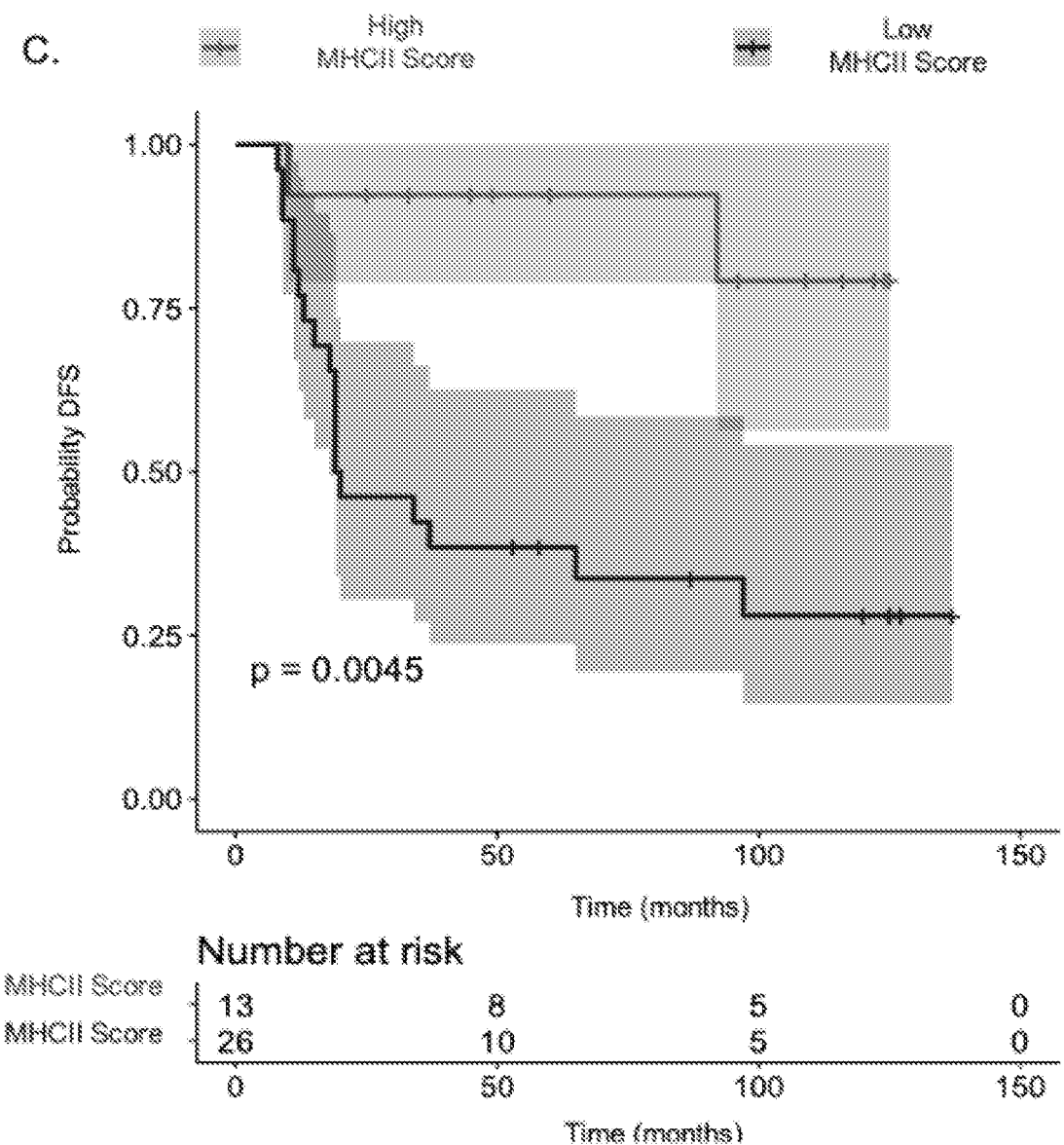

To determine if the MHCII Immune Activation assay could detect differential expression of MHCII genes between TNBC patients who relapsed and those who did not, an "MHCII Score" for each sample was calculated, defined as the geometric mean of the MHCII gene expression values. MHCII Scores were significantly higher (one-sided Mann Whitney P=0.0022) in TNBC patients who did not relapse compared to those who did relapse (FIG. 2B). A Kaplan Meier curve using a threshold for MHCII Score that provides the most significant log rank p-value demonstrated that the MHCII Immune Activation assay reproduced the significant prognostic difference between tumors with high and low MHCII expression (log rank P=0.0045, FIG. 2C, threshold depicted in FIG. 2B). This result confirmed that the MHCII gene expression signature maintains its prognostic significance on the Nanostring nCounter platform.

Figure 2D:
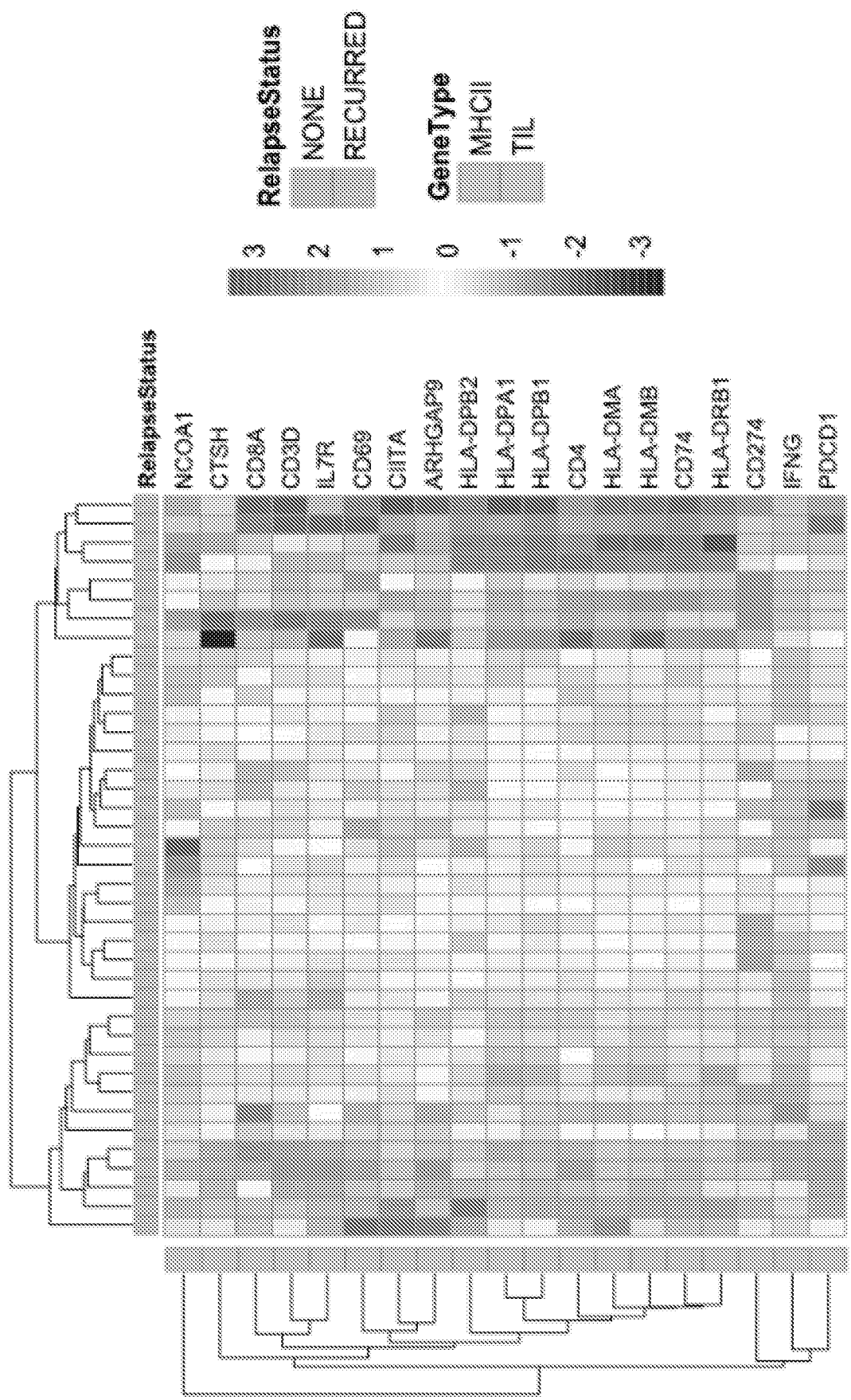
Figure 2E:
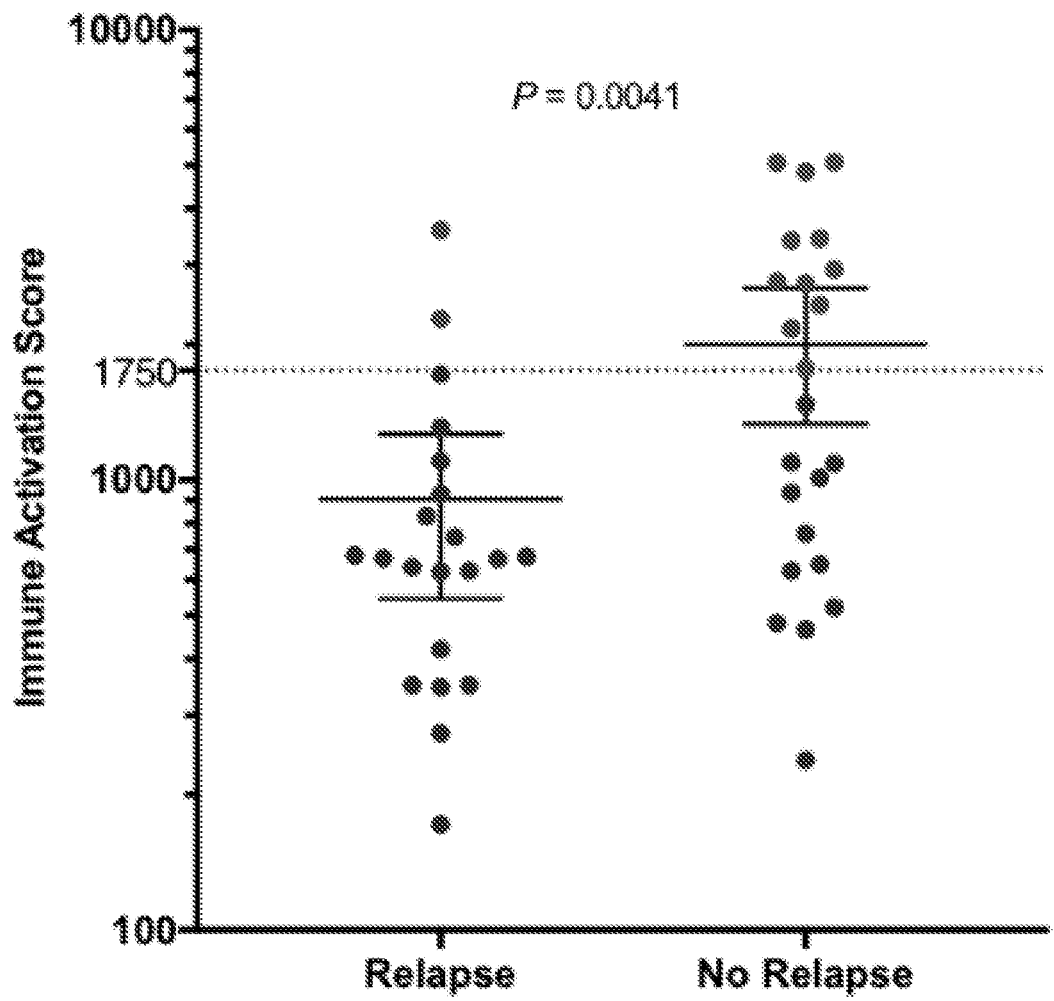
Figure 2F:
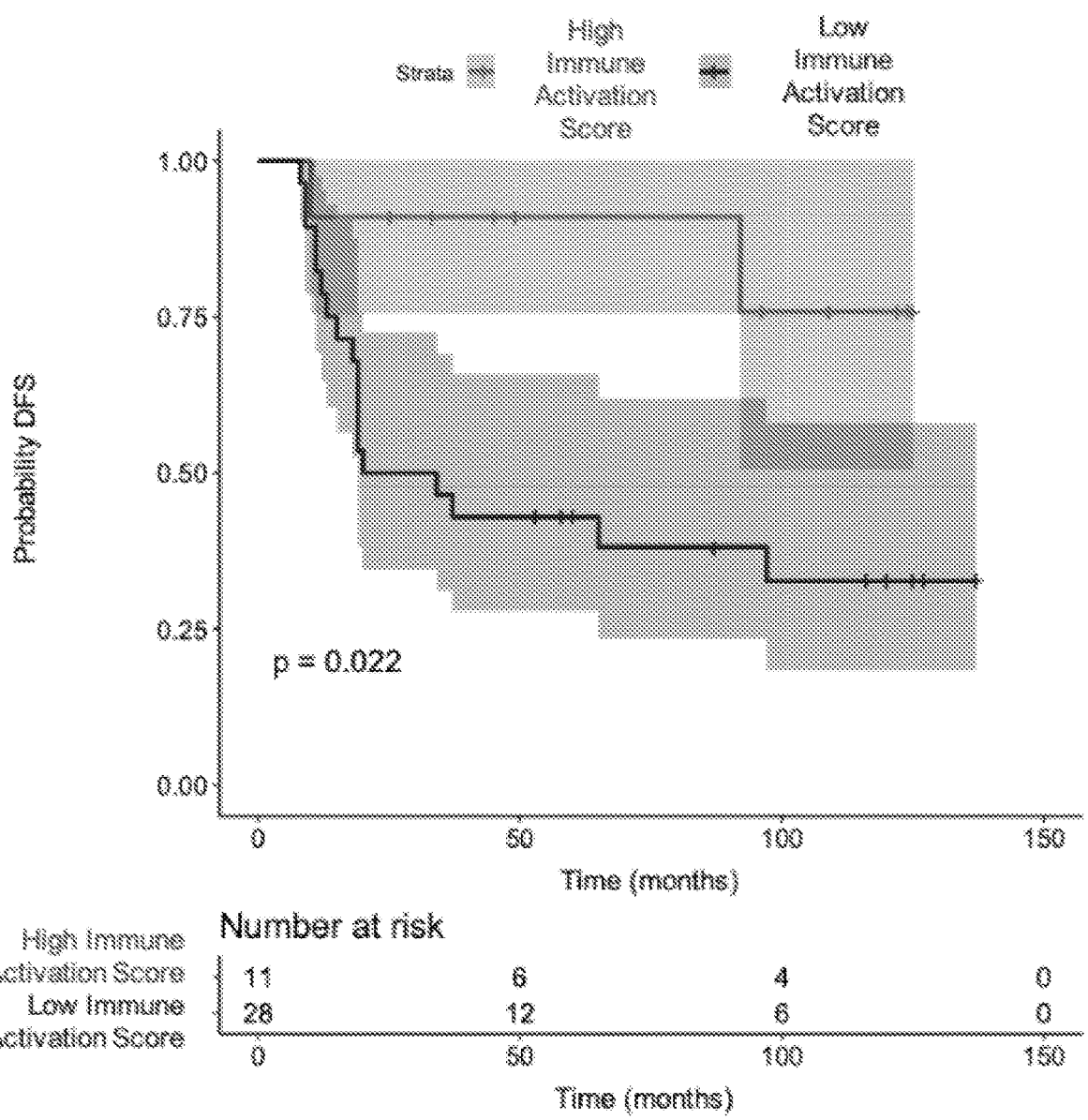
Figure 10:
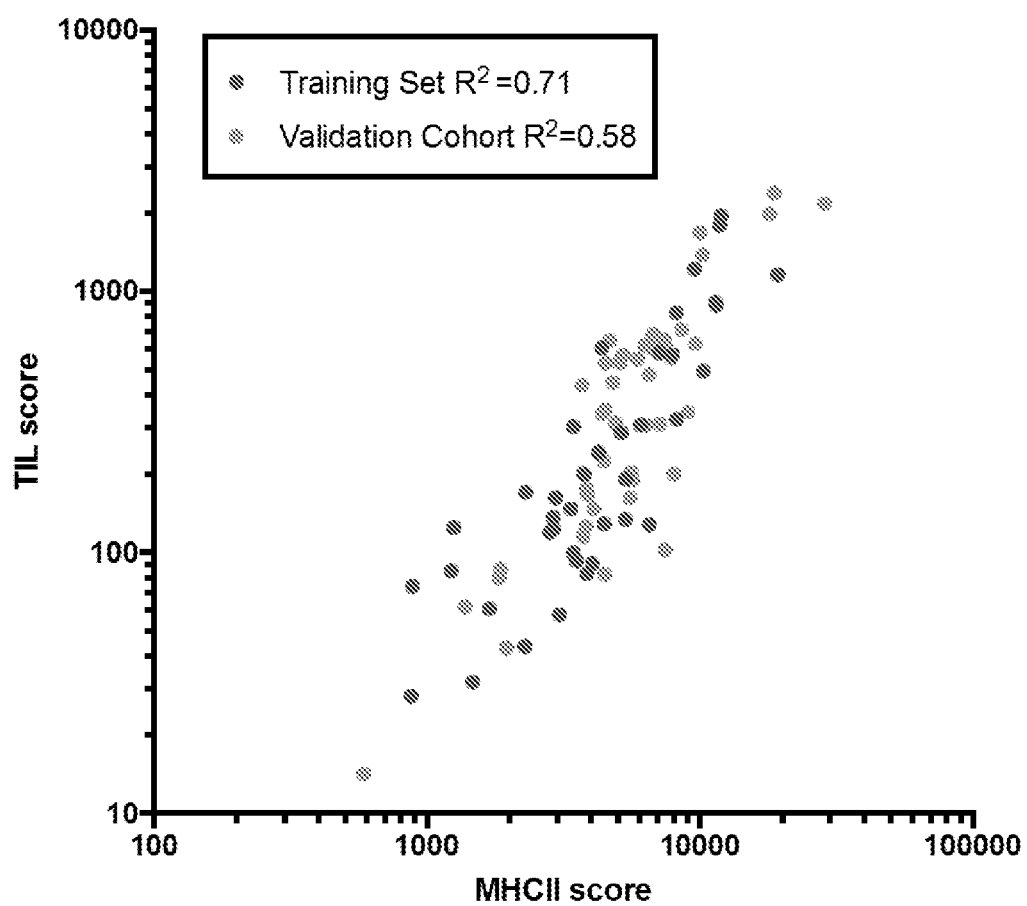
FIG. 10. The MHCII score and TIL score were correlated across the samples in the training set (green points) and validation cohort (orange points).

A heatmap of the MHCII and TIL genes in TNBC patient tumors demonstrated that expression of MHCII and TIL genes is highly correlated within a tumor (FIG. 2D). Similarly, MHCII and TIL scores were correlated across samples (Spearman $R^2=0.71$, FIG. 10). To determine whether expression of the MHCII and TIL genes could be combined into score that could be used to assess prognosis, an Immune Activation Score for each sample was calculated using the geometric mean of the MHCII and TIL gene expression values. Immune Activation Scores were significantly higher (one-sided Mann Whitney P=0.0041) in TNBC patients who did not relapse compared to those who did relapse (FIG. 2E). A Kaplan Meier curve using a threshold for the Immune Activation Score that provides the same Specificity (90%) as the MHCII score demonstrated that patients with high Immune Activation Scores have a significantly higher probability of disease-free survival than those with low Immune Activation Scores (log rank P=0.022, FIG. 2F, threshold=1750 depicted in FIG. 2E). This result confirmed the prognostic power of the Immune Activation Score generated by the MHCII Immune Activation assay.

Example 5

Validation of the MHCII Immune Activation Assay in an Independent Cohort

The second major goal of this study was to examine whether the MHCII Immune Activation assay could be used to assess prognosis in an independent institutional cohort of TNBC patients. Chart review was used to select cases that generally represent the diverse presentation and outcomes that are seen in TNBC patients in clinical practice at the University of Utah (n=56). Selected cases included age 35-70 (median 55), Stage I-III disease (majority Stage II), tumor size T1-T4 (majority T2), Histologic Grade 1-3 (majority Grade 3), and patients with positive and negative lymph nodes (TABLE 3). Overall, these demographics, and the number of cases, was similar to the cohort used in the previous study (Forero A, et al. *Cancer Immunol. Res.* 2016, 4, 390-399) and the training set, as shown in TABLE 3.

TABLE 3

Patient Demographic Data and Disease Characteristics.

| | Training Set | | | | Validation Cohort | | | |
|---|---|---|---|---|---|---|---|---|
| | Relapse | Disease-Free | Total | P-Value | Relapse | Disease-Free | Total | P-Value |
| Total Number | 21 | 23 | 44 | | 17 | 39 | 56 | |
| AJCC Stage | | | | 0.0167 | | | | 0.0039 |
| Stage I | 2 (10%) | 8 (35%) | 10 (23%) | | 2 (12%) | 17 (44%) | 19 (34%) | |
| Stage II | 12 (57%) | 14 (61%) | 25 (59%) | | 9 (53%) | 20 (51%) | 28 (50%) | |
| Stage III | 7 (33%) | 1 (4%) | 8 (18%) | | 6 (35%) | 2 (5%) | 8 (14%) | |
| Tumor Size | | | | | | | | |
| T1 | 3 (15%) | 11 (48%) | 14 (32%) | 0.0238 | 5 (29%) | 18 (46%) | 23 (41%) | 0.1019 |
| T2 | 10 (45%) | 11 (48%) | 21 (48%) | | 9 (53%) | 19 (49%) | 28 (50%) | |
| T3 | 3 (15%) | 1 (4%) | 4 (9%) | | 3 (18%) | 1 (2.5%) | 4 (7%) | |
| T4 | 4 (20%) | 0 (0%) | 4 (9%) | | 0 (0%) | 1 (2.5%) | 1 (2%) | |
| TX | 1 (5%) | 0 (0%) | 1 (2%) | | 0 (0%) | 0 (0%) | 0% | |
| Nodal Disease | | | | 0.0191 | | | | 0.0083 |
| Absent | 6 (29%) | 15 (65%) | 21 (48%) | | 5 (29%) | 27 (69%) | 32 (57%) | |
| Present | 15 (71%) | 8 (35%) | 23 (52%) | | 12 (71%) | 12 (31%) | 24 (43%) | |

TABLE 3-continued

Patient Demographic Data and Disease Characteristics.

| | Training Set | | | | Validation Cohort | | | |
|---|---|---|---|---|---|---|---|---|
| | Relapse | Disease-Free | Total | P-Value | Relapse | Disease-Free | Total | P-Value |
| Grade | | | | 0.7159 | | | | 0.3026 |
| II | 5 (24%) | 4 (17%) | 9 (20%) | | 0 (0%) | 4 (10%) | 4 (7%) | |
| III | 16 (76%) | 19 (83%) | 35 (80%) | | 17 (100%) | 35 (90%) | 52 (93%) | |
| Chemotherapy | | | | 0.3669 | | | | 0.2455 |
| Anthracycline | 13 (62%) | 18 (78%) | 31 (70%) | | 11 (65%) | 19 (49%) | 30 (53%) | |
| Other | 3 (14%) | 3 (13%) | 6 (14%) | | 2 (12%) | 13 (33%) | 15 (27%) | |
| None | 5 (24%) | 2 (9%) | 7 (16%) | | 4 (23%) | 7 (18%) | 11 (20%) | |
| Race | | | | 0.3376 | | | | 0.5713 |
| White | 15 (71%) | 13 (57%) | 28 (64%) | | 14 (82%) | 37 (95%) | 51 (91%) | |
| All Others | 5 (24%) | 9 (39%) | 14 (32%) | | 2 (12%) | 2 (5%) | 4 (7%) | |
| Unknown | 1 (5%) | 1 (4%) | 2 (4%) | | 1 (6%) | 0 (0%) | 1 (2%) | |
| Time to Relapse | | | | | | | | |
| Median (months) | 19 | | | | 12 | | | |
| Range (months) | 8-97 | | | | 4-39 | | | |
| DFS (months) | | | | | | | | |
| Average | | 96 | | | | 75 | | |
| Range | | 25-137 | | | | 28-118 | | |

A board-certified anatomic pathologist selected clinical FFPE tissue blocks in which there was adequate tumor tissue for macrodissection. All specimens were collected prior to chemotherapy. The MHCII Immune Activation assay was performed on RNA isolated from the TNBC FFPE specimens using a protocol similar to the Prosigna test, as described in detail in the Materials and Methods section.

Eleven samples were excluded from analysis because they did not meet Basal-like score threshold defined in the pre-analytical testing. The observation that not all TNBC tumors were classified into the Basal-like subtype based on gene expression is consistent with prior studies that report the presence of Luminal Androgen Receptor subtype tumors and HER2-enriched subtype tumors among TNBCs. The remaining 45 samples were analyzed for MHCII and TIL gene expression.

Figure 3A:
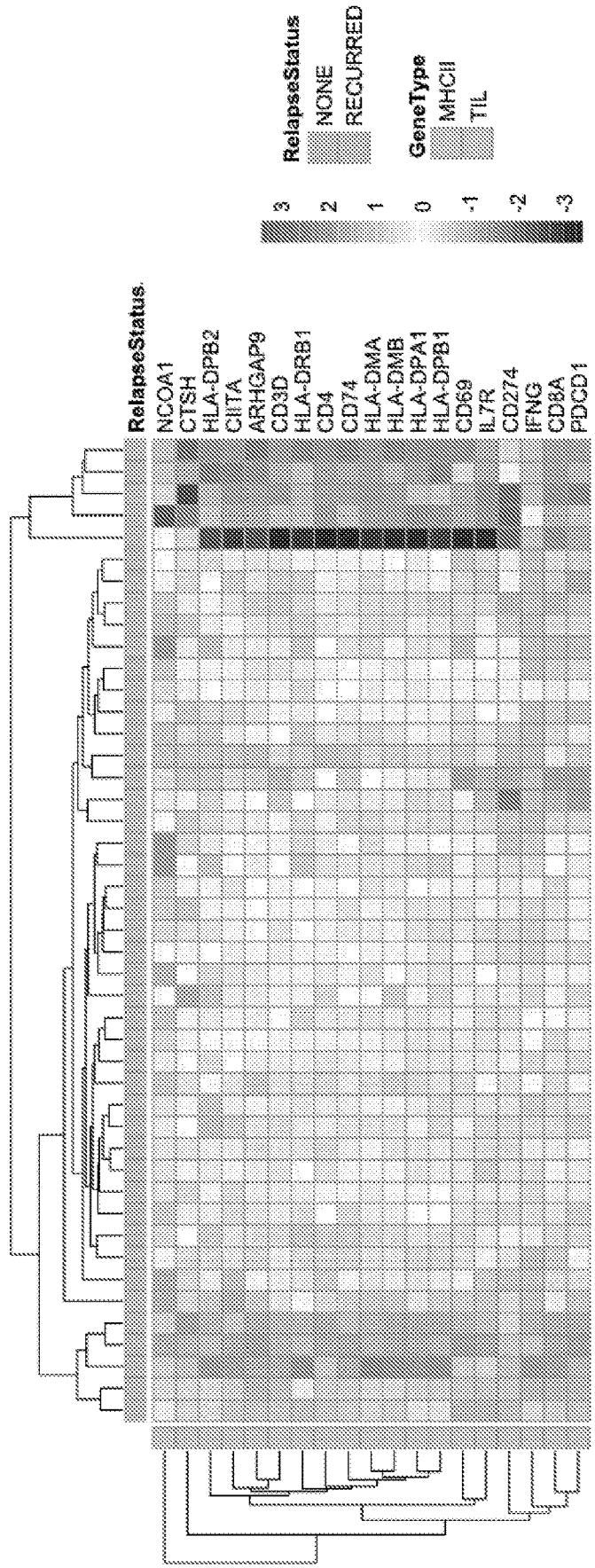
FIG. 3A, FIG. 3B, FIG. 3C. Immune Activation Scores in independent validation cohort of FFPE TNBC tumors.
Figure 3B:
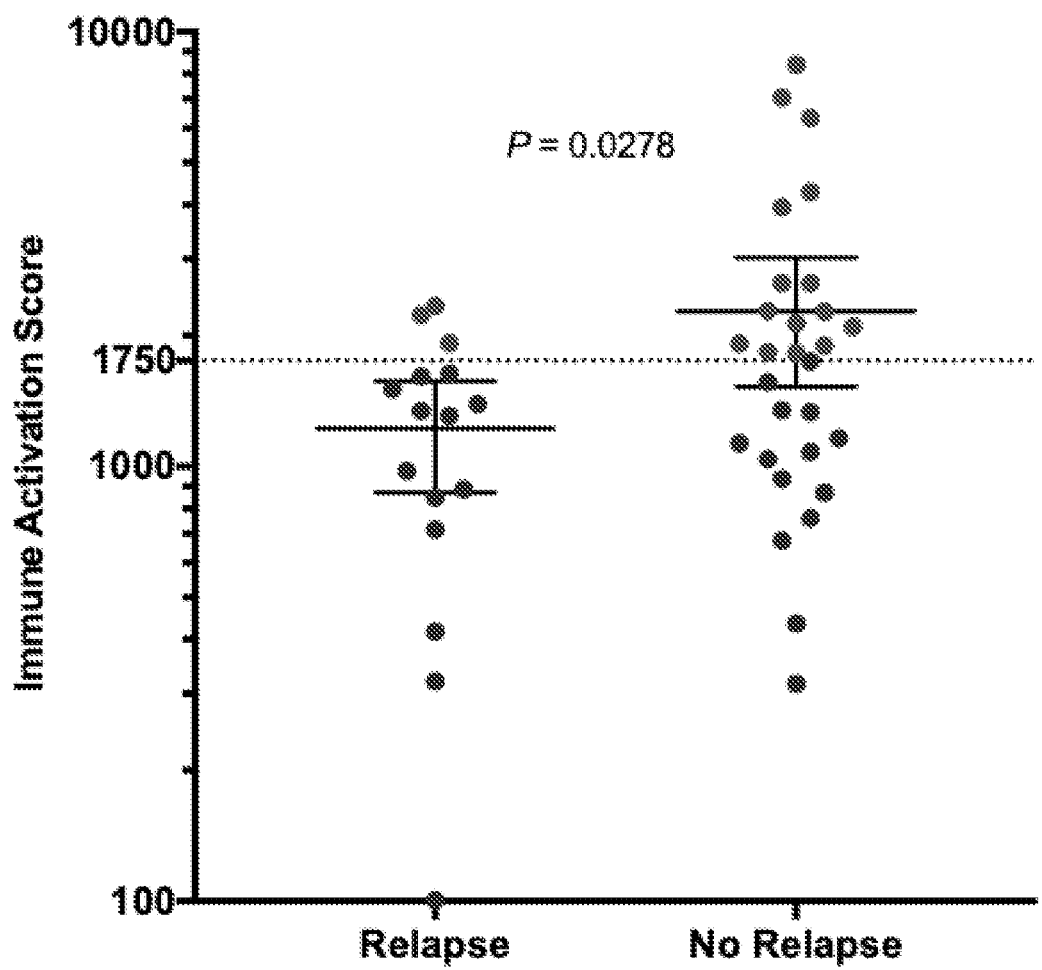
Figure 3C:
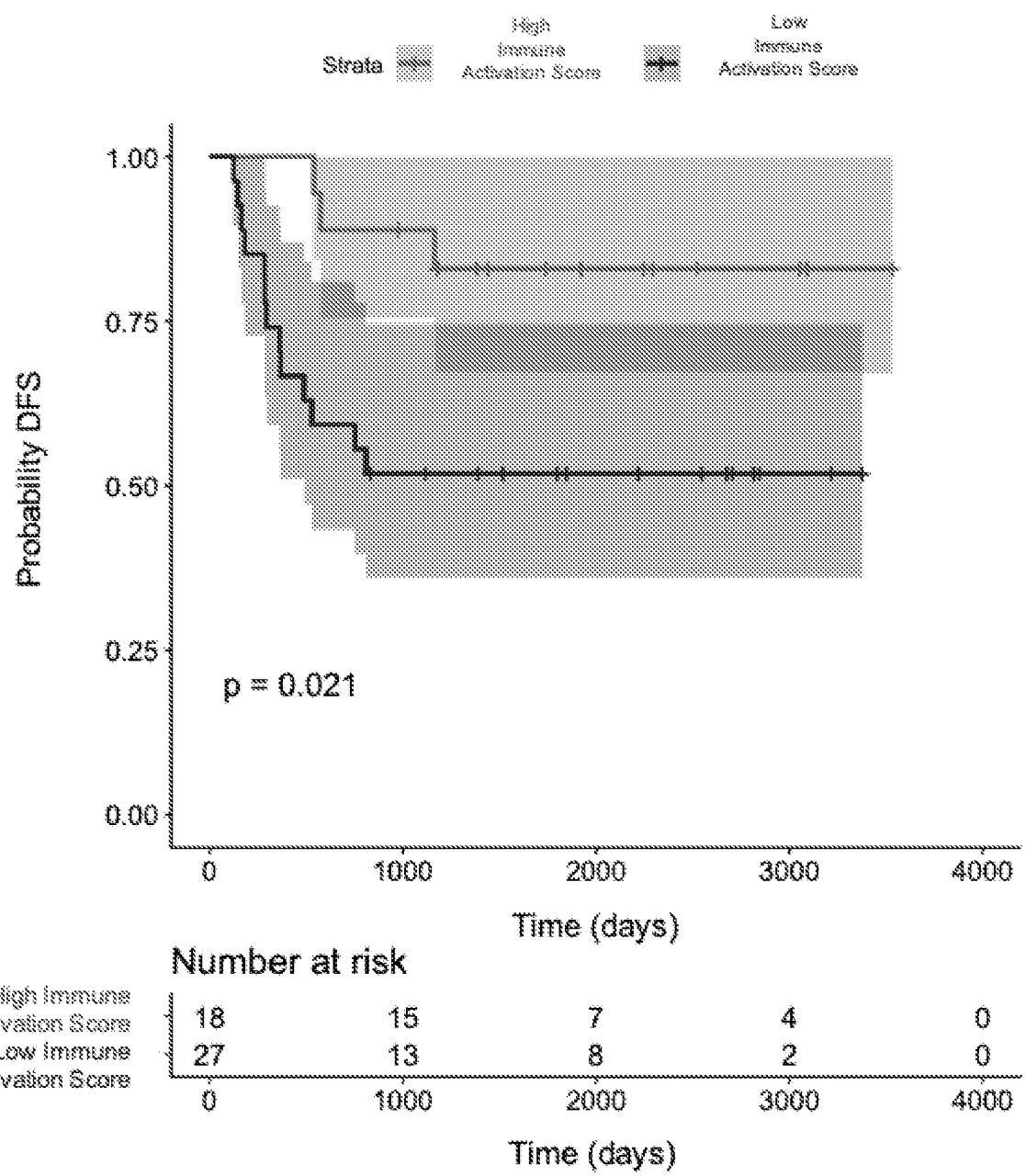

The expression of MHCII and TIL genes were correlated within each tumor, similar to the training set (FIG. 3A). MHCII and TIL scores were also correlated across samples (Spearman $R^2$=0.58, FIG. 10). The geometric mean of the MHCII and TIL gene expression values was used to calculate an Immune Activation Score for each sample. Immune Activation Scores were significantly higher (one-sided Mann Whitney P=0.0278) in TNBC patients who did not relapse compared to those who did relapse (FIG. 3B). A Kaplan Meier curve using the same Immune Activation Score threshold as the training set demonstrated a significant prognostic difference between tumors with high and low Immune Activation Scores (log rank P=0.021, FIG. 3C, threshold=1750 depicted as a dashed line in FIG. 3B). This result confirmed the prognostic significance of the MHCII Immune Activation assay in this independent cohort.

Example 6

Assessing Risk of Recurrence Using the MHCII Immune Activation Assay

Figure 4A:
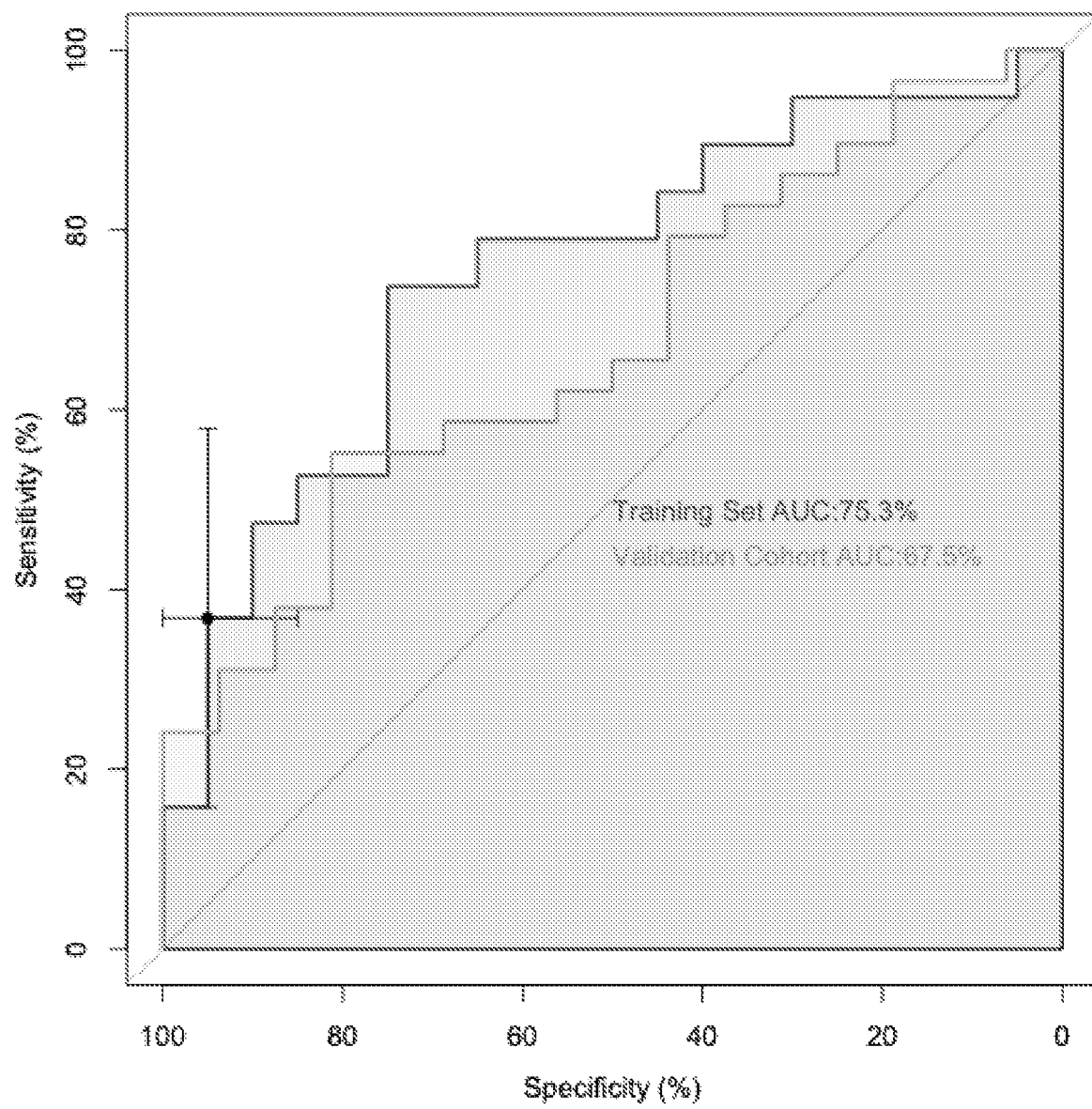
FIG. 4A, FIG. 4B, FIG. 4C, FIG. 4D, FIG. 4E. Using Immune Activation Scores to identify patients with a low risk of recurrence.
Figure 4B:
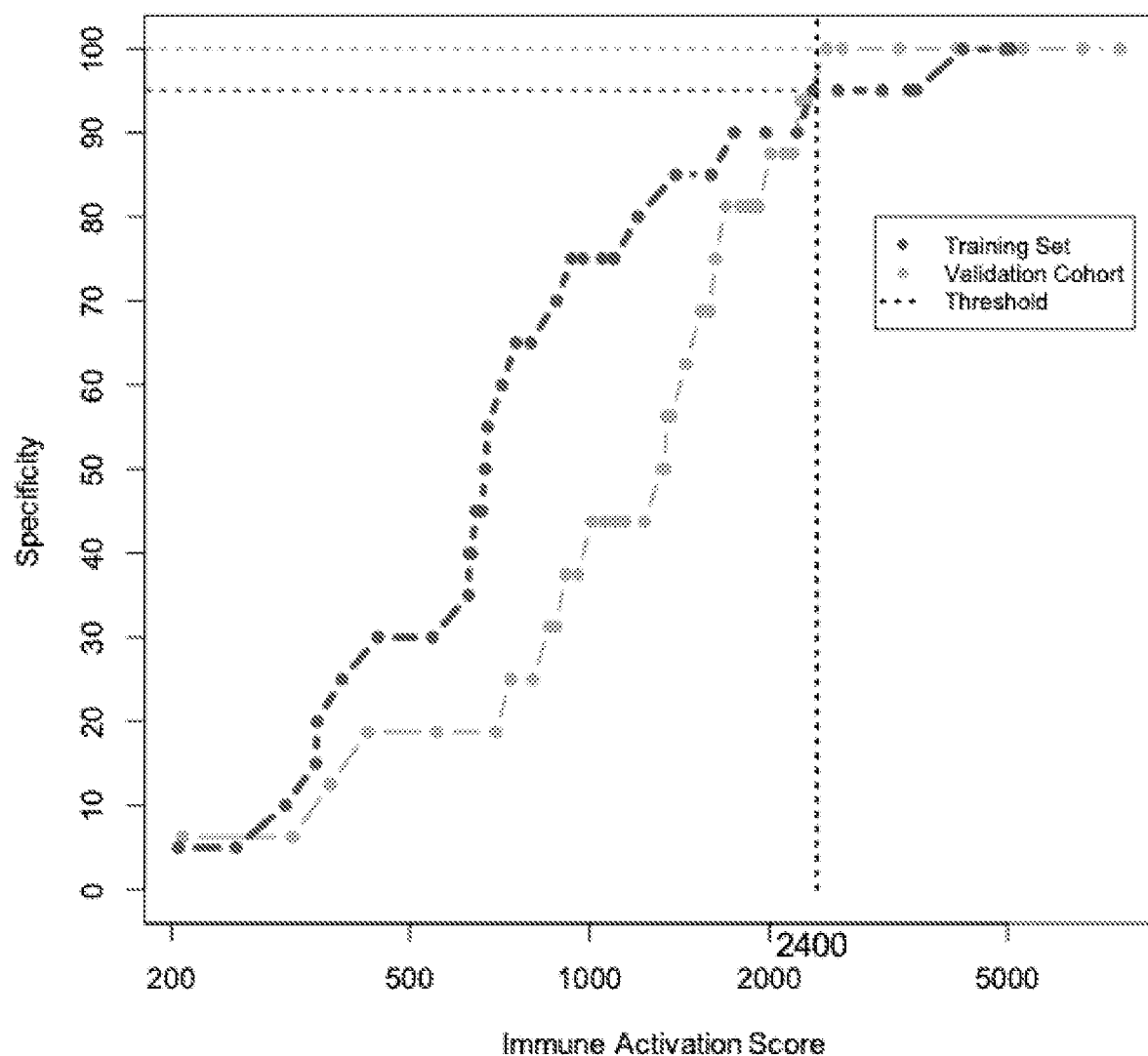
Figure 4C:
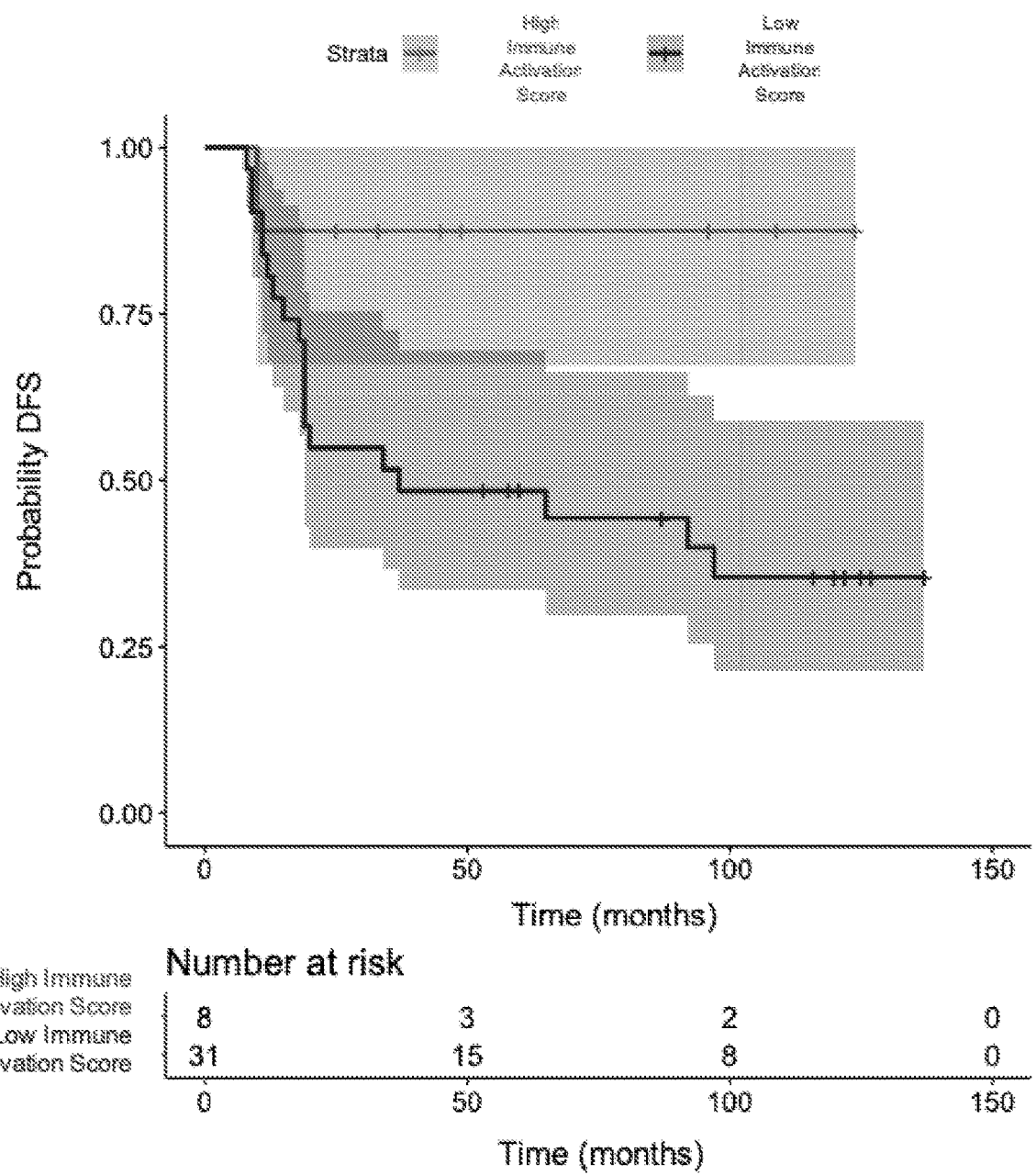
Figure 4D:
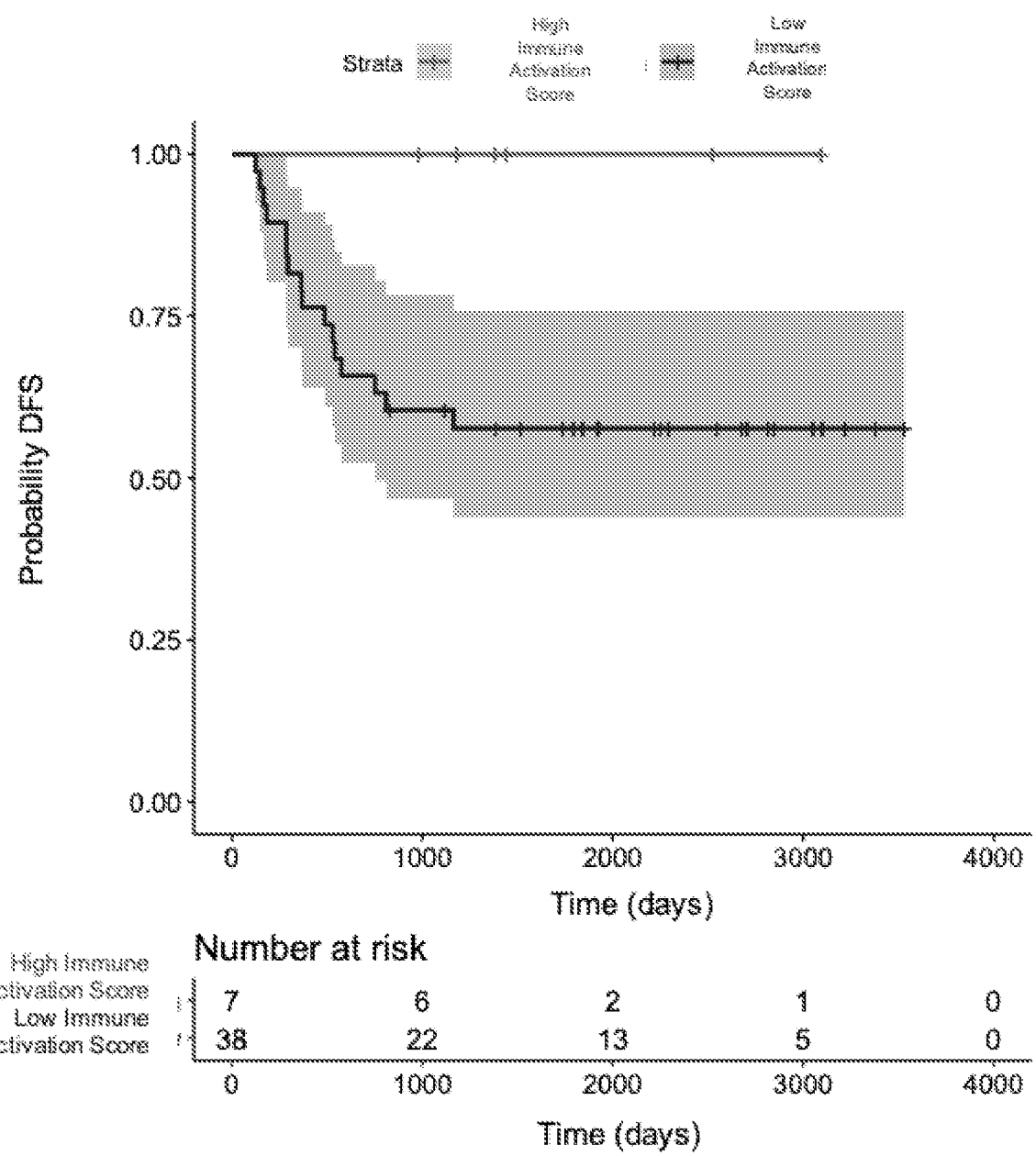

One clinical use of the MHCII Immune Activation assay would be to identify patients that have a very low risk of relapse, and distinguish them from patients who have an average risk of relapse. To determine if the MHCII Immune Activation Assay could be used to identify patients that have a very low risk of relapse, a Receiver Operator Characteristic (ROC) curve was calculated for the Immune Activation Scores in the training set and validation cohort (FIG. 4A, and ROC statistics are provided in FIG. 11A and FIG. 11B. This clinical application of the assay needs high specificity to correctly identify patients who have a low risk of recurrence, and avoid misclassifying patients that may recur. To evaluate the specificity of the assay, threshold analysis of the ROC curve was used to calculate the Immune Activation Score that results in 95% specificity for identifying patients who do not relapse in the training set (threshold=2400). The 95% confidence intervals for threshold that provides 95% specificity are depicted in the ROC curve in FIG. 4A. When this Immune Activation Score threshold was applied to the validation cohort, the specificity for identifying patients who did not relapse was 100%, i.e. zero patients with Immune Activation Scores above the threshold relapsed (FIG. 4B). Kaplan Meier curves were created using this Immune Activation Score threshold to stratify patients, which demonstrates the difference in probability of disease-free survival in both the training set (FIG. 4C) and the validation cohort (FIG. 4D).

Figure 4E:
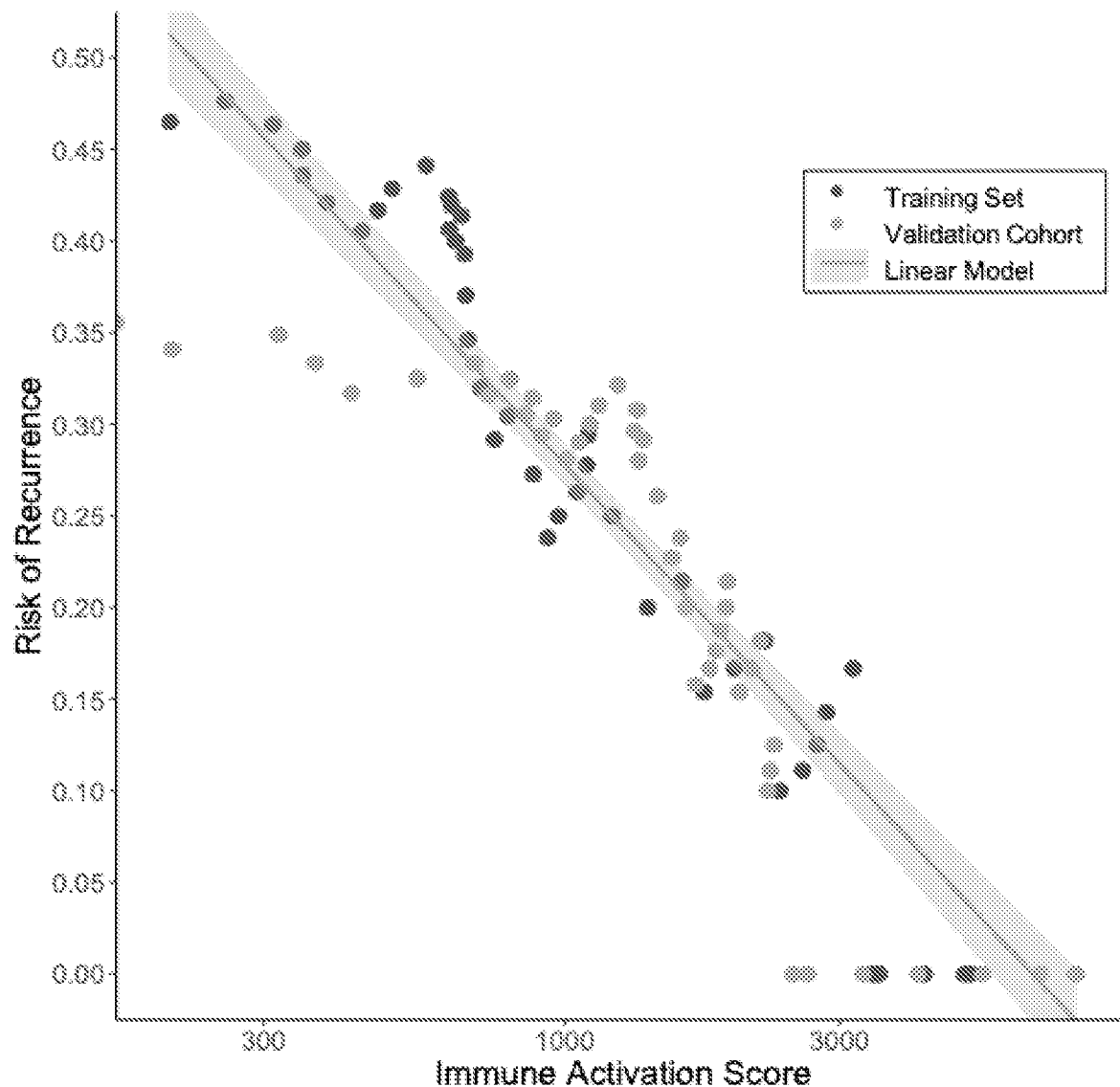

In multi-gene clinical tests used to assess prognosis in HR+ breast cancer (e.g. Prosigna and Oncotype Dx), the results are continuous variables that are linearly related to a patient's risk of recurrence. Currently, the quantitative results of these tests are used to classify patients into groups of low, intermediate, and high risk of recurrence for clinical management. The Immune Activation Score produced by this assay is also a continuous variable. To determine if the Immune Activation Score produced by this assay is linearly related to a patient's risk of recurrence, the cumulative risk of recurrence was calculated for patients across the range of Immune Activation Scores observed in the training set and validation cohort. The Risk of Recurrence in both the training set and validation cohort was a linear function of the $\log_{10}$ Immune Activation Score (FIG. 4E). This result confirmed that a patient's risk of recurrence is monotonically related to the Immune Activation Score. Thresholds may be defined to classify TNBC patients into groups with low, intermediate, or high risk of recurrence.

Cox proportional hazards regression models were generated to test the association between DFS, clinical variables, and Immune Activation Score in the training set and validation cohort. In univariate cox regression, Immune Activation Score and stage at diagnosis were significantly associated with DFS in both the training set and validation cohort (TABLE 1). The Immune Activation Score Hazard Ratio was 0.1430 (95% Confidence Interval 0.03683-0.5555) in the training set and 0.2111 (95% Confidence Interval=0.06075-0.7335) in the validation cohort, indicating a good prognostic factor. The Hazard Ratio for stage was 2.1227 (95% Confidence Interval 1.439-3.131) in the training set and 1.628 (95% Confidence Interval=1.204-2.201) in the validation cohort, indicating a poor prognostic factor. The other clinical parameters were not significantly associated with DFS, including age at diagnosis, and whether the patient received chemotherapy (TABLE 1). In the multivariable Cox proportional hazards regression model for both the training set and the validation cohort, Immune Activation Score and stage at diagnosis both remained significant, and their hazard ratios were similar to those in the univariate analysis (TABLE 1). This result indicated that the Immune Activation Score is an independent predictor of DFS, even when accounting for the differences in DFS associated with a patient's disease stage at diagnosis.

tion Score in addition to the patient's disease stage could provide improved assessment of a patient's risk of recurrence.

Example 7

Comparison of MHCII Immune Activation Assay to IHC and Histologic TIL Counting

The results from the MHCII Immune Activation assay confirmed that elevated expression of MHCII and TIL genes is associated with a significantly reduced risk of recurrence in TNBC patients. To determine if these gene expression measurements correlate with traditional histologic assessment of MHCII expression and TIL counting, IHC and H&E staining was performed on FFPE sections from the specimens analyzed in the validation cohort, which was reviewed by a board-certified anatomic pathologist who specializes in breast pathology.

Figure 5A:
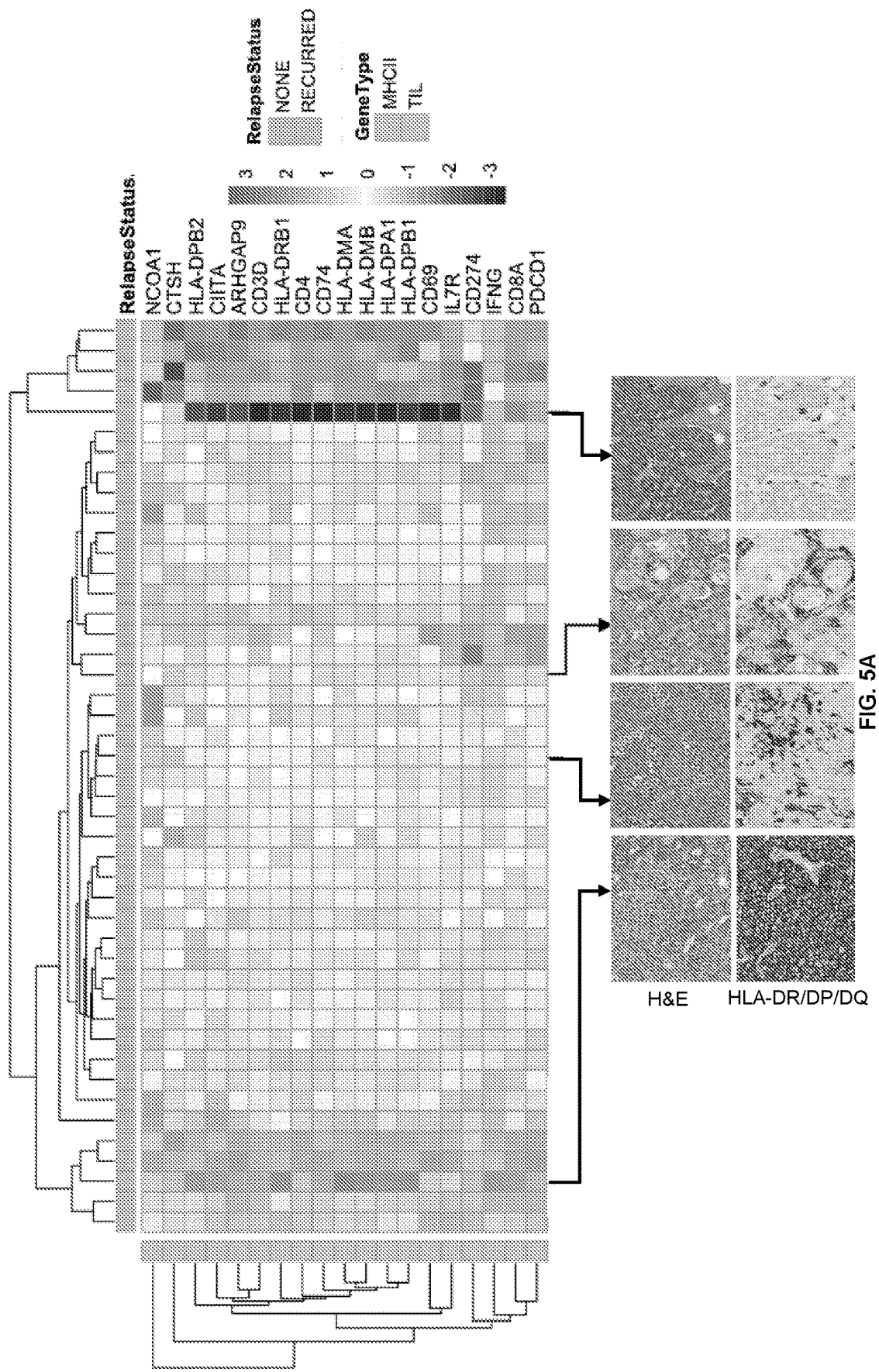
FIG. 5A, FIG. 5B. Comparison of the MHCII Immune Activation assay to IHC and histologic TIL counting.

In tumors with the highest Immune Activation Scores, MHCII protein was strongly expressed in a membranous pattern on infiltrating carcinoma cells and was associated with TILs (FIG. 5A). Tumors with an intermediate Immune Activation Score showed variable MHCII expression; in these cases, staining was often heterogeneous and of moderate intensity (FIG. 5A). In tumors with the lowest Immune Activation Scores, MHCII protein expression was absent in invasive carcinoma cells and present only in rare tumor-associated inflammatory cells (FIG. 5A).

TIL quantification was performed using a histologic "gold standard" protocol developed by a consensus committee on Tumor Infiltrating Lymphocytes (TILs) in breast cancer

TABLE 1

Cox regression models of DFS* significant P-values.

| | | Univariate | | Multivariate | |
|---|---|---|---|---|---|
| | Variable | Hazard Ratio (95% Confidence Interval) | P-value | Hazard Ratio (95% Confidence Interval) | P-value |
| Training Set | Immune Activation Score (log 10 transformed) | 0.1430 (0.03683-0.5555) | 0.00496* | 0.1688 (0.04039-0.7054) | 0.014758* |
| | Stage at Diagnosis | 2.1227 (1.439-3.131) | 0.000147* | 2.0310 (1.33617-3.0871) | 0.000911* |
| | Age at Diagnosis | 1.006 (0.9661-1.048) | 0.765 | 1.0363 (0.99081-1.0840) | 0.119459 |
| | Received Chemotherapy | 0.4879 (0.1752-1.359) | 0.17 | 0.4660 (0.14512-1.4965) | 0.199589 |
| Validation Cohort | Immune Activation Score (log 10 transformed) | 0.2111 (0.06075-0.7335) | 0.01440* | 0.1939 (0.05451-0.6896) | 0.011280* |
| | Stage at Diagnosis | 1.628 (1.204-2.201) | 0.00154* | 1.636 (1.18309-2.2632) | 0.002920* |
| | Age at Diagnosis | 1.013 (0.9812-1.045) | 0.43200 | 1.0198 (0.96152-1.0605) | 0.696870 |
| | Received Chemotherapy | 0.6166 (0.1986-1.915) | 0.40300 | 0.7696 (0.14986-3.9519) | 0.753700 |

Figure 5B:
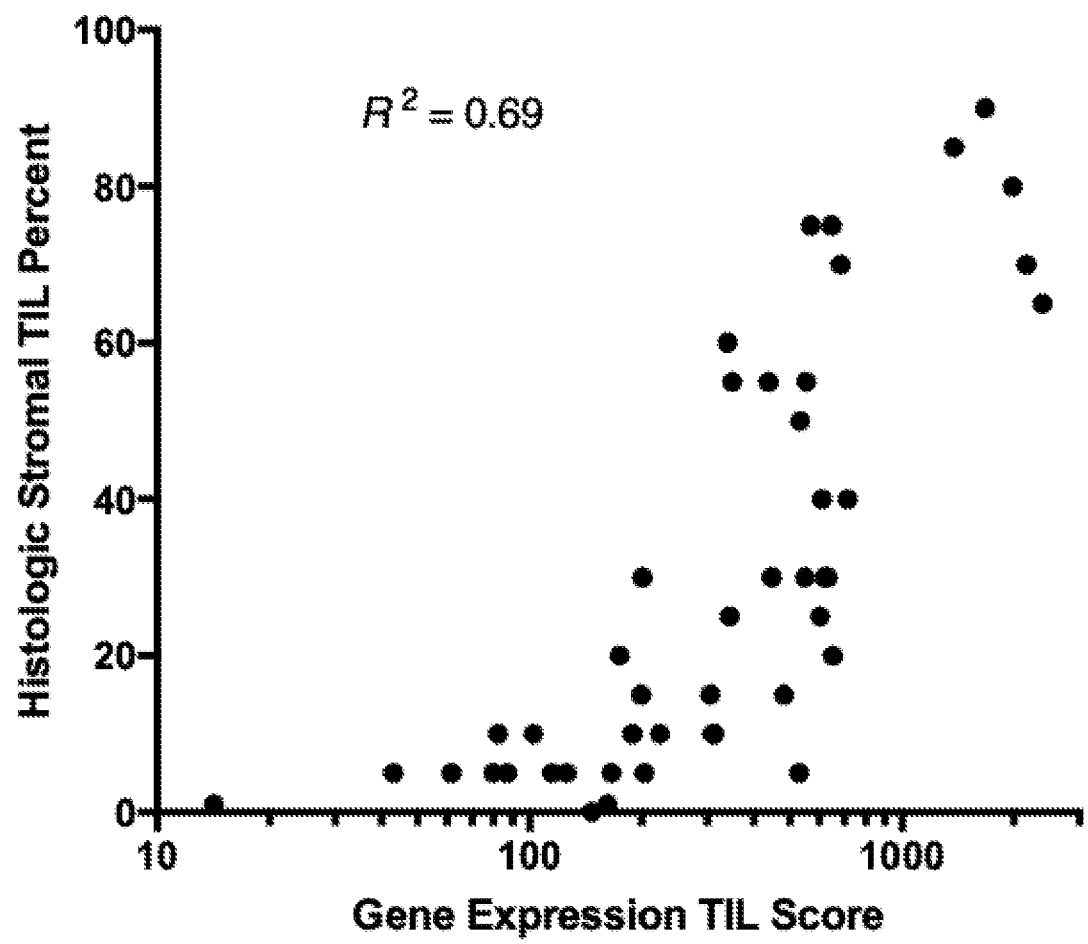

A cox proportional hazards model of the effect of stage alone in the validation cohort predicts that a patient diagnosed with Stage IIB disease has a 59% probability of 5-year disease free survival. A cox proportional hazards model including both stage and Immune Activation score predicts that a Stage IIB patient with a high Immune Activation Score of 4000 has an 79% probability of 5-year disease free survival, while a patient with the same disease stage and a low Immune Activation Score of 400 has a 32% probability of 5-year disease free survival. This suggested that a clinical decision-making tool that incorporated the Immune Activa- (Denkert C, et al. *Mod. Pathol.* 2016, 29, 1155-1164; Salgado R, et al. *Ann. Oncol.* 2015, 26, 259-271). The TIL Score measured by the MHCII Immune Activation assay was highly correlated with morphologic assessment of stromal TIL percentage (Spearman $R^2$=0.69, P<0.0001, FIG. 5B). These results confirmed that the MHCII Immune Activation assay on the Nanostring nCounter provides a standardized and multiplexed procedure for measuring MHCII expression and TILs in FFPE tumor specimens that is highly correlated with histologic assessments.

Example 8

Discussion

The purpose of this study was to develop and validate a multiplexed assay for MHCII and TIL gene expression that could be used on FFPE tissue to assess a TNBC patient's risk of recurrence. The results of this study demonstrated that performing the MHCII Immune Activation assay on FFPE tumor specimens using the Nanostring nCounter instrument provides accurate measurements of MHCII and TIL gene expression that are highly correlated with reduced risk of recurrence in TNBC patients with primary Stage I-III breast cancer.

Figure 12A:
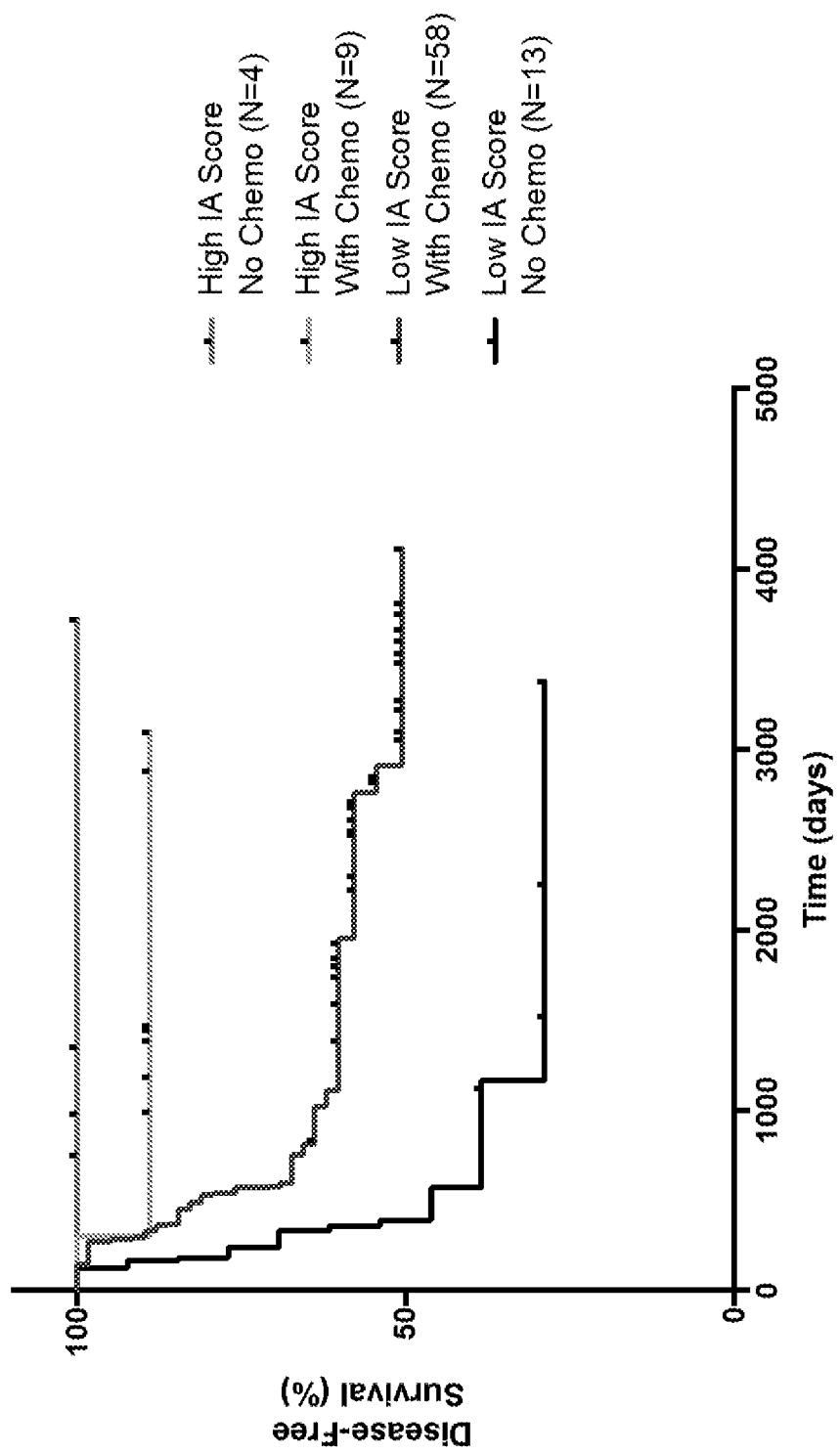
FIG. 12A, FIG. 12B.
Figure 12B:
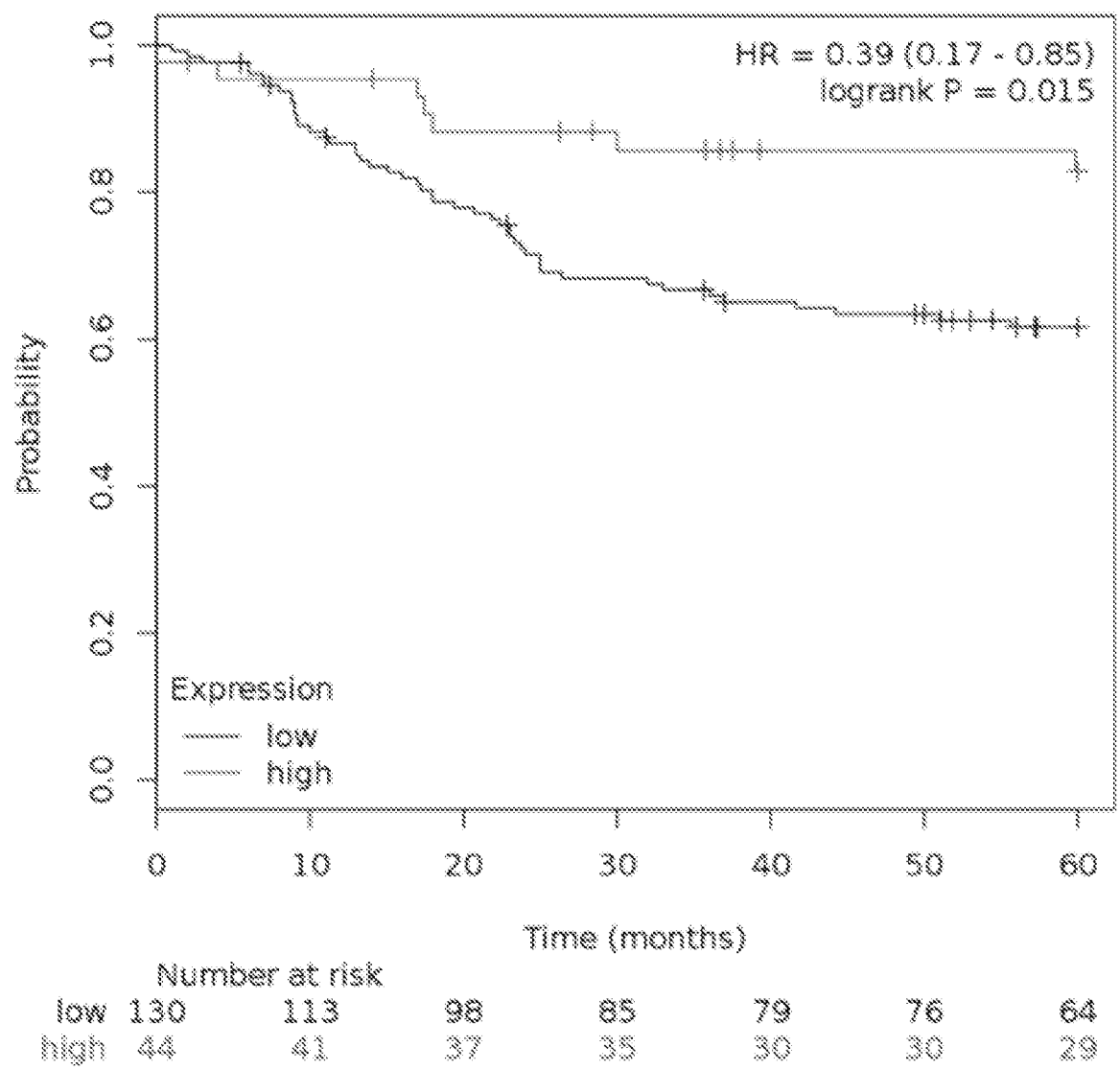

One use of the MHCII Immune Activation assay would be to distinguish TNBC patients who have a very low risk of relapse from those who have an average risk of relapse. We demonstrated that an Immune Activation Score threshold can be established to identify patients who have a very low risk of recurrence (FIG. 4A, FIG. 4B, FIG. 4C, FIG. 4D, FIG. 4E) and may not require systemic therapy. Both the training set and validation cohort in this study included patients who did not receive systemic chemotherapy for a variety of reasons including advanced age, comorbidities, and patient preference (TABLE 3). Those patients with high Immune Activation Scores who did not receive systemic chemotherapy did not relapse (FIG. 12A). To investigate this preliminary association further, we analyzed public microarray data from a larger cohort of patients with primary Stage I-III Basal-like breast cancer who did not receive systemic chemotherapy. We found that patients with higher expression of MHCII and TIL genes had significantly longer relapse-free survival, even without systemic treatment (FIG. 12B). The MHCII Immune Activation assay enables precision medicine for TNBC patients and could help reduce the burden of chemotherapy-induced side effects in TNBC survivors.

Another clinical application of the MHCII Immune Activation assay is predicting response to immunotherapy. Recent studies have shown that expression of MHC Class II molecules in melanoma cells is associated with improved response to anti-PD-1 immunotherapy in melanoma patients. Data presented at the American Society of Clinical Oncology 2017 annual meeting from the Phase 2 randomized, controlled, multi-center I-SPY 2 trial (NCT01042379) demonstrated that 60% of newly diagnosed TNBC patients achieved pathologic complete response (pCR) when treated with the immune checkpoint inhibitor pembrolizumab in combination with standard neoadjuvant chemotherapy. This was a significant improvement compared to the 20% of patients who achieved pCR with standard neoadjuvant chemotherapy alone. While this result is promising, it also indicates that 40% of TNBC patients in the pembrolizumab arm did not achieve pCR but were exposed to the significant risks associated with immunotherapy, which in this trial included autoimmune mediated adrenal insufficiency, hepatitis, colitis, and hypothyroidism. The MHCII Immune Activation assay may be used to identify patients that are most likely to benefit from immunotherapy.

The MHCII Immune Activation assay produces similar measurements as histologic assays for MHCII expression and TIL counting (FIG. 5A and FIG. 5B), but provides standardized methodology, a larger dynamic range of measurements, and multiplexed analysis of small specimens. The development of the Prosigna test for HR+ breast cancer has demonstrated that one key strength of assays developed on the NanoString nCounter is the ability to implement them as Laboratory Developed Tests (LDTs) in clinical laboratory sites across the world while maintaining standardized protocols and data analysis. The format of the MHCII Immune Activation assay will enable similar broad adoption as a clinical test for prognosis in TNBC patients, for which there are currently no clinical tests available.

Example 9

Immune Activation Score Compared to MHCII Score and TIL Score Alone

Figure 13A:
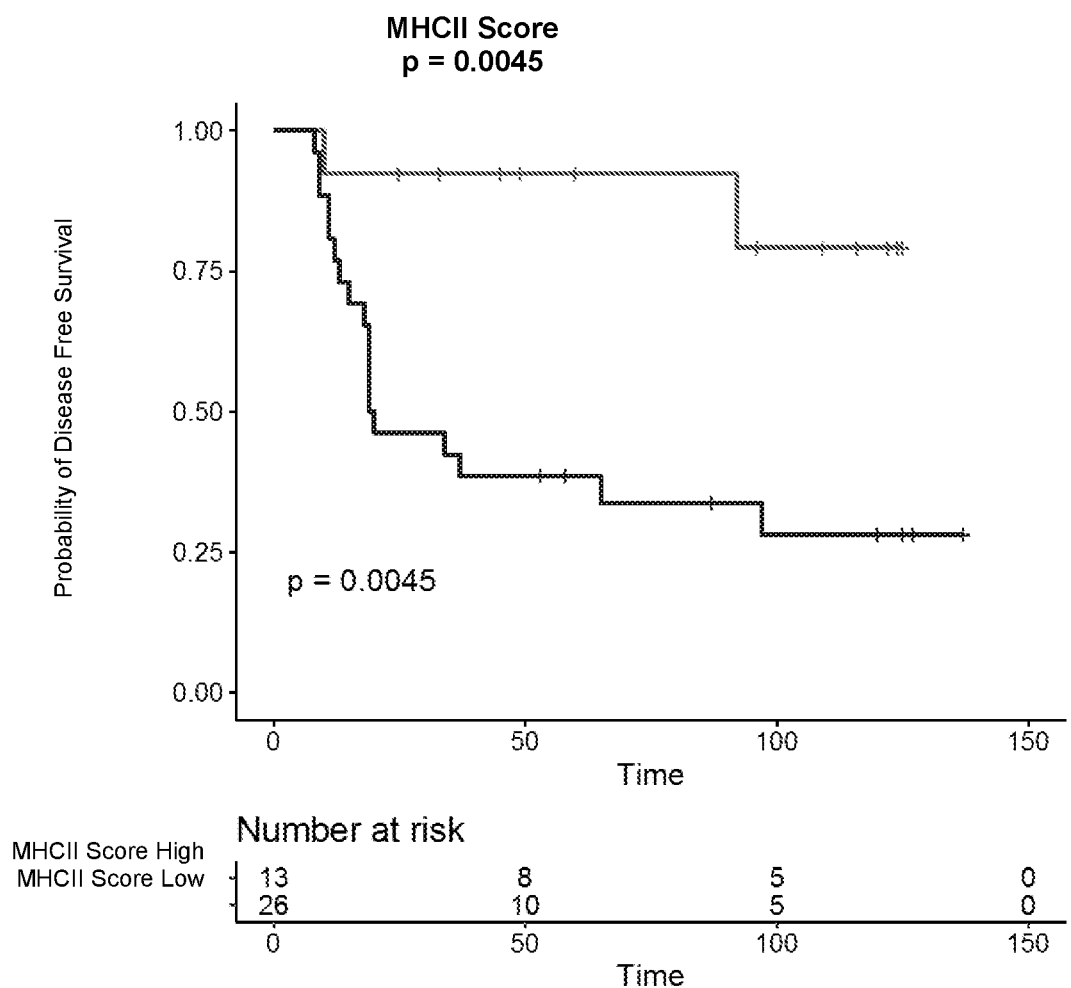
FIG. 13A, FIG. 13B, FIG. 13C. The MHCII Score (FIG. 13A) and the TIL Score (FIG. 13B) are both significantly associated with disease-free survival. The Immune Activation Score (FIG. 13C) is more significant than either score alone, indicating that incorporate both MHCII and TIL signature genes provides superior prognostic power.
Figure 13B:
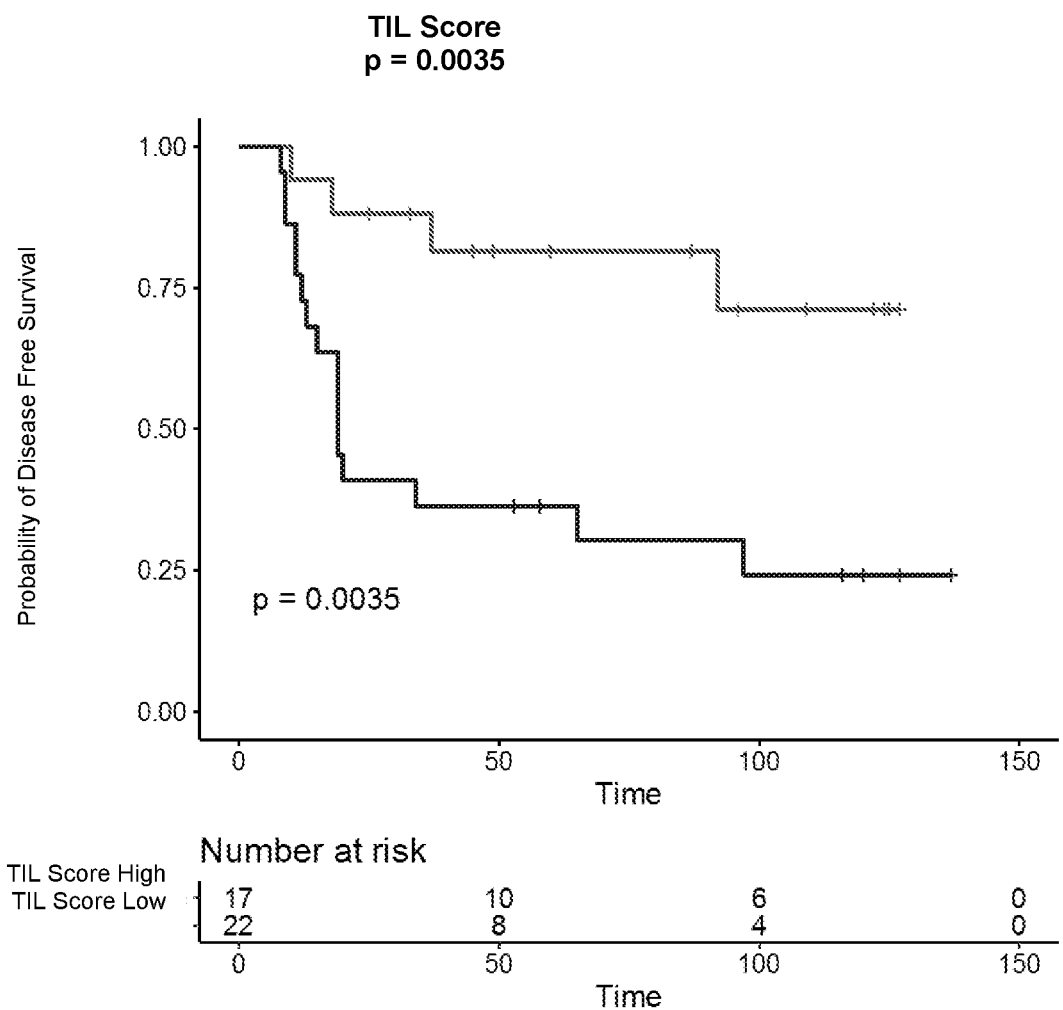
Figure 13C:
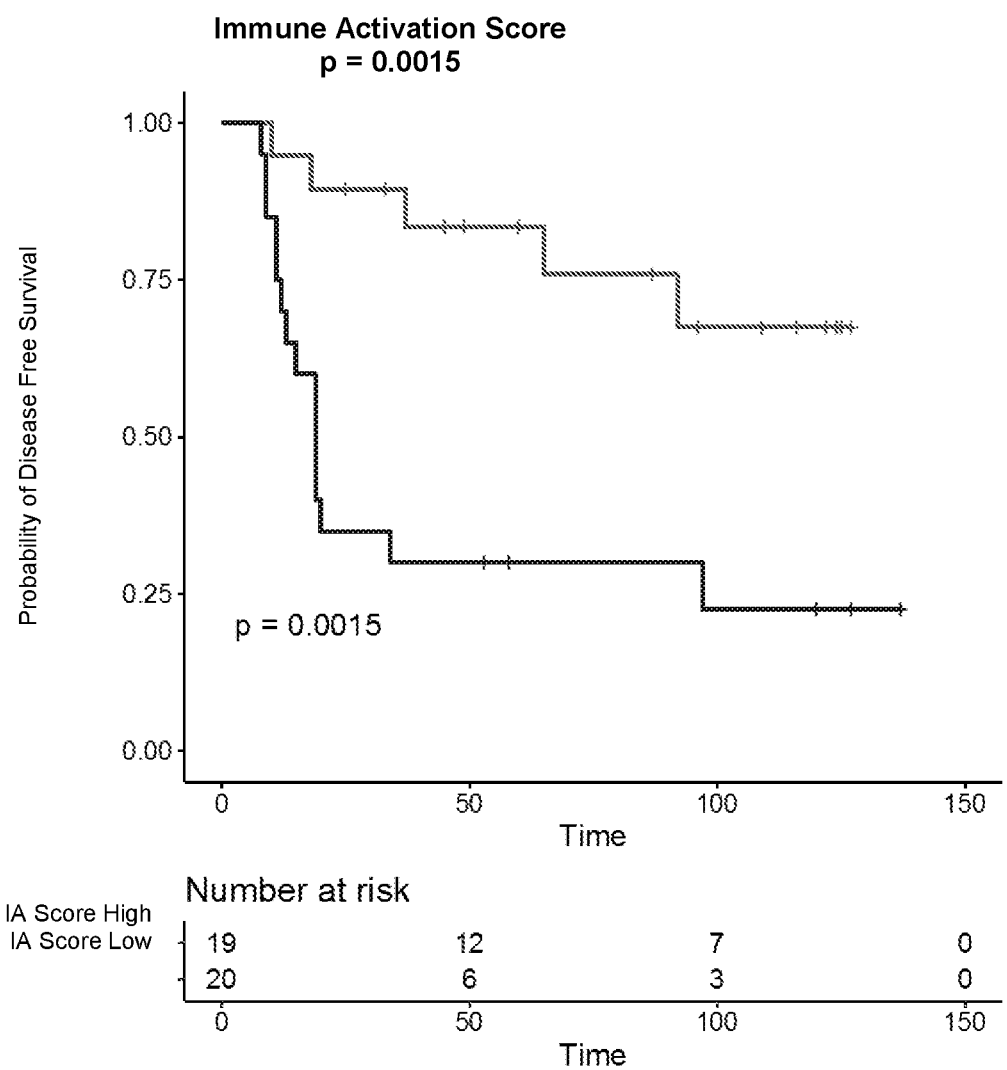

To determine if combining the MHCII Score and TIL Score into an Immune Activation Score improves the assessment of prognosis, Kaplan Meier plots using each score were created for patient samples in the training set. A Kaplan Meier curve using a threshold for MHCII Score that provides the most significant log rank p-value demonstrated a significant prognostic difference between tumors with high and low MHCII gene expression (log rank P=0.0045, FIG. 13A). A Kaplan Meier curve using a threshold for TIL Score that provides the most significant log rank p-value also demonstrated a significant prognostic difference between tumors with high and low TIL gene expression (log rank P=0.0035, FIG. 13B). Notably, when the MHCII Score and TIL Score were combined to generate an Immune Activation Score, a Kaplan Meier curve using a threshold that provides the most significant log rank p-value demonstrated a smaller p-value than either score alone, and more significant prognostic difference (log rank P=0.0015, FIG. 13C). This result suggested that the MHCII Score and TIL score are not redundant, and that the Immune Activation Score provides improved assessment of a patient's risk of recurrence compared to using either the MHCII Score or TIL Score alone. This was an unexpected result because MHCII expression in tumors and the presence of TILs are generally correlated across patient tumors. This result indicated the Immune Activation Score captures additional information about the co-occurrence of MHCII expression and TIL presence that is critical for more accurate assessment of prognosis.

Example 10

Three or More Genes in the Immune Activation Score

Figure 14:
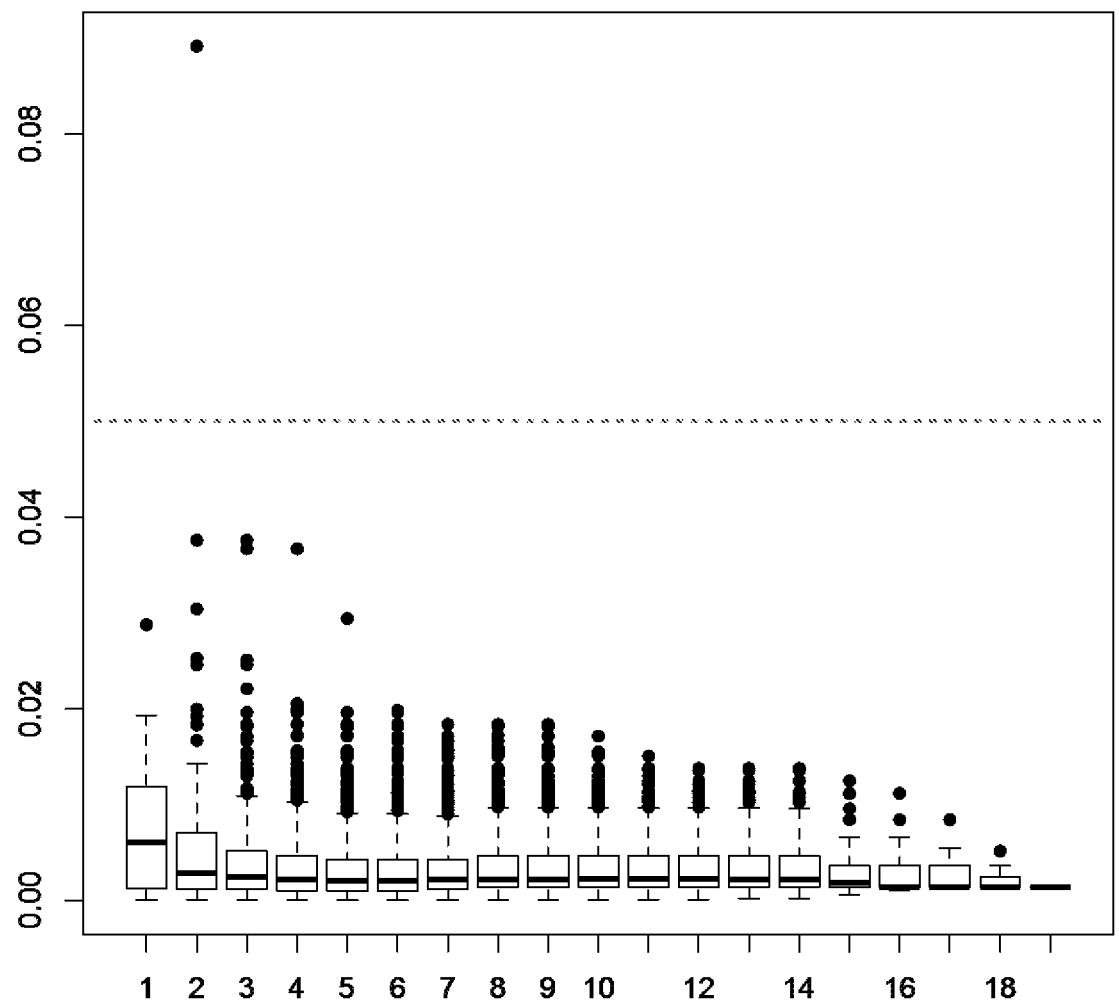
FIG. 14. All possible subsets of genes in the Immune Activation Score were tested for association with disease free survival in the training set. When any combination of 3 or more genes are included in the subsets a significant difference in long term disease-free survival is observed (log rank p-value<0.05).

To determine if particular subsets of genes in the MHCII Immune Activation Assay provide better or worse assessment of prognosis, all possible subsets of genes in the Immune Activation Score were tested for association with disease free survival in the training set. Each of the 19 genes in the Immune Activation Score were first analyzed individually. Kaplan Meier analysis was performed using a threshold for expression that provided the most significant log rank p-value. The log rank p-values for each individual gene in the Immune Activation Score were significant (<0.05) (FIG. 14). This process was repeated by calculating the geometric mean of the expression all possible pairs of two genes in the Immune Activation Score. Only 1 pair produced a non-significant log rank p-value>0.05 (CD69 and CD8A, p=0.89). This process was repeated for all possible combinations of 4 genes, 5 genes, 6 genes, etc. All possible combinations of 3 or more genes produced significant log rank p-values (<0.05, FIG. 14). Notably, as more genes were included in the analysis, the range and median of the p-values decreased (FIG. 14). This result indicated that including 3 or more genes in the Immune Activation Score allows detection of a significant prognostic difference between tumors with high and low scores, and including all 19 genes provides the best assessment of risk of recurrence.

Example 11

Immune Activation Score is Prognostic in Other Cancer Types

Figure 15A:
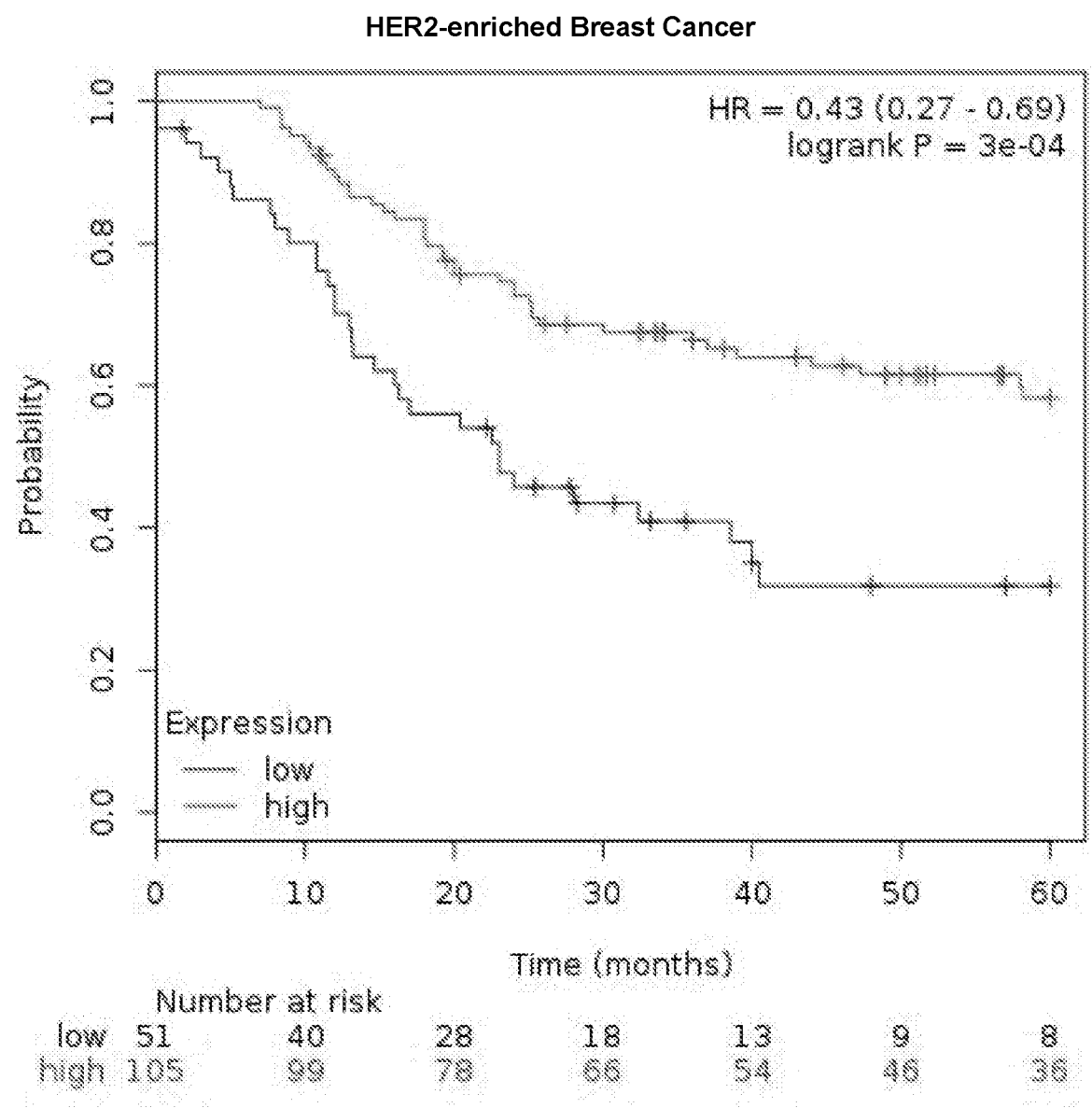
FIG. 15A, FIG. 15B, FIG. 15C, FIG. 15D. High Immune Activation scores are associated with significantly longer disease free survival in public microarray gene expression data from patients with HER2-enriched breast cancer (FIG. 15A), ovarian cancer (FIG. 15B), squamous lung cancer (FIG. 15C), and bladder cancer (FIG. 15D).
Figure 15B:
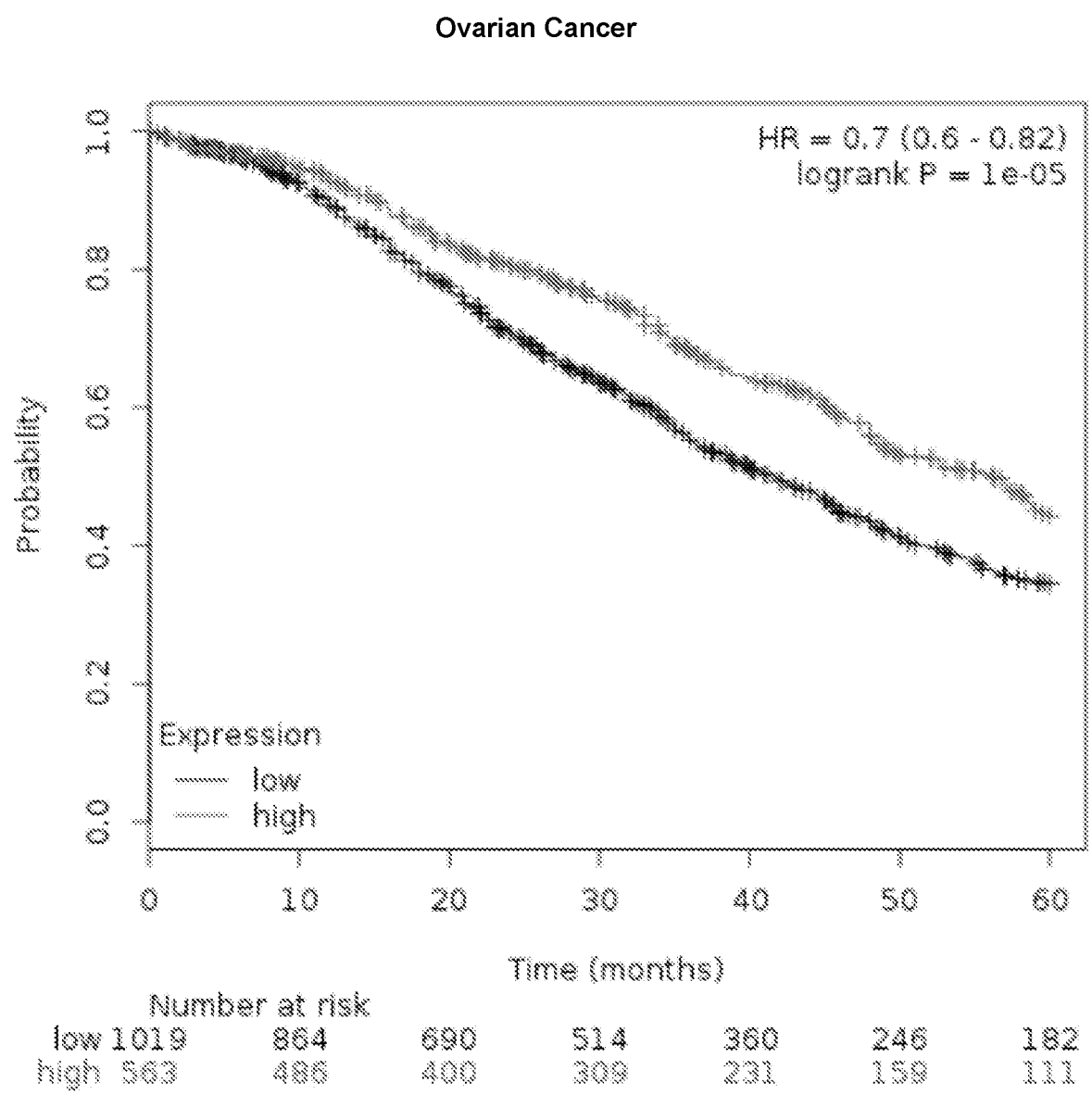
Figure 15C:
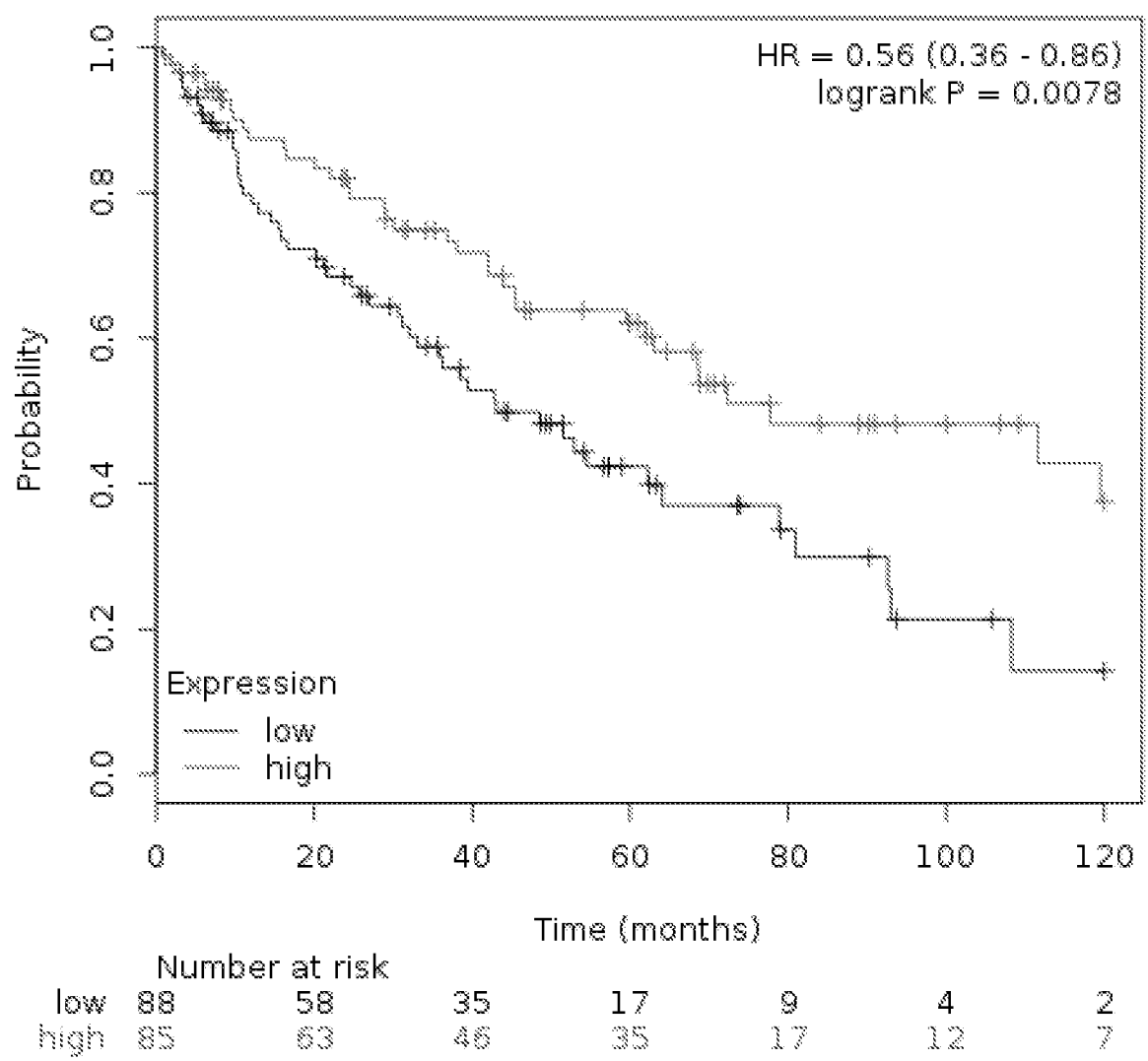
Figure 15D:
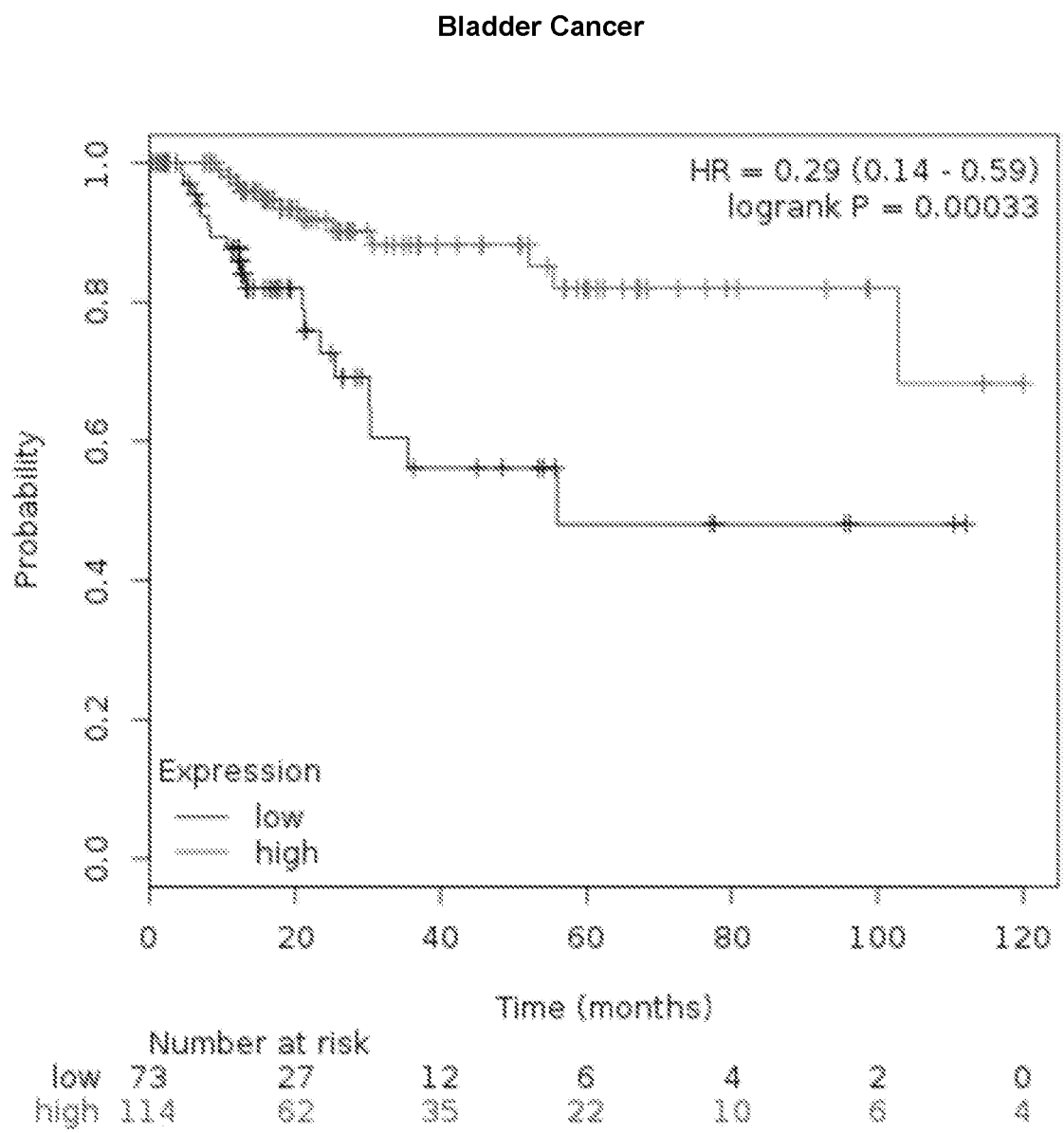

To determine if the expression of genes in the Immune Activation Score could be used to assess prognosis in other cancer types besides TNBC, public gene expression microarray data was analyzed from HER2-enriched breast cancer tumors, ovarian cancer, and squamous cell lung cancer (breast cancer source: Gyorffy B, et al. *Breast Cancer Res. Treatment* 2010, 123, 725-731; ovarian cancer source: Gyorffy B, et al. *Endocrine-Related Cancer* 2012, 19, 197-208; lung cancer source: Gyorffy B, et al. *PLoS One* 2013, 8, e82241). Kaplan Meier curves were generated using a threshold for MHCII Score that provided the most significant log rank p-value. In each of these diseases, higher expression of genes in the Immune Activation Score was associated with significantly longer disease-free survival. This result indicated that the Immune Activation Score could be used to assess prognosis in HER2-enriched breast cancer (FIG. 15A), ovarian cancer (FIG. 15B), squamous cell lung cancer (FIG. 15C), and bladder cancer (FIG. 15D).

Example 12

The Immune Activation Score Predicts Response to Immunotherapy in a Clinical Trial Gene expression microarray data from pre-treatment tumor biopsies was obtained from TNBC patients treated with neoadjuvant paclitaxel (chemotherapy, N=85) and TNBC patients treated with neoadjuvant paclitaxel plus pembrolizumab (immunotherapy, N=29).

Normalized gene expression values were obtained from Agilent 44K microarrays. All samples were analyzed on one of two Agilent custom designs (probe content version #15746 and probe content version #32627). Normalized data for each array was generated by centering the log 2 transformed gMeanSignal of all probes within the array to the 75th percentile of the ~21.1K probes shared between the two Agilent custom designs. A fixed value of 9.5 was then added to avoid negative values. Additional data preparation was also performed to account for the two platform arrays. For each platform, normalized expression data was collapsed, such that genes represented by multiple probes were computed as the average across probes. To combine data from the two platforms, the ComBat algorithm was then applied to adjust for platform-biases, and linear adjustment factors (per gene) were obtained from ComBat.

The MHCII Immune Activation Score was calculated using the mean normalized gene expression values for the following genes: CD74, HLA-DMA, HLA-DPA1, HLA-DQA1, ARHGAP9, CD3D, IFNG, IL7R, PDCD1.

Figure 16A:
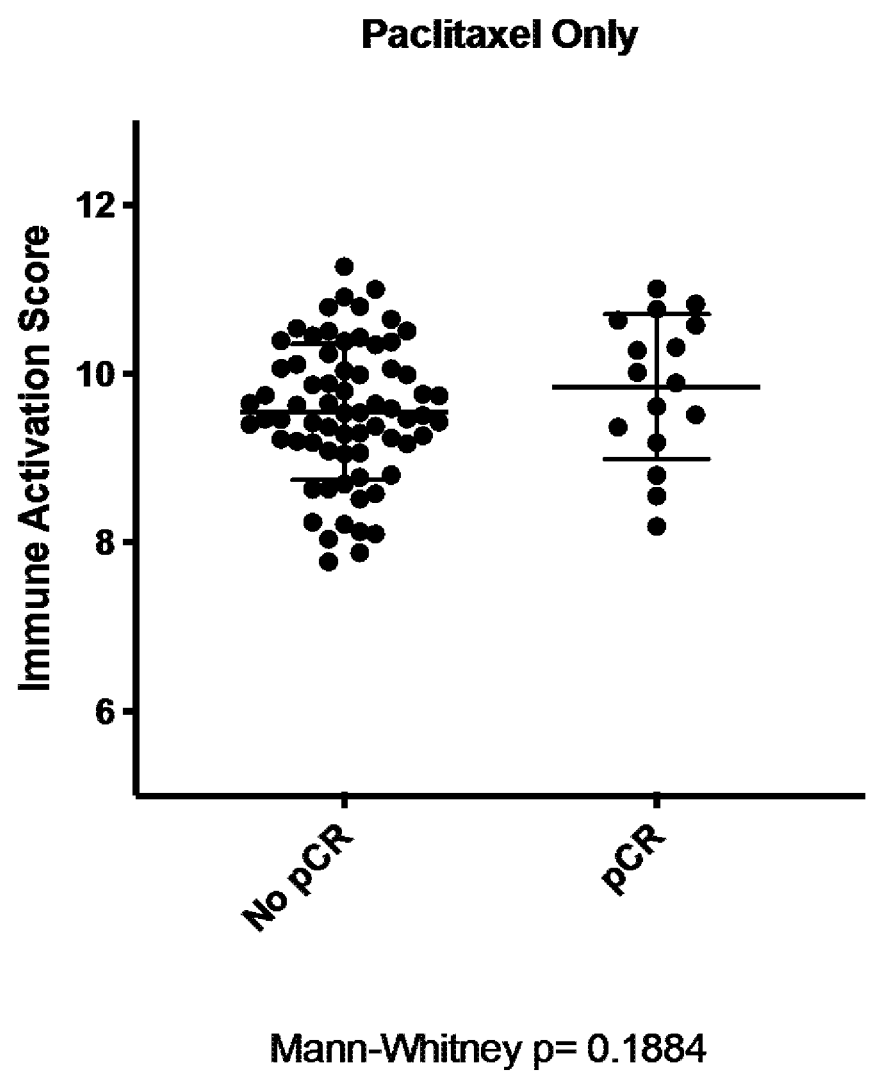
FIG. 16A, FIG. 16B, FIG. 16C. Comparison of Immune Activation Scores between patients who achieve pathologic complete response (pCR) and those who did not (No pCR) among patients who were treated with neoadjuvant paclitaxel alone (FIG. 16A), and patients treated with neoadjuvant paclitaxel and pembrolizumab (FIG. 16B). Patients with high Immune Activation Scores (above 9.7, red points) were more likely to achieve pCR than those with low immune activation scores when their treatment included pembrolizumab (FIG. 16B). An ROC curve demonstrated that Immune Activation Scores were predictive of pCR with paclitaxel plus pembrolizumab treatment with an area under the curve (AUC) of 82.6% (FIG. 16C).
Figure 16B:
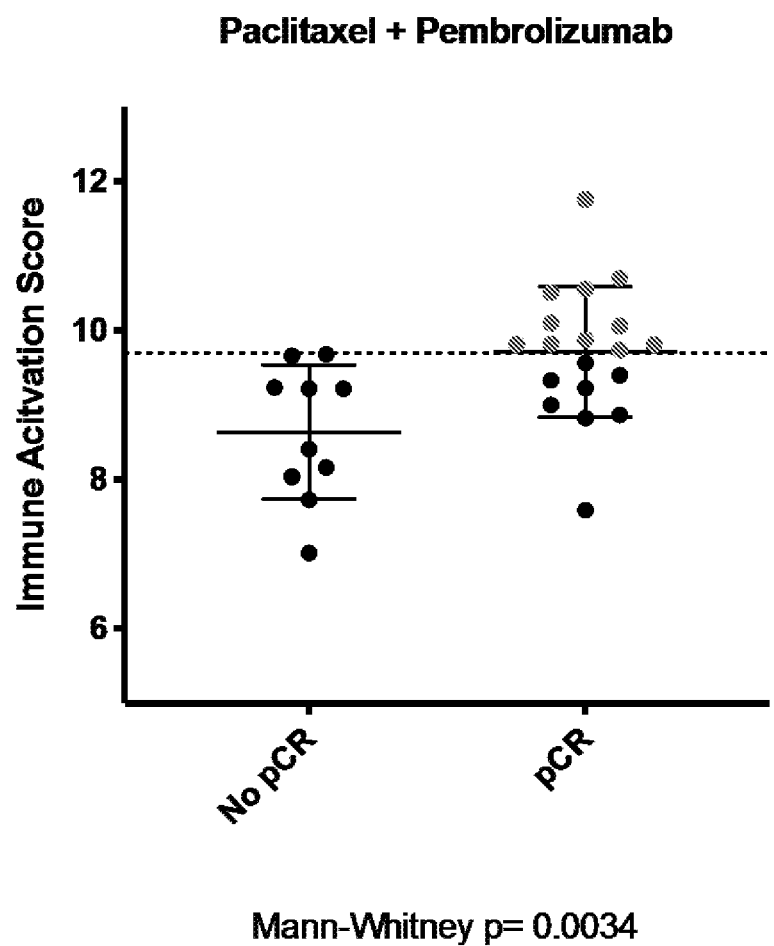
Figure 16C:
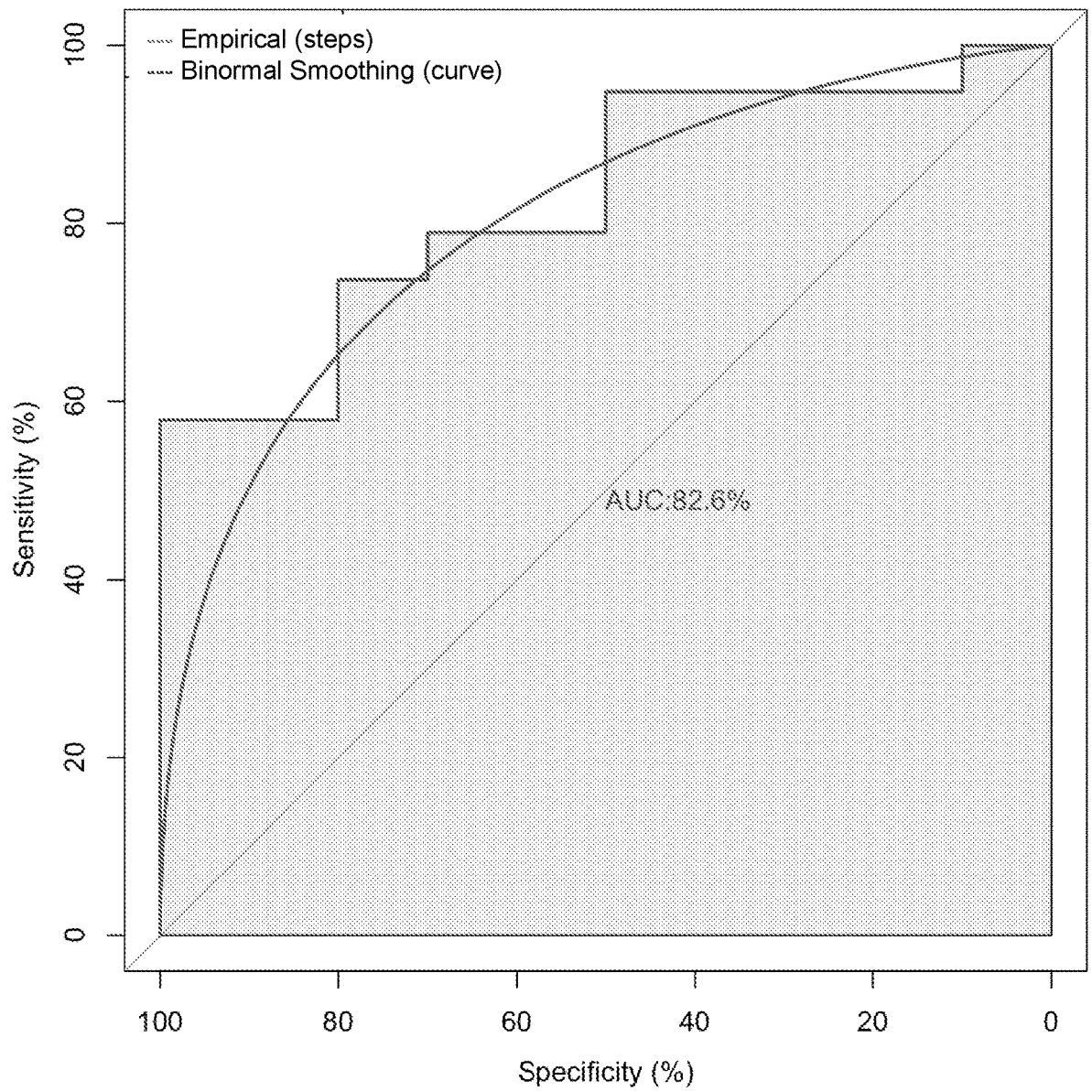

MHCII Immune Activation Scores were compared between patients who achieved pathological complete response (pCR) after treatment to those who did not (No pCR) in each treatment group (FIG. 16A, FIG. 16B, FIG. 16C). There was no significant difference in the Immune Activation Scores between patients who achieved pCR and those who did not among patients who were treated with paclitaxel alone (Mann-Whitney p=0.1884) (FIG. 16A). Among patients who were treated with both paclitaxel and pembrolizumab, those who achieve pCR had significantly higher Immune Activation scores than those who did not achieve pCR (FIG. 16B). ROC curve analysis indicated that high Immune Activation Scores are associated with pCR when patients are treated with paclitaxel plus pembrolizumab (FIG. 16C) (Area Under the Curve=82.6%). Furthermore, applying a threshold of 9.7 to this immune activation score calculation provided 100% specificity and 58% sensitivity for identifying patients with high Immune Activation Scores who will achieve pCR when treated with paclitaxel plus pembrolizumab (FIG. 16B). Together these results indicate that patients with high Immune Activation Scores are more likely to achieve pCR when their treatment includes immunotherapy.

Example 13

Prognostic Significance in High Risk Patients Treated with Uniform Regimens

RNA was isolated from breast cancer FFPE specimens (2×1 mm FFPE Cores) from the GEICAM/9906 clinical trial, a multicenter randomized phase III study evaluating adjuvant chemotherapy in high-risk node-positive operable breast cancer patients.

Previous PAM50 subtyping analysis by RT-qPCR of RNA from these specimens was used to select tumor specimens that were classified into the Basal-like molecular subtype. Thirty-nine (65%) of the patients were treated with fluorouracil, epirubicin, and cyclophosphamide (FEC), and 21 (35%) patients received FEC followed by paclitaxel (FEC-P). Median follow-up was 9.7 years.

Figure 17A:
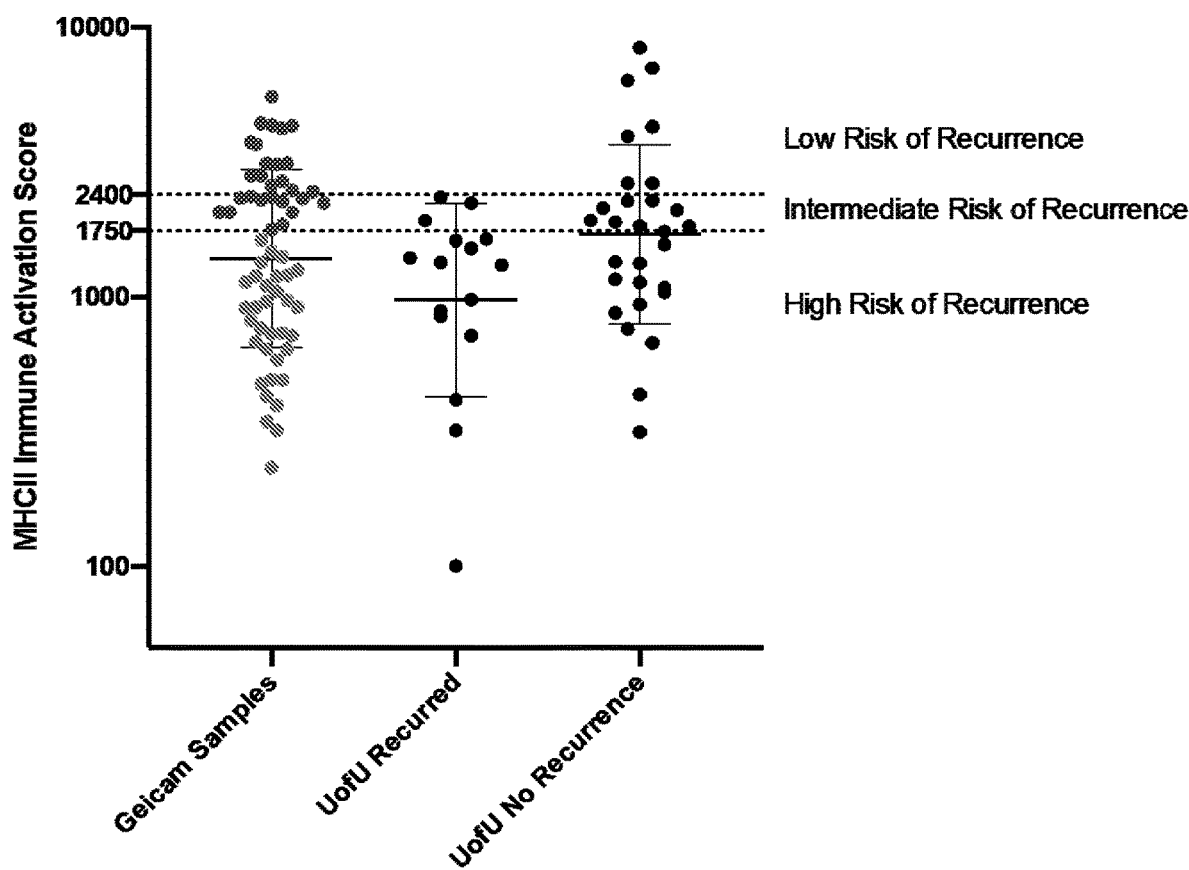
FIG. 17A, FIG. 17B, FIG. 17C, FIG. 17D. The MHCII Immune Activation assay was applied to basal-like breast cancer samples from the GEICAM/9906 clinical trial, which categorized 28 out of 60 (46.6%) patient into a low+ intermediate Risk of Recurrence group (low+interm-ROR) based on high MHCII Immune Activation Scores using pre-specified thresholds (blue dots) (FIG. 17A). Across both arms of the trial, patients with high MHCII Scores (low+ interm-ROR) had significantly longer DFS (log-rank p=0.008, Likelihood Ratio Test (LRT) p=0.0081) (FIG. 17B). In the FEC arm, patients with high MHCII Score (low+interm-ROR) showed a trend toward longer DFS, but it was not significant (log-rank p=0.164, LRT p=0.1595) (FIG. 17C). In the FEC-P arm, patients with high MHCII Scores (low+interm-ROR) had significantly longer DFS (log-rank p=0.01, LRT p=0.0111) (FIG. 17D).
Figure 17B:
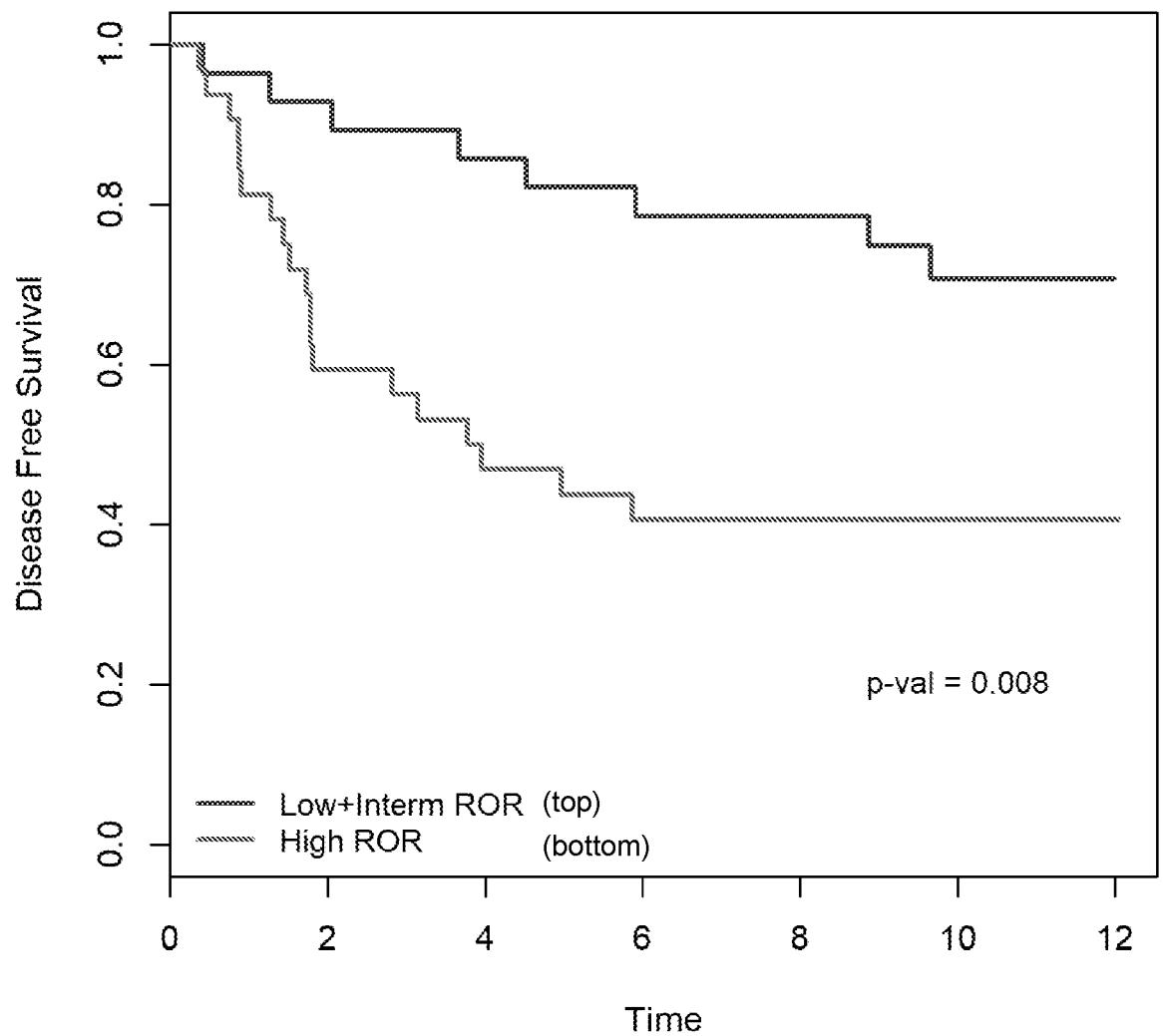

The MHCII Immune Activation assay was applied to these samples, as detailed in Examples 2-4. Patients were categorized into a low or intermediate Risk of Recurrence (low+interm-ROR) group based on high MHCII Immune Activation Score using pre-specified thresholds, as detailed in Examples 2-6 (FIG. 17A). A total of 28 out of 60 (46.6%) Basal-like patients were classified into the low+interm-ROR group. Across both arms of the trial, patients with high MHCII Score (low+interm-ROR group) had significantly longer DFS (FIG. 17B) (Likelihood Ratio Test (LRT) p=0.0081). This result indicates that the MHCII Immune Activation assay can be applied to RNA extracted from FFPE tumor block punches to assess risk of recurrence in Basal-like breast cancer patients.

Figure 17C:
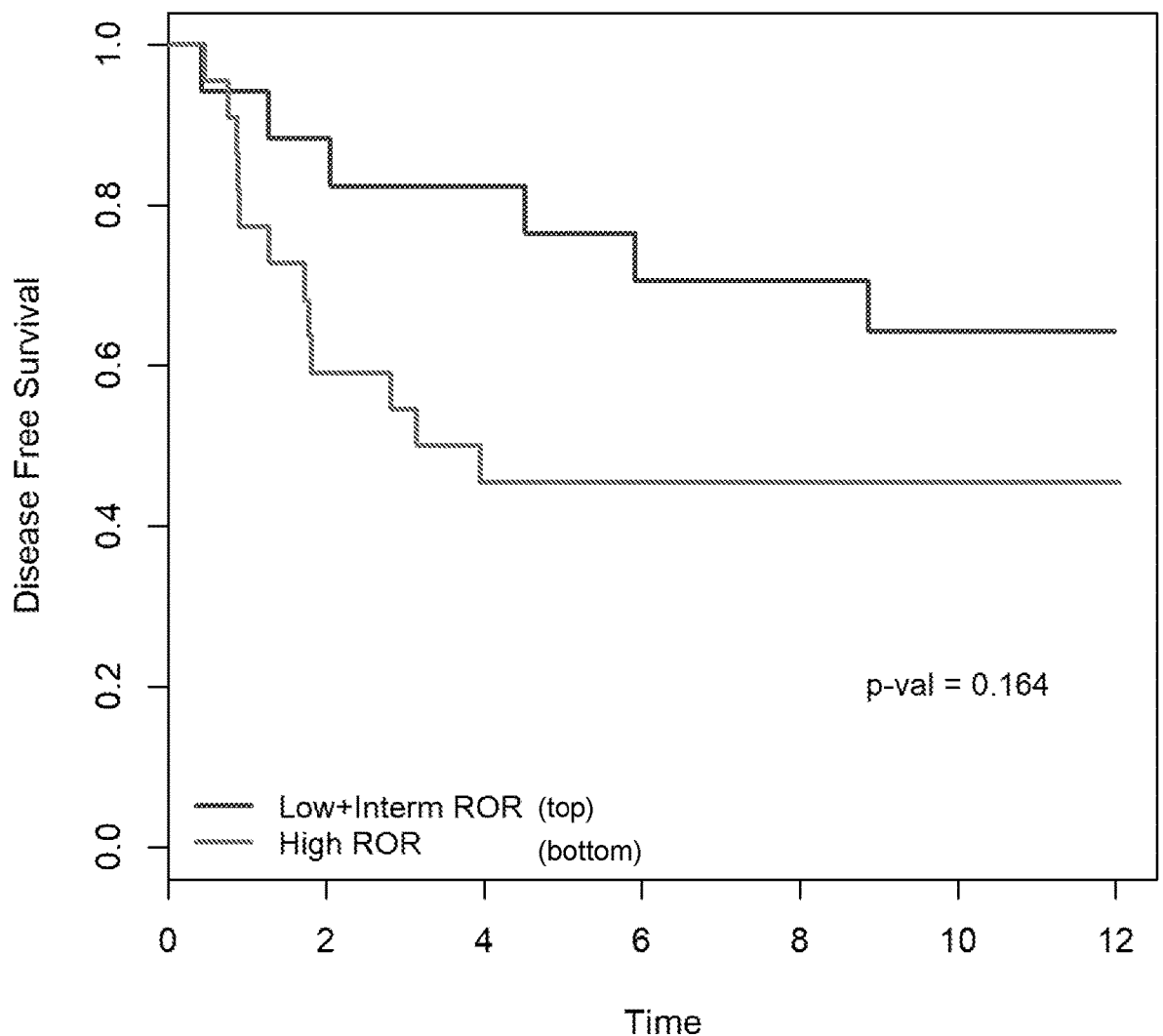
Figure 17D:
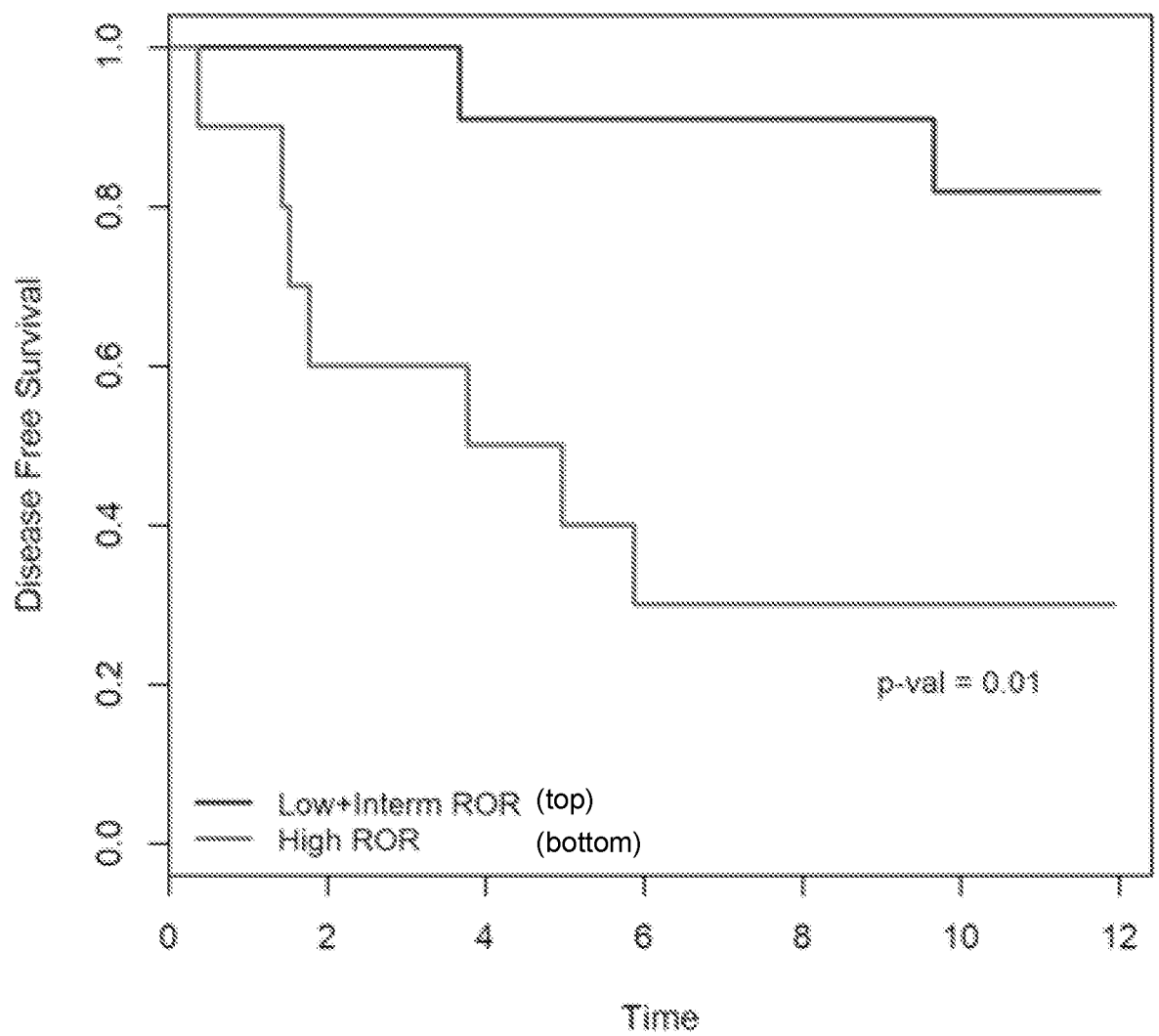

In the FEC arm, patients with high MHCII Score (low+interm-ROR group) showed a trend toward longer DFS than patients with lower MHCII scores (high-ROR group), but it was not significant (LRT p=0.1595, log-rank p=0.164) (FIG. 17C). In the FEC-P arm, patients with high MHCII Score (low+interm-ROR group) did have significantly longer DFS than patients with lower MHCII scores (high-ROR group) (LRT p=0.0111; log-rank p=0.01) (FIG. 17D). These results indicate that the MHCII Immune Activation Score is inversely associated with risk of recurrence in Basal-like breast cancer patients treated with uniform adjuvant chemotherapy regimens. Furthermore, the association between disease-free survival and MHCII Immune Activation Score was stronger when patients were treated with chemotherapy regimens that include paclitaxel. This suggests that patients with high MHCII Immune Activation Scores benefit from including paclitaxel in their treatment regimen.

Example 14

MHCII Immune Activation Score Calculations Using RNA-seq Gene Expression Data are Associated with Overall Survival and Event-Free Survival in a Clinical Trial of Neoadjuvant Docetaxel-Carboplatin in TNBC Patients RNA-seq data was provided from breast cancer patient tumors collected prior to treatment from patients enrolled in a clinical trial of neoadjuvant docetaxel and carboplatin (Sharma P, et al. Clin. Cancer Res. 2017, 23, 649-657). The data were generated in a manner known in the art. Briefly, RNA-seq data was aligned using STAR 2.7.1a and expression levels were quantified with Salmon v0.14.0. and gathered into the expression matrix using R package tximport. No normalization or correction was performed. As reference, gencode version 29 (genome GRCh38.p12, ALL regions) was used.

Two genes in the algorithm were not provided in the RNA-seq data (HLA-DRB6 and HLA-DPB2), and three genes (HLA-DRB5, HLA-DRQA1, and HLA-DRB1) were excluded because they did not correlate with other co-regulated MHCII genes using the approach described in Example 4 (FIG. 9A). Previous analyses demonstrated that the algorithm can produce prognostic results using a subset of genes (FIG. 14), so the MHCII Score was calculated as the geometric mean of the following genes: CD74, CIITA, CTSH, HLA-DMA, HLA-DMB, HLA-DPA1, HLA-DPB1, and NCOA1. The TIL Score was calculated as the geometric mean of the following genes: CD274, ARHGAP9, CD3D, CD4, CD69, CD8A, IFNG, IL7R, and PDCD1. The MHCII Immune Activation Score was calculated as the geometric mean of the MHCII Score and the TIL Score as detailed in Examples 2-6.

The MHCII Immune Activation Scores were analyzed for 141 patients whose tumors were previously classified into the Basal-like molecular subtype using PAM50 subtyping. The log 10 MHCII Immune Activation score was significantly inversely associated with Symmans response using logistic regression comparing pCR vs RCB-I/RCB-II/RCB-III ($p=0.024$) and comparing pCR/RCB-I vs. RCB-II/RCB-III ($p=0.022$). This result indicates that patients with high MHCII Immune Activation Score are more likely to respond to neoadjuvant docetaxel and carboplatin.

Figure 18:
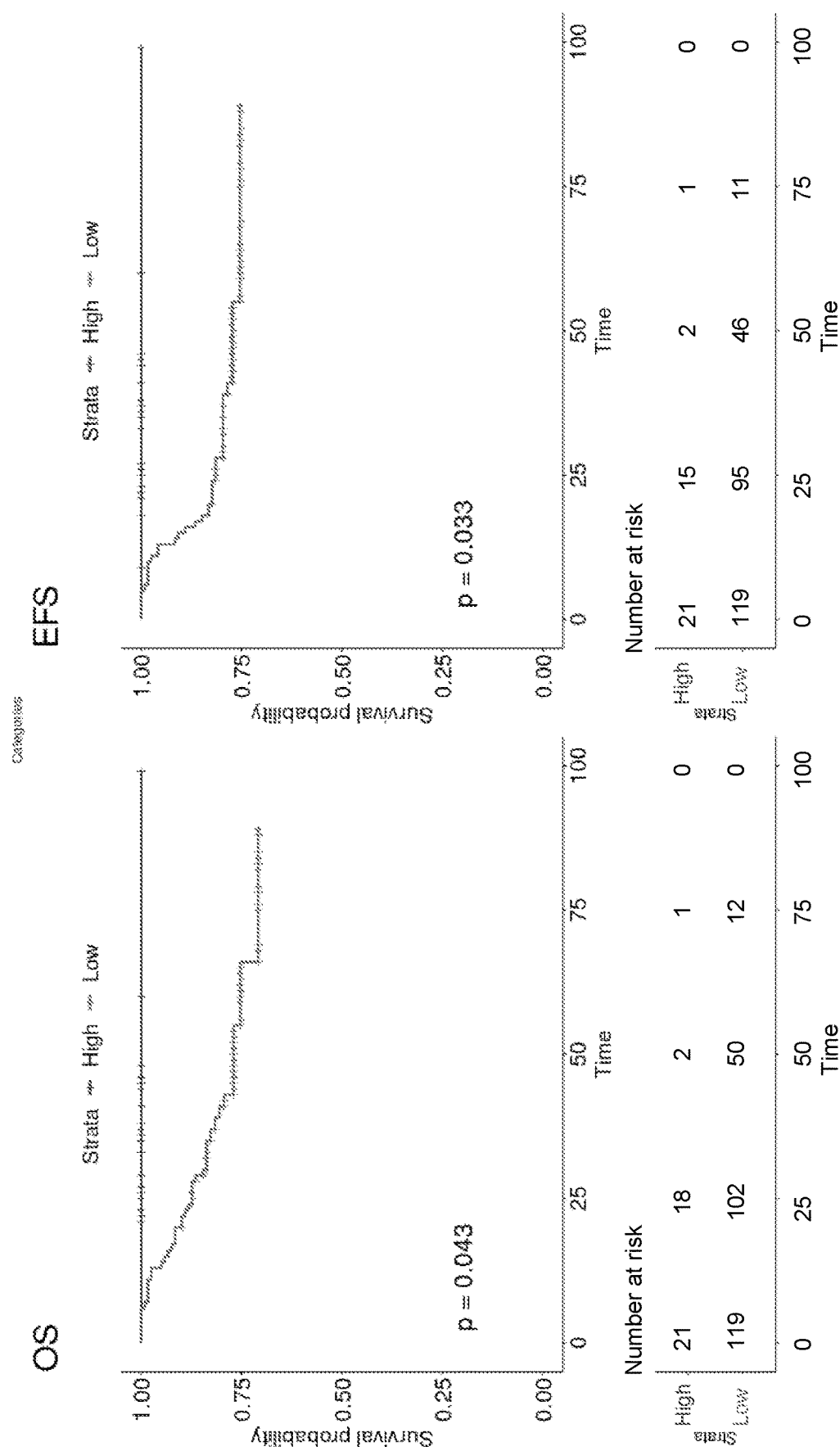
FIG. 18. MHCII Immune Activation scores were calculated from RNA-seq data from basal-like breast cancer samples obtained from patients enrolled in a clinical trial of neoadjuvant docetaxel and carboplatin. Patients whose MHCII Immune Activation Scores were in the top 15% highest scores (85th percentile) (High) had significantly longer overall survival (OS) and event free survival (EFS) than patients with lower MHCII Immune Activation Scores. Time is shown in months.

It was also found that patients whose MHCII Immune Activation Scores were in the top 15% highest scores (85th percentile) had significantly longer overall survival (log-rank $p=0.043$) and event free survival (log-rank $p=0.033$) (FIG. 18). More specifically, none of the patients who had high MHCII Immune Activation Score experienced recurrence or death from disease during the study follow-up time (maximum 100 months) (FIG. 18).

Together these results indicate that patients with high MHCII Immune Activation Scores are more like to respond to neoadjuvant docetaxel and carboplatin, and more likely to experience long-term disease-free survival, compared to patients with low MHCII Immune Activation Scores. This suggests that patients with high MHCII Immune Activation Scores benefit from treatment with neoadjuvant docetaxel and carboplatin.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of determining the risk of recurrence of cancer in a subject, the method comprising: determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1; calculating a normalized expression level of each MHCII gene by multiplying the determined level of expression of each MHCII gene by the Normalization Factor for the subject; calculating a MHCII Score for the subject, wherein the MHCII Score is the geometric mean of the normalized expression levels of the MHCII genes; determining the level of expression in the subject of at least one TIL gene selected from CD3D, CD4, CD8A, CD69, IFNG, IL7R, PDCD1, CD274, and ARHGAP9; calculating a normalized expression level of each TIL gene by multiplying the determined level of expression of each TIL gene by the Normalization Factor for the subject; calculating a TIL Score for the subject, wherein the TIL Score is the geometric mean of the normalized expression levels of the TIL genes; determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

Clause 2. The method of clause 1, wherein the Housekeeping Control is the arithmetic mean of the Housekeeping Scores for a set of control samples, and wherein the control samples are from other subjects with cancer.

Clause 3. The method of any one of clauses 1-2, wherein the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity.

Clause 4. The method of any one of clauses 1-3, wherein the level of expression in the subject of each Housekeeping gene selected from ACTB, MRPL19, RPLP0, PSMC4, and SF3A1 is determined.

Clause 5. The method of any one of clauses 1-4, wherein the level of expression of each MHCII gene is determined and the level of expression of each TIL gene is determined.

Clause 6. The method of any one of clauses 1-5, wherein the level of expression of the genes is determined using a NanoString nCounter platform, and wherein the subject is determined to have an increased risk of cancer recurrence when the Immune Activation Score is less than a threshold value, and that the subject has a decreased risk of cancer recurrence when the Immune Activation Score is greater than or equal to the threshold value, wherein the threshold value is at least about 1750, at least about 2000, or at least about 2400.

Clause 7. The method of any one of clauses 1-5, wherein the subject is determined to have a high risk of cancer recurrence when the Immune Activation Score is less than a first threshold value, and that the subject has a decreased or a median risk of cancer recurrence when the Immune Activation Score is greater than or equal to the first threshold value and less than a second threshold value, and that the subject is determined to have a low risk of cancer recurrence when the Immune Activation Score is greater than or equal to the second threshold value.

Clause 8. The method of any one of clauses 1-7, the method further comprising administering chemotherapy to the subject determined to have an increased risk or a high risk of cancer recurrence.

Clause 9. The method of any one of clauses 1-7, the method further comprising abstaining from administering chemotherapy to the subject determined to have a decreased risk or a low risk of cancer recurrence.

Clause 10. The method of any one of clauses 1-7, the method further comprising administering immunotherapy to the subject determined to have a decreased risk or a low risk of cancer recurrence.

Clause 11. A method of diagnosing a subject with triple-negative breast cancer (TNBC) as having TNBC Basal-like subtype, the method comprising: determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one Basal-like gene selected from FOXC1, MKI67, CDC20, CCNE1, and ORC6; calculating a normalized expression level of each Basal-like gene by multiplying the determined level of expression of each Basal-like gene by the Normalization Factor for the subject; calculating a Basal-like Subtype Score for the subject, which is the geometric mean of the normalized expression levels of the Basal-like genes; determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score.

Clause 12. The method of clause 11, wherein the control Basal-like Subtype Score is the arithmetic mean of Basal-like Subtype Scores for a set of samples from other subjects with breast cancer.

Clause 13. The method of clause 11 or 12, wherein the level of expression of the genes is determined using a NanoString nCounter platform, and wherein the subject is determined to have TNBC Basal-like subtype when the Basal-like Subtype Score for the subject is greater than or equal to 350, and that the subject does not have TNBC Basal-like subtype when the Basal-like Subtype Score for the subject is less than 350.

Clause 14. The method of any one of clauses 11-13, further comprising determining the risk of recurrence of cancer in the subject according to any one of clauses 1-7 when the subject is determined to have TNBC Basal-like subtype.

Clause 15. A method of treating cancer in a subject, the method comprising: determining an Immune Activation Score for the subject that is less than a control Immune Activation Score according to any one of clauses 1-6; and administering chemotherapy to the subject determined to have an increased risk of cancer recurrence.

Clause 16. A method of treating cancer in a subject, the method comprising: determining an Immune Activation Score for the subject that is greater than or equal to a control Immune Activation Score according to any one of clauses 1-6; and administering immunotherapy to the subject determined to have a decreased risk of cancer recurrence.

Clause 17. A method of diagnosing a subject with triple-negative breast cancer (TNBC) as having TNBC Basal-like subtype and determining the risk of recurrence of cancer in the subject, the method comprising: determining the level of expression in the subject of at least one Housekeeping gene selected from ACTB, MRPL19, RPLP0, PSMC4, and SF3A1; calculating a Housekeeping Score for the subject, which is the geometric mean of the expression levels of the Housekeeping genes; calculating a Normalization Factor for the subject, which is a Housekeeping Control divided by the Housekeeping Score for the subject; determining the level of expression in the subject of at least one Basal-like gene selected from FOXC1, MKI67, CDC20, CCNE1, and ORC6; calculating a normalized expression level of each Basal-like gene by multiplying the determined level of expression of each Basal-like gene by the Normalization Factor for the subject; calculating a Basal-like Subtype Score for the subject, which is the geometric mean of the normalized expression levels of the Basal-like genes; determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score; determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1; calculating a normalized expression level of each MHCII gene by multiplying the determined level of expression of each MHCII gene by the Normalization Factor for the subject; calculating a MHCII Score for the subject, wherein the MHCII Score is the geometric mean of the normalized expression levels of the MHCII genes; determining the level of expression in the subject of at least one TIL gene selected from CD3D, CD4, CD8A, CD69, IFNG, IL7R, PDCD1, CD274, and ARHGAP9; calculating a normalized expression level of each TIL gene by multiplying the determined level of expression of each TIL gene by the Normalization Factor for the subject; calculating a TIL Score for the subject, wherein the TIL Score is the geometric mean of the normalized expression levels of the TIL genes; determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

Clause 18. The method of clause 17, wherein the control Basal-like Subtype Score is the arithmetic mean of Basal-like Subtype Scores for a set samples from other subjects with breast cancer.

Clause 19. The method of clause 17 or 18, wherein the Housekeeping Control is the arithmetic mean of the Housekeeping Scores for a set of control samples, and wherein the control samples are from other subjects with cancer.

Clause 20. The method of any one of clauses 17-19, wherein the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity.

Clause 21. The method of any one of the above clauses, wherein the level of expression for the gene is determined by measuring the level of RNA.

Clause 22. The method of clause 21, wherein the level of RNA is measured using a NanoString nCounter platform.

Clause 23. The method of any one of the above clauses, wherein the level of expression in a sample from the subject is determined.

Clause 24. The method of clause 23, wherein the sample comprises tissue or blood.

Clause 25. The method of clause 23, wherein the sample comprises tumor tissue.

Clause 26. The method of any one of clauses 1-10, 15, and 21-25, wherein the cancer comprises breast cancer, ovarian cancer, bladder cancer, or lung cancer.

Clause 27. The method of clause 26, wherein the breast cancer is triple-negative breast cancer (TNBC).

Clause 28. The method of clause 26, wherein the breast cancer is HER2-enriched breast cancer.

Clause 29. The method of clause 26, wherein the lung cancer is squamous cell lung cancer.

| SEQUENCES | |
| --- | --- |
| Target Sequence | Target SEQ ID NO. |
| TGCAGAAGGAGATCACTGCCCTGGCACCCAGCACAATGAAGATCAAGATCATTGCTCCTCCTGAGCGCAAGTACTCCGTGTGGATCGGCGGCTCCATCCT | 1 |
| TGACTGTCTCTATCTTCATGAGTGTGACTTGAGGTGTTGGGATGGGTGAGGGAGCTTCTCTAAAGAGGAAAGTGAGTGGATTAACCCCTGCTTCTCTTCT | 4 |
| CCTCCAGACACCAGTGCGTGCTCCCGATGCTGCTATGGAAGGTGCTACTTGACCTAAGGGACTCCCACAACAACAAAAGCTTGAAGCTGTGGAGGGCCAC | 7 |
| AGCTTCCCGAGGCTCCGCACCAGCCGCGCTTCTGTCCGCCTGCAGGGCATTCCAGAAAGATGAGGATATTTGCTGTCTTTATATTCATGACCTACTGGCA | 10 |
| TATCTACTGGATGAGTTCCGCTGGGAGATGGAACATAGCACGTTTCTCTCTGGCCTGGTACTGGCTACCCTTCTCTCGCAAGTGAGCCCCTTCAAGATAC | 13 |
| TGGCAGGCGGAGAGGGCTTCCTCCTCCAAGTCTTGGATCACCTTTGACCTGAAGAACAAGGAAGTGTCTGTAAAACGGGTTACCCAGGACCCTAAGCTCC | 16 |
| AGGACATGAACTTTCTAAAACGATACGCAGGTAGAGAGGAACACTGGGTTGGACTGAAAAAGGAACCTGGTCACCCATGGAAGTGGTCAAATGGCAAAGA | 19 |
| TTCAGCCCCCAGCCCCTCCCCCATCTCCCACCCTGTACCTCATCCCATGAGACCCTGGTGCCTGGCTCTTTCGTCACCCTTGGACAAGACAAACCAAG | 22 |

| SEQUENCES | |
|---|---|
| TC | |
| GCTCAGGGCTCTTTCCTCCACACCATTCAGGTCTTTCTTTCCGAGGCCC CTGTCTCAGGGTGAGGTGCTTGAGTCTCCAACGGCAAGGGAACAAGTA CTT | 25 |
| GGAACATCAGAAAGCCTGGGCTTTGAACCTGAACGGTTTTGATGTAGAG GAAGCCAAGATCCTTCGGCTCAGTGGAAAACCACAAAATGCGCCAGAG GGT | 28 |
| CTTTCCCCAAACTGGTGCGGATCCTCACGGCCTTTTCCTCCCTGCAGCA TCTGGACCTGGATGCGCTGAGTGAGAACAAGATCGGGGACGAGGGTGT CTC | 31 |
| CAGACATGAGCTTTGCTGAAATAAAACACAAGTATCTCTGGTCAGAGCC TCAGAATTGCTCAGCCACCAAAAGTAACTACCTTCGAGGTACTGGTCCC TA | 34 |
| ACAGACACGTTTGAGTCCATGCCCAATCCCGAGGGCCGGTATACATTC GGCGCCAGCTGTGTGACTGCCTGTCCCTACAACTACCTTTCTACGGAC GTGG | 37 |
| AGGAACCAGGGAAAATGTGTAGAGGGCATGGTGGAGATCTTCGACATG CTGCTGGCTACATCATCTCGGTTCCGCATGATGAATCTGCAGGGAGAG GAGT | 40 |
| TGATACATTCTCAAGAGTTGCTTGACCGAAAGTTACAAGGACCCCAACC CCTTTGTCCTCTCTACCCACAGATGGGCCCTGGGAATCAATTCCTCAGGA AT | 43 |
| TCGGTGCGGGAGATGTTCGAGTCACAGAGGATCGGCTTGAACAACTCT CCAGTGAACGGGAATAGTAGCTGTCAAATGGCCTTCCCTTCCAGCCAGT CTC | 46 |
| TTATTTGACAAAGAGTTCTGCGAGTGGATGATCCAGCAAATAGGGCCM AACTTGATGGGAAAATCCCGGTGTCCAGAGGGTTTCCTATCGCTGAAGT GT | 49 |
| CCCGTGAGCTGGAAGGAACAGATTTAATATCTAGGGGCTGGGTATCCC CACATCACTCATTTGGGGGGTCAAGGGACCCGGGCAATATAGTATTCTG CTC | 52 |
| GGAGAGATCTGAACTCCAGCTGCCCTACAAACTCCATCTCAGCTTTTCT TCTCACTTCATGTGAAAACTACTCCAGTGGCTGACTGAATTGCTGACCC TT | 55 |
| TCCAAATTGGATACTGCTGCCAAGAAGTTGCTCTGAAGTCAGTTTCTATC ATTCTGCTCTTTGATTCAAAGCACTGTTTCTCTCACTGGGCCTCCAACCA | 58 |
| GGTGGCCTGAGTTCAGCAAATTTGGAGGTTTTGACCCGCAGGGTGCAC TGAGAAACATGGCTGTGGCAAAACACAACTTGAACATCATGATTAAACG CTA | 61 |
| TGCAGACACAACTACGGGGTTGTGGAGAGCTTCACAGTGCAGCGGCGA GTCCAACCTAAGGTGACTGTATATCCTTCAAAGACCCAGCCCCTGCAGC ACC | 64 |
| TTCCTACATGGCAAAGCTGACAGTGACACTGATGGTGCTGAGCTCCCCA CTGGCTTTGGCTGGGACACCCGACCACGTTTCTTGCAGCAGGATAAG TAT | 67 |
| ATACTATCCAGTTACTGCCGGTTTGAAAATATGCCTGCAATCTGAGCCA GTGCTTTAATGGCATGTCAGACAGAACTTGAATGTGTCAGGTGACCCTG AT | 70 |
| TTGCTTTGACCACTCTTCCTGAGTTCAGTGGCACTCAACATGAGTCAAG AGCATCCTGCTTCTACCATGTGGATTTGGTCACAAGGTTTAAGGTGACC CA | 73 |
| AGCAGATGTAGAGGGAGAACTCTTAGCGTGCAGGAATCTAATGCCATCA GCAGGCAAAGCCATGCACACGCCTAAACCATCAGTAGGTGAAGAGAAA GAC | 76 |
| GGAAGTATTCTTCGTGTTACTACAGCTGACCCATATGCCAGTGGAAAAA TCAGCCAGTTTCTGGGGATTTGCATTCAGAGATCAGGAAGAGGACTTGG AG | 79 |

| SEQUENCES | |
|---|---|
| CCTCCAGCCCCTCCTATAGATTCATATTGAATGATGGGACAATGCTTAG CGCCCACACCAAGTGTAAACTTTGCTACCCTCAAAGTCCAGACATGCAA CC | 82 |
| TAGAAGCAGTGAACATGGCTTCAAAGATACTAAAAAGCTATGAGTCCAG TCTTCCCCAGACACAGCAAGTGGATCTTGACTTATCCAGGCCACTTTTC AC | 85 |
| CTTCCCCGAGGACCGCAGCCAGCCCGGCCAGGACTGCCGCTTCCGTG TCACACAACTGCCCAACGGGCGTGACTTCCACATGAGCGTGGTCAGGG CCCGG | 88 |
| AGCCAGCCAGAGCCCACAATACAGCTTCGAGTCATTACCTCAGAAGATT TGTTTAATCTGTGGGGATGAAGCATCAGGCTGTCATTATGGTGTCCTTA CC | 91 |
| CATCGGACAATTTCTGGAGGCTGTGGATCAGAATACAGCCATCGTGGG CTCTACCACAGGCTCCAACTATTATGTGCGCATCCTGAGCACCATCGAT CGG | 94 |
| CGAAATGTTTCATTGTGGGAGCAGACAATGTGGGCTCCAAGCAGATGCA GCAGATCCGCATGTCCCTTCGCGGGAAGGCTGTGGTGCTGATGGGCAA GM | 97 |
| CTTCTAAGCCAGTTGTGGGGATTATTTACCCTCCTCCAGAGGTCAGAAA TATTGTTGACAAGACTGCCAGCTTTGTGGCCAGAAACGGGCCTGAATTT GA | 100 |
| CAAGTGGAGCACCCCAGCCTGGACAGTCCTGTCACCGTGGAGTGGAAG GCACAGTCTGATTCTGTGCAGAGCAAGATGCTGACAGGAGCTAGGGGC TTCA | 103 |
| TGCAGTACCTGAACAGATACATCCATAAACGGGAGGAGAACCTGCGCTT CGACAGCAACGTGGAGGAGTTCCAGGCAGTTACGGAACTGGGGCGGC CTGT | 106 |

| Probe A Sequence | Probe A SEQ ID NO. |
|---|---|
| GATCTTGATCTTCATTGTGCTGGGTGCCAGGGCAGTGATCTCCTTCTGC ACCTCAAGACCTAAGCGACAGCGTGACCTTGTTTCA | 2 |
| CTCACCCATCCCAACACCTCAAGTCACACTCATGAAGATAGAGACAGTC ACATCCTCTTCTTTTCTTGGTGTTGAGAAGATGCTC | 5 |
| AAGTAGCACCTTCCATAGCAGCATCGGGAGCACGCACCACAATTCTGC GGGTTAGCAGGAAGGTTAGGGAAC | 8 |
| ATGCCCTGCAGGCGGACAGAAGCGCGGCTGGTGCGGAGCCTCGGGAA GCTGTTGAGATTATTGAGCTTCATCATGACCAGAAG | 11 |
| GAGAGAAACGTGCTATGTTCCATCTCCCAGCGGAACTCATCCAGTAGAT ACAAAGACGCCTATCTTCCAGTTTGATCGGGAAACT | 14 |
| AGGTCAAAGGTGATCCAAGACTTGGAGGAGGAAGCCCTCTCCGCCCGA ACCTAACTCCTCGCTACATTCCTATTGTTTTC | 17 |
| AACCCAGTGTTCCTCTCTACCTGCGTATCGTTTTAGAAAGTTCATGTCCT CCAATTTGGTTTTACTCCCCTCGATTATGCGGAGT | 20 |
| TCATGGGATGAGGTACAGGGTGGGAGATGGGGAGCTTTCGGGTTATA TCTATCATTTACTTGACACCCT | 23 |
| GGGGCCTCGGAAAGAAAGACCTGAATGGTGTGGAGGAAAGAGCCCTGA GCCAACAGCCACTTTTTTTCCAAATTTTGCAAGAGCC | 26 |
| CCTCTACATCAAAACCGTTCAGGTTCAAAGCCCAGGCTTTCTGATGTTC CCACCGTGTGGACGGCAACTCAGAGATAACGCATAT | 29 |
| ATGCTGCAGGGAGGAAAAGGCCGTGAGGATCCGCACCAGTTTGGGGAA AGCCTGGAGTTTATGTATTGCCAACGAGTTTGTCTTT | 32 |
| AGGCTCTGACCAGAGATACTTGTGTTTTATTTCAGCAAAGCTCATGTCTG CAGATAAGGTTGTTATTGTGGAGGATGTTACTACA | 35 |
| CCGAATGTATACCGGCCCTCGGGATTGGGCATGGACTCAAACGTGTCC | 38 |

| SEQUENCES | |
|---|---|
| TTCCTTCCTGTGTTCCAGCTACAAACTTAGAAAC | |
| AGCATGTCGAAGATCTCCACCATGCCCTCTACACATTTTCCCTGGTTCAT AAAATTGGTTTTGCCTTTCAGCAATTCAACTT | 41 |
| GGGTTGGGGTCCTTGTAACTTTCGGTCAAGCAACTCTTGAGAATGTATC ACTGGTCAAGACTTGCATGAGGACCCGCAAATTCCT | 44 |
| GGAGAGTTGTTCAAGCCGATCCTCTGTGACTCGAACATCTCCCGCTTTC GTTGGGACGCTTGAAGCGCAAGTAGAAAAC | 47 |
| TTTGGCCCTATTTGCTGGATCATCCACTCGCAGAACTCTTTGTCAAATAA CCAGCAGACCTGCAATATCAAAGTTATAAGCGCGT | 50 |
| TGGGGATACCCAGCCCCTAGATATTAAATCTGTTCCTTCCAGCTCACGC CTGCCAATGCACTCGATCTTGTCATTTTTTTGCG | 53 |
| AAGAAAAGCTGAGATGGAGTTTGTAGGGCAGCTGGAGTTCAGATCTCTC CCAAACTGGAGAGAGAAGTGAAGACGATTTAACCCA | 56 |
| GATAGAAACTGACTTCAGAGCAACTTCTTGGCAGCAGTATCCAATTTGG ACGATTGCTGCATTCCGCTCAACGCTTGAGGAAGTA | 59 |
| CAGTGCACCCTGCGGGTCAAAACCTCCAAATTTGCTGAACTCAGGCCAC CCTGAGGCTGTTAAAGCTGTAGCAACTCTTCCACGA | 62 |
| GCACTGTGAAGCTCTCCACAACCCCGTAGTTGTGTCTGCACTAGGACG CAAATCACTTGAAGAAGTGAAAGCGAG | 65 |
| GTGGGGAGCTCAGCACCATCAGTGTCACTGTCAGCTTTGCCATGTAGG AACCACGCGATGACGTTCGTCAAGAGTCGCATAATCT | 68 |
| CTGGCTCAGATTGCAGGCATATTTTCAAACCGGCAGTAACTGGATAGTA TCATTTGGAATGATGTGTACTGGGAATAAGACGACG | 71 |
| TCTTGACTCATGTTGAGTGCCACTGAACTCAGGAAGAGTGGTCAAAGCA ACACAAGAATCCCTGCTAGCTGAAGGAGGGTCAAAC | 74 |
| CTGATGGCATTAGATTCCTGCACGCTAAGAGTTCTCCCTCTACATCTGC TTGACGTAGATTGCTATCAGGTTACGATGACTGC | 77 |
| ATTTTTCCACTGGCATATGGGTCAGCTGTAGTAACACGAAGAATACTTCC CTTACAGATCGTGTGCTCATGACTTCCACAGACGT | 80 |
| GCTAAGCATTGTCCCATCATTCAATATGAATCTATAGGAGGGGCTGGAG GCTTGGAGGAGTTGATAGTGGTAAAACAACATTAGC | 83 |
| ACTGGACTCATAGCTTTTTAGTATCTTTGAAGCCATGTTCACTGCTTCTA CCTACGTATATATCCAAGTGGTTATGTCCGACGGC | 86 |
| TGACACGGAAGCGGCAGTCCTGGCCGGGCTGGCTGCAGCAAGAAGGA GTATGGAACTTATAGCAAGAGAG | 89 |
| AAATCTTCTGAGGTAATGACTCGAAGCTGTATTGTGGGCTCTGGCTGGC TCACCCCTCCAAACGCATTCTTATTGGCAAATGGAA | 92 |
| AGCCCACGATGGCTGTATTCTGATCCACAGCCTCCAGAAATTGTCCGAT GCCCGAAGCAATACTGTCGTCACTCTGTATGTCCGT | 95 |
| CTGCATCTGCTTGGAGCCCACATTGTCTGCTCCCACAATGAAACATTTC GCCGGGAATCGGCATTTCGCATTCTTAGGATCTAAA | 98 |
| ATTTCTGACCTCTGGAGGAGGGTAAATAATCCCCACAACTGGCTTAGAA GCCGATCTTCATAACGGACAAACTGAACGGGCCATT | 101 |
| GCCTTCCACTCCACGGTGACAGGACTGTCCAGGCTGCGCTATGCAGAC GAGCTGGCAGAGGAGAGAAATCA | 104 |
| GAAGCGCAGGTTCTCCTCCCGTTTATGGATGTATCTGTTCAGCATTCGC AACCATGTGAAGTAATGTGAGCGTACTT | 107 |

| Probe B Sequence | Probe B SEQ ID NO. |
|---|---|
| CGAAAGCCATGACCTCCGATCACTCAGGATGGAGCCGCCGATCCACAC GGAGTACTTGCGCTCAGGAGGAGCAAT | 3 |

-continued

| SEQUENCES | |
|---|---|
| CGAAAGCCATGACCTCCGATCACTCAGAAGAGAAGCAGGGGTTAATCCACTCACTTTCCTCTTTAGAGAAGCTCC | 6 |
| CGAAAGCCATGACCTCCGATCACTCCCCTCCACAGCTTCAAGCTTTTGTTGTTGTGGGAGTCCCTTAGGTC | 9 |
| CGAAAGCCATGACCTCCGATCACTCTGCCAGTAGGTCATGAATATAAAGACAGCAAATATCCTCATCTTTCTGGA | 12 |
| CGAAAGCCATGACCTCCGATCACTCTCACTTGCGAGAGAAGGGTAGCCAGTACCAGGCCA | 15 |
| CGAAAGCCATGACCTCCGATCACTCTTAGGGTCCTGGGTAACCCGTTTTACAGACACTTCCTTGTTCTTC | 18 |
| CGAAAGCCATGACCTCCGATCACTCTCTTTGCCATTTGACCACTTCCATGGGTGACCAGGTTCCTTTTTCAGTCC | 21 |
| CGAAAGCCATGACCTCCGATCACTCTTGGTTIGTCTIGTCCAAGGGTGACGAAAGAGCCAGGCACCAGGGTC | 24 |
| CGAAAGCCATGACCTCCGATCACTCAAGTACTTGTTCCCTTGCCGTTGGAGACTCAAGCACCTCACCCTGAGACA | 27 |
| CGAAAGCCATGACCTCCGATCACTCACCCTCTGGCGCATTTTGTGGTTTTCCACTGAGCCGAAGGATCTTGGCTT | 30 |
| CGAAAGCCATGACCTCCGATCACTCCTCGTCCCCGATCTTGTTCTCACTCAGCGCATCCAGGTCCAG | 33 |
| CGAAAGCCATGACCTCCGATCACTCGACCAGTACCTCGAAGGTAGTTACTTTTGGTGGCTGAGCAATTCTG | 36 |
| CGAAAGCCATGACCTCCGATCACTCCGTAGAAAGGTAGTTGTAGGGACAGGCAGTCACACAGCTGGCG | 39 |
| CGAAAGCCATGACCTCCGATCACTCTCCCTGCAGATTCATCATGCGGAACCGAGATGATGTAGCCAGC | 42 |
| CGAAAGCCATGACCTCCGATCACTCATTCCTGAGGAATTGATTCCCAGGGCCATCTGTGGGTAGAGAGGACAAAG | 45 |
| CGAAAGCCATGACCTCCGATCACTCGAGACTGGCTGGAAGGGAAGGCCATTTGACAGCTACTATTCCCGTTCACT | 48 |
| CGAAAGCCATGACCTCCGATCACTCACACTTCAGCGATAGGAAACCCTCTGGACACCGGGATTTTCCCATCAAGT | 51 |
| CGAAAGCCATGACCTCCGATCACTCGAGCAGAATACTATATTGCCCGGGTCCCTTGACCCCCAAATGAGTGATG | 54 |
| CGAAAGCCATGACCTCCGATCACTCAAGGGTCAGCAATTCAGTCAGCCACTGGAGTAGTTTTCACATGAAGTGAG | 57 |
| CGAAAGCCATGACCTCCGATCACTCTGGTTGGAGGCCCAGTGAGAGAAACAGTGCTTTGAATCAAAGAGCAGAAT | 60 |
| CGAAAGCCATGACCTCCGATCACTCTAGCGTTTAATCATGATGTTCAAGTTGTGTTTTGCCACAGCCATGTTTCT | 63 |
| CGAAAGCCATGACCTCCGATCACTCTTTGAAGGATATACAGTCACCTTAGGTTGGACTCGCCGCT | 66 |
| CGAAAGCCATGACCTCCGATCACTCATACTTATCCTGCTGCAAGAAACGTGGTCGGGTGTCCCCAGCCAAAGCCA | 69 |
| CGAAAGCCATGACCTCCGATCACTCATCAGGGTCACCTGACACATTCAAGTTCTGTCTGACATGCCATTAAAGCA | 72 |
| CGAAAGCCATGACCTCCGATCACTCTGGGTCACCTTAAACCTTGTGACCAAATCCACATGGTAGAAGCAGGATGC | 75 |
| CGAAAGCCATGACCTCCGATCACTCGTCTTTCTCTTCACCTACTGATGGTTTAGGCGTGTGCATGGCTTTGCCTG | 78 |
| CGAAAGCCATGACCTCCGATCACTCCCAAGTCCTCTTCCTGATCTCTGA | 81 |

-continued

| SEQUENCES | |
|---|---|
| ATGCAAATCCCCAGAAACTGGCTG | |
| CGAAAGCCATGACCTCCGATCACTCGGTTGCATGTCTGGACTTTGAGG GTAGCAAAGTTTACACTTGGTGTGGGC | 84 |
| CGAAAGCCATGACCTCCGATCACTCGTGAAAAGTGGCCTGGATAAGTCA AGATCCACTTGCTGTGTCTGGGGAAG | 87 |
| CGAAAGCCATGACCTCCGATCACTCCTGACCACGCTCATGTGGAAGTCA CGCCCGTTGGGCAGTTGTG | 90 |
| CGAAAGCCATGACCTCCGATCACTCGGTAAGGACACCATAATGACAGC CTGATGCTTCATCCCCACAGATTAAAC | 93 |
| CGAAAGCCATGACCTCCGATCACTCCCGATCGATGGTGCTCAGGATGC GCACATAATAGTTGGAGCCTGTGGTAG | 96 |
| CGAAAGCCATGACCTCCGATCACTCCACCACAGCCTTCCCGCGAAGGG ACATGCGGATCTG | 99 |
| CGAAAGCCATGACCTCCGATCACTCTCAAATTCAGGCCCGTTTCTGGCC ACAAAGCTGGCAGTCTTGTCAACAAT | 102 |
| CGAAAGCCATGACCTCCGATCACTCTGAAGCCCCTAGCTCCTGTCAGCA TCTTGCTCTGCACAGAATCAGACTGT | 105 |
| CGAAAGCCATGACCTCCGATCACTCAGTTCCGTAACTGCCTGGAACTCC TCCACGTTGCTGTC | 108 |

The invention claimed is:

1. A method of determining the risk of recurrence of cancer in a subject, the method comprising:
   determining the level of expression in the subject of at least one Housekeeping gene selected from ACTB, MRPL19, RPLP0, PSMC4, and SF3A1;
   calculating a Housekeeping Score for the subject, which is the geometric mean of the expression levels of the Housekeeping genes;
   calculating a Normalization Factor for the subject, which is a Housekeeping Control divided by the Housekeeping Score for the subject;
   determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1;
   calculating a normalized expression level of each MHCII gene by multiplying the determined level of expression of each MHCII gene by the Normalization Factor for the subject;
   calculating a MHCII Score for the subject, wherein the MHCII Score is the geometric mean of the normalized expression levels of the MHCII genes;
   determining the level of expression in the subject of at least one TIL gene selected from CD3D, CD4, CD8A, CD69, IFNG, IL7R, PDCD1, CD274, and ARHGAP9;
   calculating a normalized expression level of each TIL gene by multiplying the determined level of expression of each TIL gene by the Normalization Factor for the subject;
   calculating a TIL Score for the subject, wherein the TIL Score is the geometric mean of the normalized expression levels of the TIL genes;
   determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and
   determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

2. The method of claim 1, wherein the Housekeeping Control is the arithmetic mean of the Housekeeping Scores for a set of control samples, and wherein the control samples are from other subjects with cancer.

3. The method of claim 1, wherein the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity.

4. The method of claim 1, wherein the level of expression in the subject of each Housekeeping gene selected from ACTB, MRPL19, RPLP0, PSMC4, and SF3A1 is determined.

5. The method of claim 1, wherein the level of expression of each MHCII gene is determined and the level of expression of each TIL gene is determined.

6. The method of claim 1, wherein the level of expression of the genes is determined using a NanoString nCounter platform, and wherein the subject is determined to have an increased risk of cancer recurrence when the Immune Activation Score is less than a threshold value, and that the subject has a decreased risk of cancer recurrence when the Immune Activation Score is greater than or equal to the threshold value, wherein the threshold value is at least about 1750, at least about 2000, or at least about 2400.

7. The method of claim 1, wherein the subject is determined to have a high risk of cancer recurrence when the Immune Activation Score is less than a first threshold value, and that the subject has a decreased risk of cancer recurrence when the Immune Activation Score is greater than or equal to the first threshold value and less than a second threshold value, and that the subject is determined to have a low risk of cancer recurrence when the Immune Activation Score is greater than or equal to the second threshold value.

8. The method of claim 1, the method further comprising administering chemotherapy to the subject determined to have an increased risk or a high risk of cancer recurrence.

9. The method of claim 1, the method further comprising abstaining from administering chemotherapy to the subject determined to have a decreased risk or a low risk of cancer recurrence.

10. The method of claim 1, the method further comprising administering immunotherapy to the subject determined to have a decreased risk or a low risk of cancer recurrence.

11. A method of diagnosing a subject with triple-negative breast cancer (TNBC) as having TNBC Basal-like subtype, the method comprising:
determining the level of expression in the subject of at least one Housekeeping gene selected from ACTB, MRPL19, RPLP0, PSMC4, and SF3A1;
calculating a Housekeeping Score for the subject, which is the geometric mean of the expression levels of the Housekeeping genes;
calculating a Normalization Factor for the subject, which is a Housekeeping Control divided by the Housekeeping Score for the subject;
determining the level of expression in the subject of at least one Basal-like gene selected from FOXC1, MKI67, CDC20, CCNE1, and ORC6;
calculating a normalized expression level of each Basal-like gene by multiplying the determined level of expression of each Basal-like gene by the Normalization Factor for the subject;
calculating a Basal-like Subtype Score for the subject, which is the geometric mean of the normalized expression levels of the Basal-like genes;
determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score.

12. The method of claim 11, wherein the control Basal-like Subtype Score is the arithmetic mean of Basal-like Subtype Scores for a set of samples from other subjects with breast cancer.

13. The method of claim 11, wherein the level of expression of the genes is determined using a NanoString nCounter platform, and wherein the subject is determined to have TNBC Basal-like subtype when the Basal-like Subtype Score for the subject is greater than or equal to 350, and that the subject does not have TNBC Basal-like subtype when the Basal-like Subtype Score for the subject is less than 350.

14. The method of claim 11, further comprising determining the risk of recurrence of cancer in the subject according to any one of claims 1-7 when the subject is determined to have TNBC Basal-like subtype.

15. A method of treating cancer in a subject, the method comprising:
determining an Immune Activation Score for the subject that is less than a control Immune Activation Score according to claim 1; and
administering chemotherapy to the subject determined to have an increased risk of cancer recurrence.

16. A method of treating cancer in a subject, the method comprising:
determining an Immune Activation Score for the subject that is greater than or equal to a control Immune Activation Score according to claim 1; and
administering immunotherapy to the subject determined to have a decreased risk of cancer recurrence.

17. A method of diagnosing a subject with triple-negative breast cancer (TNBC) as having TNBC Basal-like subtype and determining the risk of recurrence of cancer in the subject, the method comprising:
determining the level of expression in the subject of at least one Housekeeping gene selected from ACTB, MRPL19, RPLP0, PSMC4, and SF3A1;
calculating a Housekeeping Score for the subject, which is the geometric mean of the expression levels of the Housekeeping genes;
calculating a Normalization Factor for the subject, which is a Housekeeping Control divided by the Housekeeping Score for the subject;
determining the level of expression in the subject of at least one Basal-like gene selected from FOXC1, MKI67, CDC20, CCNE1, and ORC6;
calculating a normalized expression level of each Basal-like gene by multiplying the determined level of expression of each Basal-like gene by the Normalization Factor for the subject;

calculating a Basal-like Subtype Score for the subject, which is the geometric mean of the normalized expression levels of the Basal-like genes;

determining that the subject has TNBC Basal-like subtype when the Basal-like Subtype Score for the subject is greater than or equal to a control Basal-like Subtype Score, and that the subject does not have TNBC Basal-like subtype when the Basal-like Subtype Score for the subject is less than the control Basal-like Subtype Score;

determining the level of expression in the subject of at least one MHCII gene selected from CIITA, CD74, HLA-DPA1, HLA-DPB1, HLA-DPB2, HLA-DRB1, HLA-DMA, HLA-DMB, CTSH, and NCOA1;

calculating a normalized expression level of each MHCII gene by multiplying the determined level of expression of each MHCII gene by the Normalization Factor for the subject;

calculating a MHCII Score for the subject, wherein the MHCII Score is the geometric mean of the normalized expression levels of the MHCII genes;

determining the level of expression in the subject of at least one TIL gene selected from CD3D, CD4, CD8A, CD69, IFNG, IL7R, PDCD1, CD274, and ARHGAP9;

calculating a normalized expression level of each TIL gene by multiplying the determined level of expression of each TIL gene by the Normalization Factor for the subject;

calculating a TIL Score for the subject, wherein the TIL Score is the geometric mean of the normalized expression levels of the TIL genes;

determining an Immune Activation Score for the subject, wherein the Immune Activation Score is the geometric mean of the MHCII Score and the TIL Score, and wherein the Immune Activation Score is calculated using the normalized expression levels of at least three genes from the set of TIL genes and MHCII genes; and determining that the subject has an increased risk of cancer recurrence when the Immune Activation Score for the subject is less than a control Immune Activation Score, and that the subject has a decreased risk of cancer recurrence when the Immune Activation Score for the subject is greater than the control Immune Activation Score.

18. The method of claim 17, wherein the control Basal-like Subtype Score is the arithmetic mean of Basal-like Subtype Scores for a set samples from other subjects with breast cancer.

19. The method of claim 17, wherein the Housekeeping Control is the arithmetic mean of the Housekeeping Scores for a set of control samples, and wherein the control samples are from other subjects with cancer.

20. The method of claim 17, wherein the control Immune Activation Score is determined by performing a ROC curve analysis of Immune Activation Scores of at least 10 other subjects with cancer whose recurrence status is known, and calculating the specificity and sensitivity of all possible Immune Activation Score thresholds for distinguishing between the other subjects with cancer who recur and the other subjects with cancer who do not, wherein the control Immune Activation Score is the Immune Activation Score threshold that provides at least 80% specificity and at least 5% sensitivity.

21. The method of claim 1, wherein the level of expression for the gene is determined by measuring the level of RNA.

22. The method of claim 21, wherein the level of RNA is measured using a NanoString nCounter platform.

23. The method of claim 1, wherein the level of expression in a sample from the subject is determined.

24. The method of claim 23, wherein the sample comprises tissue or blood.

25. The method of claim 23, wherein the sample comprises tumor tissue.

26. The method of claim 1, wherein the cancer comprises breast cancer, ovarian cancer, bladder cancer, or lung cancer.

27. The method of claim 26, wherein the breast cancer is triple-negative breast cancer (TNBC).

28. The method of claim 26, wherein the breast cancer is HER2-enriched breast cancer.

29. The method of claim 26, wherein the lung cancer is squamous cell lung cancer.

* * * * *